(12) United States Patent
Hecker et al.

(10) Patent No.: US 6,723,716 B1
(45) Date of Patent: Apr. 20, 2004

(54) 7-ACYLAMINO-3-HETEROARYLTHIO-3-CEPHEM CARBOXYLIC ACID ANTIBIOTICS AND PRODRUGS THEREOF

(75) Inventors: Scott J. Hecker, Los Gatos, CA (US); Aesop Cho, Mountain View, CA (US); Tomasz W. Glinka, Sunnyvale, CA (US); Trevor Calkins, Londonderry, NH (US); Ving J. Lee, Los Altos, CA (US)

(73) Assignee: Essential Therapeutics, Inc., Waltham, MA (US)

( * ) Notice: Subject to any disclaimer, the term of this patent is extended or adjusted under 35 U.S.C. 154(b) by 0 days.

(21) Appl. No.: 09/668,722

(22) Filed: Sep. 21, 2000

Related U.S. Application Data

(60) Provisional application No. 60/155,496, filed on Sep. 22, 1999.

(51) Int. Cl.[7] ............... C07D 501/59; A61K 31/546; A61P 31/04
(52) U.S. Cl. ............. 514/203; 514/204; 540/224; 540/225; 540/226; 540/227
(58) Field of Search ............... 540/225, 224, 540/226, 227; 514/203, 204

(56) References Cited

U.S. PATENT DOCUMENTS

| | | | | |
|---|---|---|---|---|
| 4,465,668 A | * | 8/1984 | Nishikido et al. | 514/2 |
| 5,389,625 A | * | 2/1995 | Muro et al. | 540/222 |
| 5,859,256 A | * | 1/1999 | Cho | 548/193 |
| 6,025,352 A | * | 2/2000 | Cho | 540/226 |
| 6,030,965 A | * | 2/2000 | Cho | 540/226 |
| 6,057,312 A | * | 5/2000 | Cho et al. | 514/203 |

* cited by examiner

*Primary Examiner*—Mark L. Berch
(74) *Attorney, Agent, or Firm*—Bernard F. Rose, Esq.; Bingham McCutchen LLP

(57) ABSTRACT

The present invention relates to a cephem prodrug having formula III or formula IV:

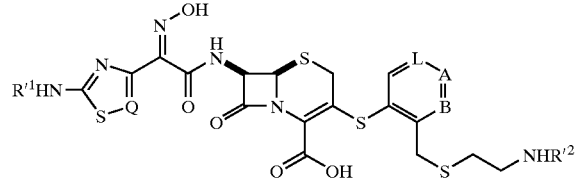

(III)

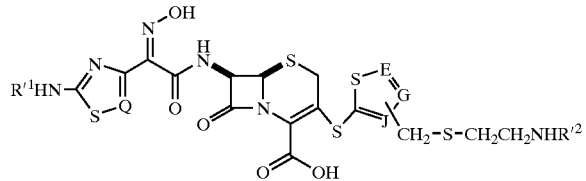

(IV)

or a pharmaceutically acceptable salt thereof, wherein $R^{'1}$ is selected from the group consisting of hydrogen and —C(O)CH(NH$_2$)CH$_3$ and $R^{'2}$ is selected from the group consisting of hydrogen and an acyl group that is cleaved by an enzyme found in mammals, with the proviso that, when either $R^{'1}$ or $R^{'2}$ is hydrogen, the other is not. A, B, L, G, E, and J are each independently nitrogen or carbon such that the respective rings are selected from the group consisting of

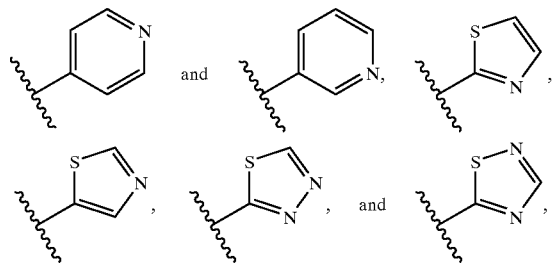

provided that the group —CH$_2$—S—CH$_2$CH$_2$NHR$^{'2}$ is attached only to a carbon atom of said heterocyclic group, and Q is selected from the group consisting of nitrogen and —CX, wherein X is selected from the group consisting of hydrogen and chlorine.

23 Claims, No Drawings

7-ACYLAMINO-3-HETEROARYLTHIO-3-CEPHEM CARBOXYLIC ACID ANTIBIOTICS AND PRODRUGS THEREOF

RELATED APPLICATION

This application is related to and claims priority to the U.S. Provisional Application No. 60/155,496, filed Sep. 22, 1999, by Hecker et al., and entitled "7-ACYLAMINO-3-HETEROARYLTHIO-3-CEPHEM CARBOXYLIC ACID ANTIBIOTICS AND PRODRUGS THEREOF" (Lyon & Lyon Docket No. 241/154), which is hereby incorporated by reference in its entirety, including any drawings.

FIELD OF THE INVENTION

The present invention relates to novel cephalosporin antibiotics and their methods of production and use, as well as prodrugs thereof. These compounds exhibit antibiotic activity against a wide spectrum of organisms, including organisms which are resistant to conventional β-lactam antibiotics.

BACKGROUND OF THE INVENTION

The following review of the background of the invention is merely provided to aid in the understanding of the present invention and neither it nor any of the references cited within it are admitted to be prior art to the present invention.

Over the past three decades a large variety of antibiotics has become available for clinical use. One class of antibiotics which has seen remarkable growth are the cephalosporins, over 70 of which have entered clinical use for the treatment of bacterial infections in mammals since 1965. The cephalosporins exhibit their antibacterial activity by inhibiting bacterial peptidoglycan biosynthesis, and have been extremely effective in treating a wide variety of bacterial infections. Cephalosporins that are said to have antibacterial activity are described in U.S. Pat. No. 3,992,377 and U.S. Pat. No. 4,256,739.

Unfortunately, the wide-spread and indiscriminant use of these antibiotics has led to a rapid increase in the number of bacterial strains which are resistant to these compounds. Most importantly, this resistance has emerged among clinically important microorganisms which threaten to limit the utility of presently available cephalosporin antibiotics. In particular, resistant strains of Salmonella, S. pneumoniæ, Enterobacteriaceœ, Staphylococcus aureus, and Pseudomonas have emerged which threaten to undo many of the strides made in reducing mortality and morbidity from bacterial infections.

Bacterial resistance to cephalosporins follows three major pathways: (a) the development of β-lactamases capable of inactivating the β-lactam ring of the cephalosporin; (b) decreased cephalosporin penetration into the bacteria due to changes in bacterial cell wall composition; and (c) poor binding to penicillin-binding proteins (PBPs). The latter pathway is especially important, as the binding of β-lactams to PBPs is essential for inhibiting bacterial cell-wall biosynthesis. Certain Gram-positive bacteria, namely methicillin-resistant Staphylococcus aureus ("MRSA") and Enterococci are highly resistant to β-lactam antibiotics. Resistance in MRSA is due to the presence of high levels of an unusual PBP, PBP2a, which is insensitive, or binds poorly, to β-lactam antibiotics. The activity of β-lactam antibiotics against PBP2a-containing organisms has been shown to correlate well with the binding affinity of the antibiotic to PBP2a. Currently, the glycopeptides vancomycin and teicoplanin are primarily used for MRSA bacteremia. The quinolone antibacterials and some carbapenems, such as imipenem, have been reported to be active against a few MRSA strains, but their use is restricted due to emerging resistant MRSA strains.

Experimental compounds which may possess utility as anti-MRSA or anti-enterococcal bactericides include the glycylcyclines (see, e.g., P.-E. Sum et al., J. Med. Chem., 37, (1994)), FK-037 (see, e.g., H. Ohki et al., J. Antibiotics, 46:359–361 (1993)), RP-59,500 (see, e.g., S. K. Spangler et al., Antimicro. Agents Chemother., 36:856–9 (1992)), the everninomycin complex (see, e.g., W. E. Sanders et al., Antimicro. Agents Chemother., 6: 232–8 (1974)), the 2-(biaryl)carbapenems (see, e.g., U.S. Pat. No. 5,025,006), 3-(benzothiazolylthio)cephems (see, e.g., EP Application No. 527686), 3-(thiazolylthio)carbacephems (see, e.g., R. J. Ternansky et al., J. Med. Chem., 36:1971 (1993) and U.S. Pat. No. 5,077,287) and arbekacin (S. Kondo, et al. J. Antibiotics 46:531 (1993).

Recent advances in the compounds, compositions and methods useful for treating infections in mammals arising from β-lactam antibiotic resistant bacteria are described in commonly owned International Application No. PCT/US95/03976 and U.S. patent applications Ser. No. 08/222,262, filed Apr. 1, 1994; Ser. No. 08/369,798, filed Jan. 6, 1995; Ser. Nos. 08/413,713, 08/413,714, 08/415,065, 08/413,712, 08/415,064, and Ser. No. 08/415,069, all of which were filed on Mar. 29, 1995; Ser. No. 08/455,969, filed May 31, 1995; Ser. No. 08/457,673, filed Jun. 1, 1995; Ser. Nos. 08/940,508 and 08/937,812, both of which were filed Sep. 29, 1997; Ser. Nos. 08/730,041, 08/730,039, 08/728,232, 08/430,042, 08/728,233, and 08/730,040, all of which were filed Oct. 1, 1996; and Ser. No. 08/842,915, filed Apr. 17, 1997; all of which are incorporated herein by reference in their entirety, including any drawings.

SUMMARY OF THE INVENTION

The present invention includes compounds, compositions and methods effective to treat infections in mammals arising from β-lactam antibiotic resistant bacteria. Preferred compounds will have a minimum inhibitory concentration (MIC) that is less that 50%, more preferably less than 10%, and most preferably less than 1% of the MIC of cefotaxime or imipenem for a beta-lactam resistant organism, preferably a methicillin-resistant Staphylococcal organism. Other preferred compounds will be able to prevent or reduce mortality in mice infected with the beta-lactam resistant organism to a greater extent than cefotaxime or imipenem.

Compounds from the class of 7-acylamino-3-heteroarylthio-3-cephem carboxylic acids of this invention have higher chemical reactivity and lower stability towards chemical or enzymatic decomposition than other cephalosporin compounds known in the art. Without wishing to be bound by any particular theory of operation of the invention, it is believed that this is due to an unusual type of substitution at the 3-position of the cephalosporin system. One aspect of the present invention features certain compounds from the class of 7-acylamino-3-heteroarylthio-3-cephem carboxylic acids which display an unexpected advantage over other compounds of this class, by virtue of lowered susceptibility to decomposition by enzymes present in mammalian serum. Compounds having this property are described below, and data is presented showing their improved stability in mammalian serum. In addition to this increased stability, there is also an improvement in pharmacokinetic parameters of such compounds and especially a lowered clearance of such compounds from the body. Pharmacological data demonstrating this lowered clearance is shown below, as well as improved efficacy in an animal model of infection due to this lowered clearance. One aspect of the present invention features certain compounds from the class of 7-acylamino-3-heteroarylthio-3-cephem carboxylic, acids which combine the above mentioned improved characteristics of increased stability in mammalian serum and lowered clearance with low binding to human serum proteins.

In one aspect the invention features compounds of Formula I or II:

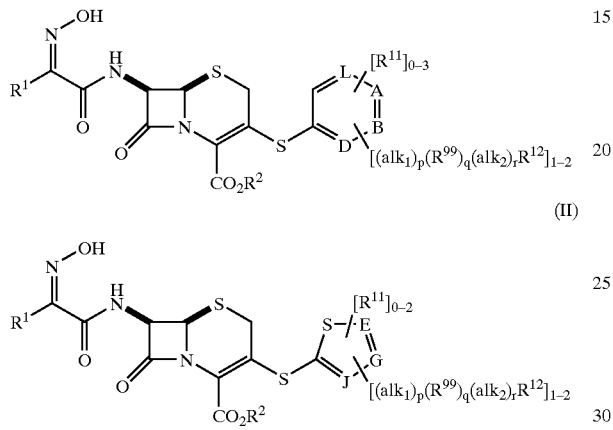

or a pharmaceutically acceptable salt thereof, where $R^1$ is selected from the group consisting of optionally substituted aryl and optionally substituted heterocycle, where the heterocycle is selected from the group consisting of pyridyl, thiadiazolyl, and thiazolyl; and where the aryl and heterocycle are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;

$R^2$ is selected from the group consisting of hydrogen, optionally substituted alkyl, optionally substituted alkenyl, optionally substituted aryl, optionally substituted aralkyl, and trialkylsilyl;

where the alkyl, alkenyl, and aryl are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;

$R^{11}$ is selected from the group consisting of hydrogen, halogen, hydroxy, optionally substituted alkyl, optionally substituted alkoxy, and optionally substituted amino, where the alkyl, alkoxy, and amino are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;

$alk_1$ and $alk_2$ are alkylene groups;

p is 0 or 1;

$R^{99}$ is selected from the group consisting of NH, sulfur, SO, and $SO_2$;

q is 0 or 1;

r is 0 or 1;

$R^{12}$ is selected from the group consisting of $-NR^{21}R^{22}$, $-NR^{23}-C(=NR^{24})-NR^{25}R^{26}$, $-C(=NR^{27})-NR^{28}R^{29}$, and $-NR^{30}-CH(=NR^{31})$ where $R^{21}-R^{31}$ are each independently and optionally selected from the group consisting of hydrogen and alkyl;

A, B, D, L, E, G, and J are each independently nitrogen or carbon, where the specific juxtaposition of groups A, B, D, and L forms a heterocyclic group selected from the group consisting of

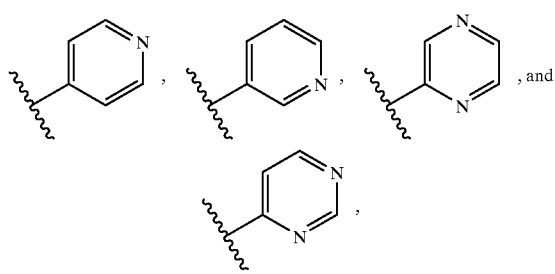

and where the specific juxtaposition of groups E, G, and J forms a heterocyclic group selected from the group consisting of

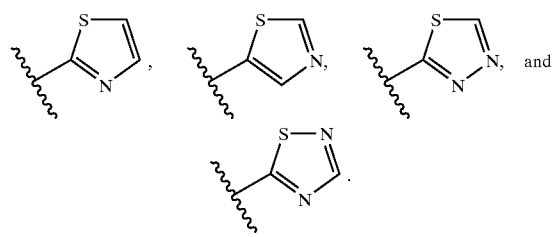

The specific juxtaposition of groups A, B, D, and L or E, G, and J may also form a heterocyclic group, which when connected to the sulfur linkage forms a group as shown below.

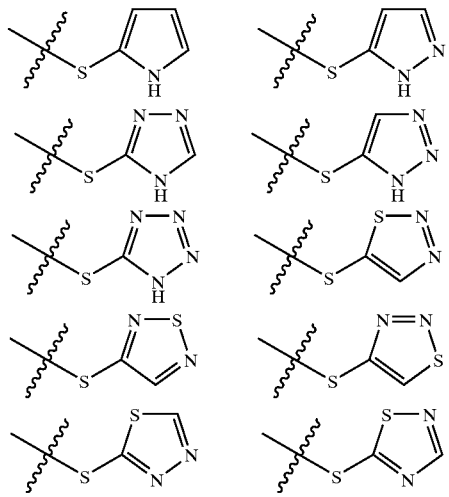

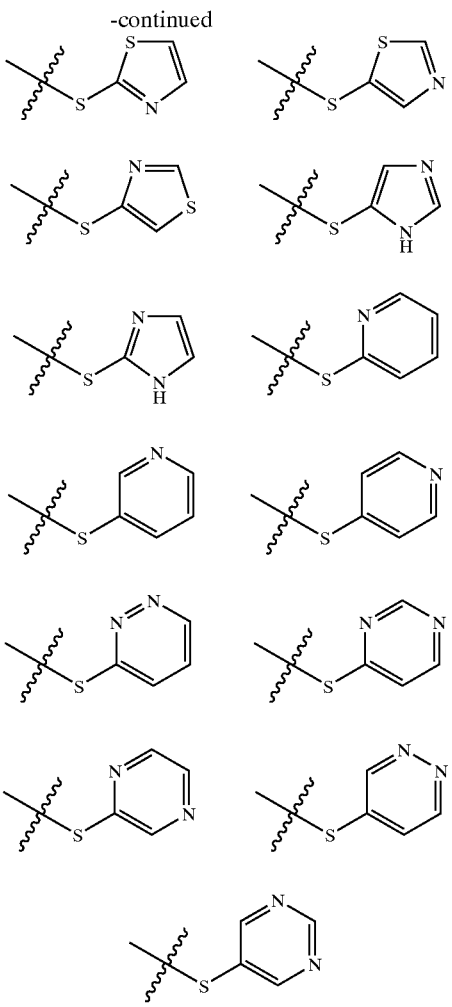

It is understood that a ring of a compound of the invention may be substituted by two specific unidentical substituents, each of which is described by the generic formula [(alk$_1$)$_p$ (R$^{99}$)$_q$(alk$_2$)$_r$R$^{12}$], as defined herein. Similarly, a ring of a compound of the invention may be substituted by two or three specific unidentical substituents, each of which is described by the generic formula R$^{11}$, as defined herein.

In preferred embodiments, R$^1$ in formula I or II is an optionally substituted heterocycle. This heterocycle may be optionally substituted with one or more substituents selected from the group consisting of halogen and amino. More preferably, R$^1$ is selected from the group consisting of 2-aminothiazol-4-yl, 2-amino-5-chlorothiazol-4-yl, 5-amino-1,2,4-thiadiazol-3-yl, and 2-aminopyrid-6-yl.

In these and other preferred embodiments, alk$_1$ and alk$_2$ in the above structures are each independently selected from the group consisting of methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). Furthermore, R$^{99}$ is sulfur or NH. In more preferred embodiments, R$^{11}$ is selected from the group consisting of hydrogen, methyl, methoxy, hydroxy, NH$_2$, and chloro.

Preferably, R$^{21}$-R$^{23}$ are each independently and optionally selected from the group consisting of hydrogen and methyl. R$^{12}$ is preferably selected from the group consisting of —NH$_2$, —NH—C(=NH)—NH$_2$, —C(=NH)—NH$_2$, and —NHCH(=NH).

In preferred embodiments, the specific juxtaposition of groups A, B, D, and L forms Furthermore, the specific juxtaposition of groups E, G, and J preferably forms In these and other preferred embodiments, the invention features compounds of formula I or II, where the compound is selected from the group consisting of Cmpd 1. (7R)-7-[(Z)-2-(2-amino-5-chlorothiazol-4-yl)-2-(hydroxylamino)acetamido-3-(2-aminoethylthio-1,3,4-thiadiazol-5-ylthio)-3-cephem-4-carboxylic acid, Cmpd 2. (7R)-7-[(Z)-2-(2-aminopyrid-6-yl)-2-(hydroxylamino)acetamido]-3-[4-(2-aminoethylthiomethyl)-2-methyl-1,3-thiazol-5-ylthio]-3-cephem-4-carboxylic acid, Cmpd 3. (7R)-7-[(Z)-2-(2-amino-5-chlorothiazol-4-yl)-2-(hydroxyimino)acetamido]-3-[4-(2-aminoethylthiomethyl)-2-amino-1,3-thiazol-5-ylthio]-3-cephem-4-carboxylic acid, Cmpd 4. (7R)-7-[(Z)-2-(2-aminopyrid-6-yl)-2-(hydroxyimino)acetamido]-3-[4-(2-aminoethylthiomethyl)-1,3-thiazol-2-ylthio]-3-cephem-4-carboxylic acid, Cmpd 5. (7R)-7-[(Z)-2-(2-aminopyrid-6-yl)-2-(hydroxyimino)acetamido]-3-[4-(2-aminoethylthiomethyl)-2-methoxy-1,3-thiazol-5-ylthio]-3-cephem-4-carboxylic acid, Cmpd 6. (7R)-7-[(Z)-2-(2-aminopyrid-6-yl)-2-(hydroxyimino)acetamido]-3-[2-(2-aminoethylthio)-pyridazin-6-ylthio]-3-cephem-4-carboxylic acid, Cmpd 7. (7R)-7-[(Z)-2-(2-aminopyrid-6-yl)-2-(hydroxyimino)acetamido]-3-[2-(2-aminoethylthio)-pyridazin-3-ylthio]-3-cephem-4-carboxylic acid, Cmpd 8. (7R)-7-[(Z)-2-(2-aminopyrid-6-yl)-2-(hydroxyimino)acetamido]-3-[2-(2-aminoethylthio)-pyrimidin-4-ylthio]-3-cephem-4-carboxylic acid, Cmpd 9. (7R)-7-[(Z)-2-(2-aminothiazol-4-yl)-2-(hydroxyimino)acetamido]-3-[2-(2-aminoethylthiomethyl)-pyridazin-3-ylthio]-3-cephem-4-carboxylic acid, Cmpd 10. (7R)-7-[(Z)-2-(2-amino-5-chlorothiazol-4-yl)-2-(hydroxyimino)acetamido]-3-(2-aminoethylthiomethyl-1,3,4-thiadiazol-5-ylthio)-3-cephem-4-carboxylic acid, Cmpd 11. (7R)-7-[(Z)-2-(2-amino-5-chlorothiazol-4-yl)-2-(hydroxyimino)acetamido]-3-[4-(2-aminoethylthiomethyl)-2-aminoethylthio-1,3-thiazol-5-ylthio]-3-cephem-4-carboxylic acid, Cmpd 12. (7R)-7-[(Z)-2-(2-amino-5-chlorothiazol-4-yl)-2-(hydroxyimino)acetamido]-3-[3-(2-aminoethylthiomethyl)-1,2,4-thiadiazol-5-ylthio]-3-cephem-4-carboxylic acid, Cmpd 13. (7R)-7-[(Z)-2-(2-amino-5-chlorothiazol-4-yl)-2-(hydroxyimino)acetamido]-3-[2-(2-aminoethylthiomethyl)pyrid-3-ylthio]-3-cephem-4-carboxylic acid, Cmpd 14. (7R)-7-[(Z)-2-(5-amino-1,2,4-thiadiazol-3-yl)-2-(hydroxyimino)acetamido]-3-[2-(2-guanidinoethylthiomethyl)pyrid-3-ylthio]-3-cephem-4-carboxylic acid, Cmpd 15. (7R)-7-[(Z)-2-(2-amino-5-chlorothiazol-4-yl)-2-(hydroxyimino)acetamido]-3-[2-(2-guanidinoethyl-thlomethyl)pyrid-3-ylthio]-3-cephem-4-carboxylic acid, Cmpd 16. (7R)-7-[(Z)-2-(2-amino-5-chlorothiazol-4-yl)-2-(hydroxyimino)acetamido]-3-[4-(2-aminoethylthio-methyl)-2-aminoethylamino-1,3-thiazol-5-ylthio]-3-cephem-4-carboxylic acid, Cmpd 17. (7R)-7-[(Z)-2-(5-amino-1,2,4-thiadiazol-3-yl)-2-(hydroxyimino)acetamido]-3-[2-(2-aminoethylthio-methyl)pyrid-3-ylthio]-3-cephem-4-carboxylic acid, Cmpd 18. (7R)-7-[(Z)-2-(5-amino-1,2,4-thiadiazol-3-yl)-2-(hydroxyimino)acetamido]-3-[3-(2-aminoethylthio-methyl)pyrid-4-ylthio]-3-cephem-4-carboxylic acid, Cmpd 19. (7R)-7-[(Z)-2-(2-aminothiazol-4-yl)-2-(hydroxyimino)-acetamido]-3-[3-(2-aminoethylthio-methyl)pyrid-4-ylthio]-3-cephem-4-carboxylic acid, Cmpd 20. (7R)-7-[(Z)-2-(2-amino-5-chlorothiazol-4-yl)-2-(hydroxyimino)acetamido]-3-[3-(2-aminoethylthio-methyl)pyrid-4-ylthio]-3-cephem-4-carboxylic acid, Cmpd 21. (7R)-7-[(Z)-2-(2-amino-5-chlorothiazol-4-yl)-2-(hydroxyimino)acetamido]-3-[4-(2-aminoethylthio-methyl)pyrid-3-ylthio]-3-cephem-4-carboxylic acid, Cmpd 22. (7R)-7-[(Z)-2-(2-aminopyrid-6-yl)-2-(hydroxyimino)acetamido]-3-(2-aminoethylthio-1,3,4-thiadiazol-5-ylthio)-3-cephem-4-carboxylic acid, Cmpd 23. (7R)-7-[(Z)-2-(2-aminopyrid-6-yl)-2-(hydroxyimino)acetamido]-3-[4-(2-aminoethylthio-methyl)-1,3-thiazol-5-ylthio]-3-cephem-4-carboxylic acid, Cmpd 24. (7R)-7-[(Z)-2-(2-aminopyrid-6-yl)-2-(hydroxyimino)acetamido]-3-[3-(2-aminoethylthio-methyl)pyrid-4-ylthio]-3-cephem-4-carboxylic acid, Cmpd 25. (7R)-7-[(Z)-2-(5-amino-1,2,4-thiadiazol-3-yl)-2-(hydroxyimino)acetamido]-3-[3-(2-guanidinoethyl-thiomethyl)pyrid-4-ylthio]-3-cephem-4-carboxylic acid, Cmpd 26. (7R)-7-[(Z)-2-(2-amino-5-chlorothiazol-4-yl)-2-(hydroxylamino)acetamido]-3-[4-(2-guanidinoethyl-thiomethyl)-2-amino-1,3-thiazol-5-ylthio]-3-cephem-4-carboxylic acid, Cmpd 27. (7R)-7-[(Z)-2-(5-amino-1,2,4-thiadiazol-3-yl)-2-(hydroxyimino)acetamido]-3-[4-(2-aminoethylthio-methyl)pyrid-3-ylthio]-3-cephem-4-carboxylic acid, Cmpd 28. (7R)-7-[(Z)-2-(2-aminopyrid-6-yl)-2-(hydroxyimino)acetamido]-3-[4-(2-aminoethylthiomethyl)pyrid-3-ylthio]-3-cephem-4-carboxylic acid, Cmpd 29. (7R)-7-[(Z)-2-(2-aminopyrid-6-yl)-2-(hydroxyimino)acetamido]-3-[2-chloro-4-(2-aminoethylthio-methyl)-1,3-thiazol-5-ylthio]-3-cephem-4-carboxylic acid.

The structures of these compounds are shown below in Section II.

In more preferred embodiments, the compound of formula I or II is selected from the group consisting of Cmpd 3. (7R)-7-[(Z)-2-(2-amino-5-chlorothiazol-4-yl)-2-(hydroxyimino)acetamido]-3-[4-(2-aminoethylthio-methyl)-2-amino-1,3-thiazol-5-ylthio]-3-cephem-4-carboxylic acid, Cmpd 13. (7R)-7-[(Z)-2-(2-amino-5-chlorothiazol-4-yl)-2-(hydroxyimino)acetamido]-3-[2-(2-aminoethylthio-methyl)pyrid-3-ylthio]-3-cephem-4-carboxylic acid, Cmpd 14. (7R)-7-[(Z)-2-(5-amino-1,2,4-thiadiazol-3-yl)-2-(hydroxyimino)acetamido]-3-[2-(2-guanidinoethyl-thiomethyl)pyrid-3-ylthio]-3-cephem-4-carboxylic acid, Cmpd 15. (7R)-7-[(Z)-2-(2-amino-5-chlorothiazol-4-yl)-2-(hydroxyimino)acetamido]-3-[2-(2-guanidinoethyl-thiomethyl)pyrid-3-ylthio]-3-cephem-4-carboxylic acid, Cmpd 17. (7R)-7-[(Z)-2-(5-amino-1,2,4-thiadiazol-3-yl)-2-(hydroxyimino)acetamido]-3-[2-(2-aminoethyl-thiomethyl)pyrid-3-ylthio]-3-cephem-4-carboxylic acid, Cmpd 20. (7R)-7-[(Z)-2-(2-amino-5-chlorothiazol-4-yl)-2-(hydroxyimino)acetamido]-3-[4-(2-aminoethylthio-methyl)pyrid-3-ylthio]-3-cephem-4-carboxylic acid, Cmpd 23. (7R)-7-[(Z)-2-(2-aminopyrid-6-yl)-2-(hydroxyimino)acetamido]-3-[4-(2-aminoethylthio-methyl)-1,3-thiazol-5-ylthio]-3-cephem-4-carboxylic acid, Cmpd 25. (7R)-7-[(Z)-2-(5-amino-1,2,4-thiadiazol-3-yl)-2-(hydroxyimino)acetamido]-3-[3-(2-guanidinoethyl-thlomethyl)pyrid-4-ylthio]-3-cephem-4-carboxylic acid, and Cmpd 27. (7R)-7-[(Z)-2-(5-amino-1,2,4-thiadiazol-3-yl)-2-(hydroxyimino)acetamido]-3-[4-(2-aminoethylthio-methyl)pyrid-3-ylthio]-3-cephem-4-carboxylic acid.

In even more preferred embodiments, the compound of formula I or II is selected from the group consisting of Cmpd 3. (7R)-7-[(Z)-2-(2-amino-5-chlorothiazol-4-yl)-2-(hydroxyimino)acetamido]-3-[4-(2-aminoethylthio-methyl)-2-amino-1,3-thiazol-5-ylthio]-3-cephem-4-carboxylic acid, Cmpd 13. (7R)-7-[(Z)-2-(2-amino-5-chlorothiazol-4-yl)-2-(hydroxyimino)acetamido]-3-[2-(2-aminoethylthio-methyl)pyrid-3-ylthio]-3-cephem-4-carboxylic acid, Cmpd 17. (7R)-7-[(Z)-2-(5-amino-1,2,4-thiadiazol-3-yl)-2-(hydroxyimino)acetamido]-3-[2-(2-aminoethylthio-methyl)pyrid-3-ylthio]-3-cephem-4-carboxylic acid, Cmpd 21. (7R)-7-[(Z)-2-(2-amino-5-chlorothiazol-4-yl)-2-(hydroxyimino)acetamido]-3-[4-(2-aminoethylthio-methyl)pyrid-3-ylthio]-3-cephem-4-carboxylic acid, and Cmpd 27. (7R)-7-[(Z)-2-(5-amino-1,2,4-thiadiazol-3-yl)-2-(hydroxyimino)acetamido]-3-[4-(2-aminoethylthio-methyl)pyrid-3-ylthio]-3-cephem-4-carboxylic acid.

It is understood that the above-named compounds may be synthesized, purified, and used in their neutral form, as the above names suggest, or as pharmaceutically acceptable salts. The pharmaceutically acceptable salt comprises the above compounds in their charged form, either as cations or anions, along with a counterion. Preferred pharmaceutically acceptable salts include (1) inorganic salts such as sodium, potassium, chloride, bromide, iodide, nitrate, phosphate or sulfate; (2) carboxylate salts such as acetate, propionate, butyrate, maleate, or fumarate; (3) alkylsulfonates such as methanesulfonate, ethanesulfonate, 2-hydroxyethylsulfonate, n-propylsulfonate or isopropylsulfonate; and (4) hydroxycarboxylates such as lactate, malate, and citrate. Generally, pharmaceutically acceptable salts may be obtained by reacting any one of the compounds of the invention with an organic or inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. Pharmaceutically acceptable salts may also be obtained by reacting any one of the compounds of the invention with an organic or inorganic base, such as benzathene, chloroprocaine, choline, diethanolamine, ethylenediamine, meglumine, procain, and the hydroxide, alkoxide, carbonate, bicarbonate, sulfate, bisulfate, amide, alkylamide, or dialkylamide salts of the following metal cations: lithium, sodium, potassium, magnesium, calcium, aluminum, and zinc.

As explained herein, the compounds of the invention have biological activity. The invention features a compound of formula I or II which is active against methicillin-resistant Staphylococci, as demonstrated by a lower minimum inhibitory concentration than methicillin, where the bacteria are selected from the group consisting of S. aureus Col (Meth$^R$) (lac−), S. aureus 76 (Meth$^R$)(lac+), S. aureus ATCC 33593 (Meth$^R$), S. aureus Spain #356 (Meth$^R$), and S. haemolyticus 05 (Meth$^R$).

In another embodiment, the present invention provides for compositions comprising an amount of a compound of formula I or II effective to treat bacterial infections in mammals arising from bacteria resistant to β-lactam antibiotics.

In still another embodiment, the present invention includes methods for treating a bacterial infection in a mammal arising from bacteria resistant to β-lactam antibiotics, or a, mammal suffering from a methicillin-resistant Staphylococcal bacterial infection, comprising administering to such mammal a therapeutically effective amount of a compound of formula I or II. Of course, the compounds of the present invention also have utility in compositions and methods to treat mammals infected with bacteria that are sensitive to conventional β-lactam antibiotics. Thus, the invention also features an antibacterial composition for treating a methicillin-resistant Staphylococcal bacterial infection, comprising a therapeutically effective amount of a compound of formula I or II in a pharmaceutically acceptable carrier or diluent.

In another aspect, the invention features a method of synthesizing a compound of formula I or II, comprising the step of combining a first reactant and a second reactant under conditions that are suitable for the synthesis, where the first reactant is a compound of formula

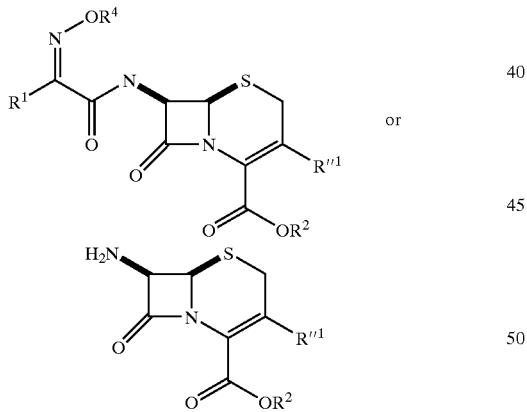

or where
R$^1$ is selected from the group consisting of optionally substituted aryl and optionally substituted heterocycle, where the heterocycle is selected from the group consisting of pyridyl, thiadiazolyl, and thiazolyl; and where the aryl and heterocycle are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;
R$^2$ is selected from the group consisting of hydrogen, optionally substituted alkyl, optionally substituted alkenyl, optionally substituted aryl, optionally substituted aralkyl, and trialkylsilyl;
where the alkyl, alkenyl, and aryl are each independently and optionally substituted with substituents selected from the group consisting of hydroxyl, bromo, fluoro, chloro, iodo, mercapto, cyano, alkylthio, carboxyl; oxo, alkoxycarbonyl, alkyl, alkenyl, nitro, amino, alkoxyl, and carboxamido;
R″$^2$ is selected from the group consisting of p-toluenesulfonate, methanesulfonate, trifluoromethanesulfonate, fluorosulfonate, chloro, bromo, and (R″$^2$O)$_2$PO—,
R″$^2$ is selected from the group consisting of hydrogen and alkyl;
R$^4$ is a protecting group selected from the group consisting of benzyl, p-nitrobenzyl, o-nitrobenzyl, 2,2,2-trichloroethyl, allyl, cinnamyl, benzhydryl, 2-chloroallyl, t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4- or 2-methoxybenzyl, 2,4-dimethoxybenzyl, 3,4-dimethoxybenzyl, 2,4,6-trimethoxybenzyl, methoxymethyl, benzhydryl, and 3,3-dimethylallyl;
the second reactant is a compound of formula MSR$^3$, where
M is hydrogen or a cationic group;
R$^3$ is selected from the group consisting of

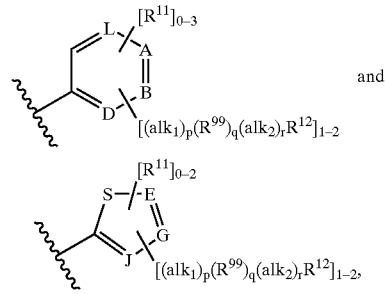

where
R$^{11}$ is selected from the group consisting of hydrogen, halogen, optionally substituted alkyl, optionally substituted alkoxy, and optionally substituted amino,
where the alkyl, alkoxy, and amino are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;
alk$_1$ and alk$_2$ are alkylene groups;
p is 0 or 1;
R$^{99}$ is selected from the group consisting of NH, sulfur, SO, and SO$_2$;
q is 0 or 1;
r is 0 or 1;
R$^{12}$ is selected from the group consisting of —NR$^{21}$R$^{22}$, —NR$^{23}$—C(=NR$^{24}$)—NR$^{25}$R$^{26}$, —C(=NR$^{27}$)—NR$^{28}$R$^{29}$ and —NR$^{30}$—CH(=NR$^{31}$)
where R$^{21}$-R$^{31}$ are each independently and optionally selected from the group consisting of hydrogen and alkyl;
A, B, D, L, E, G, and J are each independently nitrogen or carbon, where the specific juxtaposition of groups A, B, D, and L forms a heterocyclic group selected from the group consisting of

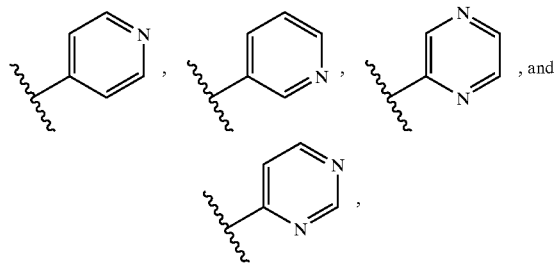

and where the specific juxtaposition of groups E, G, and J forms a heterocyclic group selected from the group consisting of

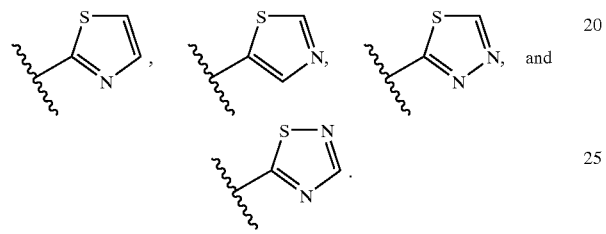

As mentioned above, M may be hydrogen or a cationic group. Cationic groups may be selected from monovalent metal cations, such as, sodium and potassium, or divalent metal cations, such as magnesium and calcium. Other cationic groups, such as, tetra-alkylammonium groups, may also be used.

In another aspect the invention relates to a compound of formula III or formula IV where the specific juxtaposition of groups A, B, and L forms a heterocyclic group selected from the group consisting of

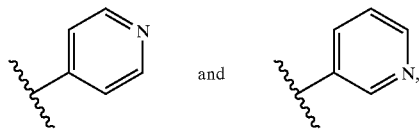

where the specific juxtaposition of groups E, G, and J forms a heterocyclic group selected from the group consisting of

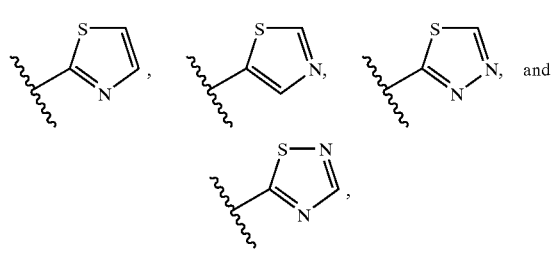

provided that the group —CH$_2$—S—CH$_2$CH$_2$NHR$'^2$ is attached only to a carbon atom of said heterocyclic group;

Q is selected from the group consisting of nitrogen and —CX, wherein X is selected from the group consisting of hydrogen and chlorine.

Preferably, R$'^2$ is selected from the group consisting of hydrogen, —C(O)—R$^{88}$, —C(O)—OR$^{89}$, —C(O)—CH(NHR$'^3$)-alk$_4$, and (III)

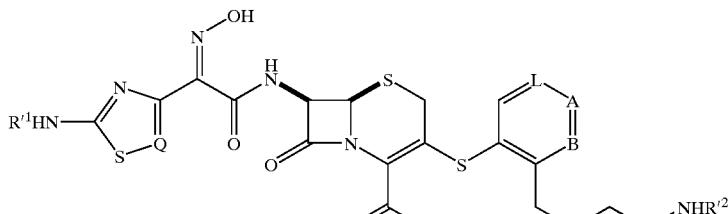

(IV)

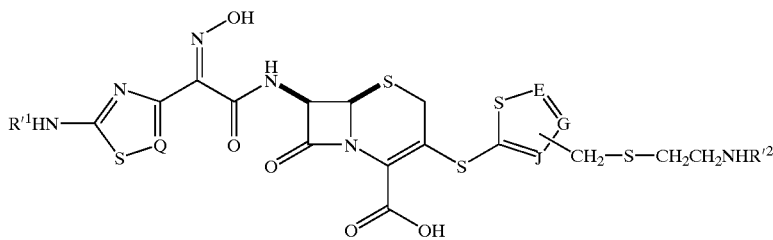

or a pharmaceutically acceptable salt thereof, where

R$'^1$ is selected from the group consisting of hydrogen and —C(O)CH(NH$_2$)CH$_3$; and R$'^2$ is hydrogen or an acyl group that is cleaved by an enzyme found in mammals, as defined herein;

A, B, L, G, E, and J are each independently nitrogen or carbon,

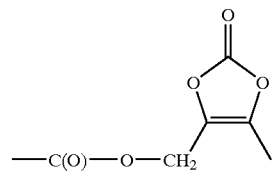

where

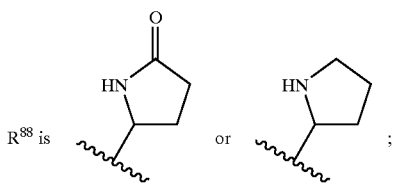

$R^{i3}$ is selected from the group consisting of hydrogen, —C(O)—OR$^{89}$, and —C(O)—CH(NH$_2$)-alk$_4$;

alk$_4$ is selected from the group consisting of hydrogen, and optionally substituted alkyl, wherein said alkyl is optionally substituted with one or more substituents selected from the group consisting of hydrogen, phenyl, —COOH, —C(O)—OR$^{89}$, —C(O)NH$_2$, —OH, —SH, —NH$_2$, and

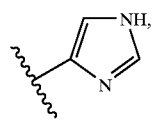

$R^{89}$ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsilyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

More preferably, the compound of formula III, above, is the compound set forth in formula V, (V)

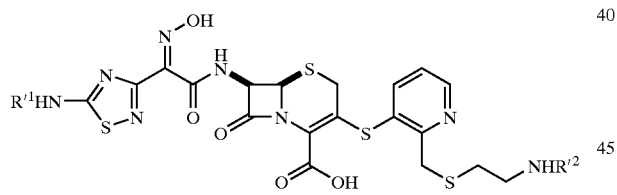

or a pharmaceutically acceptable salt thereof,
where
 R$^{i1}$ is selected from the group consisting of hydrogen and —C(O)CH(NH$_2$)CH$_3$; and
 R$^{i2}$ is hydrogen or an acyl group that is cleaved by an enzyme found in mammals, as defined herein.

Preferably, R$^{i2}$ is selected from the group consisting of hydrogen, —C(O)—R$^{88}$, —C(O)—OR$^{89}$, —C(O)—CH(NHR$^{i3}$)-alk$_4$, and

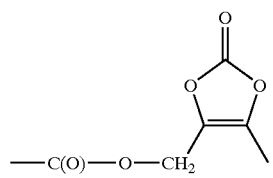

wherein

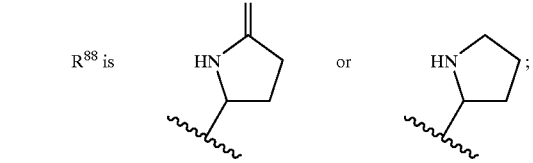

$R^{i3}$ is selected from the group consisting of hydrogen, —C(O)—OR$^{89}$, and —C(O)—CH($_2$)-alk$_4$;

alk$_4$ is selected from the group consisting of hydrogen, and optionally substituted alkyl, wherein said alkyl is optionally substituted with one or more substituents selected from the group consisting of hydrogen, phenyl, —COOH, —C(O)—OR$^{89}$, C(O)NH$_2$, —OH, —SH, —NH$_2$, and

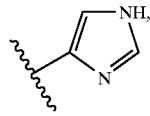

$R^{89}$ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsilyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

In other preferred embodiments R$^{i3}$ is selected from the group consisting of hydrogen, methyl, and —C(O)—CH(NH$_2$)CH$_3$. Furthermore, alk$_4$ is selected from the group consisting of hydrogen, —CH$_3$, —CH(CH$_3$)$_2$, —CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$COOH, —CH$_2$CH$_2$COOH, —CH$_2$—C(O)NH$_2$, —CH$_2$CH$_2$—C(O)NH$_2$, and

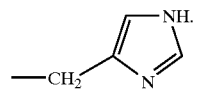

In more preferred embodiments, the invention s a compound of formula III, where the compound is selected from the group consisting of Cmpd 17. (7R)-7-[(Z)-2-(5-amino-1,2,4-thiadiazol-3-yl)-2-(hydroxyimino)acetamido]-3-{2-[2-aminoethylthiomethyl]pyrid-3-ylthio}-3-cephem-4-carboxylic acid, Cmpd 17-A. (7R)-7-[(Z)-2-(5-amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic acid, Cmpd 17-B. (7R)-7-[(Z)-2-(5-amino-1,2,4-thiadiazol-3-yl)-2-(hydroxyimino)acetamido]-3-{2-[2-N-(L)-prolylaminoethylthiomethyl]pyrid-3-ylthio)-3-cephem-4-carboxylic acid, Cmpd 17-C. (7R)-7-[(Z)-2-(5-N-(L)-alanylamino-1,2,4-thiadiazol-3-yl)-2-(hydroxyimino)-acetamido]-3-{2-[2-aminoethylthiomethyl]pyrid-3-ylthio}-3-cephem-4-carboxylic acid, Cmpd 17-D. (7R)-7-[(Z)-2-(5-amino-1,2,4-thiadiazol-3-yl)-2-(hydroxyimino)acetamido]-3-{2-[2-N-(L,L)-alanylalanylaminoethylthiomethyl]pyrid-3-ylthio}-3-cephem-4-carboxylic acid, Cmpd 17-E. (7R)-7-[(Z)-2-(5-amino-1,2,4-thiadiazol-3-yl)-2-(hydroxyimino)acetamido]-3-{2-[2-N-glycylaminoethylthiomethyl]pyrid-3-ylthio}-3-cephem-4-carboxylic acid, Cmpd 17-F. (7R)-7-[(Z)-2-(5-amino-1,2,4-thiadiazol-3-yl)-2-(hydroxyimino)acetamido]-3-{2-[2-N-(L)-aspartylaminoethylthiomethyl]pyrid-3-ylthio}-3-cephem-4-carboxylic acid, Cmpd 17-G. (7R)-7-[(Z)-2-(5-amino-1,2,4-thiadiazol-3-yl)-2-(hydroxyimino)acetamido]-3-{2-[2-N-(L)-alanylaminoethylthiomethyl]pyrid-3-ylthio}-3-cephem-4-carboxylic acid, Cmpd 17-H. (7R)-7-[(Z)-2-(5-amino-1,2,4-thiadiazol-3-yl)-2-(hydroxyimino)acetamido]-3-{2-[2-N-(L)-($N_\alpha$-methyl)alanylaminoethylthiomethyl]pyrid-3-ylthio}-3-cephem-4-carboxylic acid, Cmpd 17-I. (7R)-7-[(Z)-2-(5-amino-1,2,4-thiadiazol-3-yl)-2-(hydroxyimino)acetamido]-3-{2-[2-N-(L)-histidylaminoethylthiomethyl]pyrid-3-ylthio}-3-cephem-4-carboxylic acid, Cmpd 17-J. (7R)-7-[(Z)-2-(5-amino-1,2,4-thiadiazol-3-yl)-2-(hydroxyimino)acetamido]-3-{2-[2-N-(L)-valylaminoethylthiomethyl]pyrid-3-ylthio}-3-cephem-4-carboxylic acid, Cmpd 17-K. (7R)-7-[(Z)-2-(5-amino-1,2,4-thiadiazol-3-yl)-2-(hydroxyimino)acetamido]-3-{2-[2-N-(L)-asparagylaminoethylthiomethyl]pyrid-3-ylthio}-3-cephem-4-carboxylic acid, Cmpd 17-L. (7R)-7-[(Z)-2-(5-amino-1,2,4-thiadiazol-3-yl)-2-(hydroxyimino)acetamido]-3-{2-[2-N-(L)-lysylaminoethylthiomethyl]pyrid-3-ylthio}-3-cephem-4-carboxylic acid, Cmpd 17-M. (7R)-7-[(Z)-2-(5-amino-1,2,4-thiadiazol-3-yl)-2-(hydroxyimino)acetamido]-3-{2-[2-N-(L)-serylaminoethylthiomethyl]pyrid-3-ylthio}-3-cephem-4-carboxylic acid, Cmpd 17-N. (7R)-7-[(Z)-2-(5-amino-1,2,4-thiadiazol-3-yl)-2-(hydroxyimino)acetamido]-3-{2-[2-N-(L)-glutaminylaminoethylthiomethyl]pyrid-3-ylthio}-3-cephem-4-carboxylic acid, Cmpd 17-O. (7R)-7-[(Z)-2-(5-amino-1,2,4-thiadiazol-3-yl)-2-(hydroxyimino)acetamido]-3-{2-[2-(5-methyl-1,3-dioxolan-4-en-2-on-4-yl)methoxycarbonyl)aminoethylthiomethyl]pyrid-3-ylthio}-3-cephem-4-carboxylic acid, and Cmpd 17-P. (7R)-7-[(Z)-2-(5-amino-1,2,4-thiadiazol-3-yl)-2-(hydroxyimino)acetamido]-3-{2-(2-N-(L)-pyroglutamylaminoethylthiomethyl]pyrid-3-ylthio}-3-cephem-4-carboxylic acid.

In even more preferred embodiments, the invention features a compound of formula III, where the compound is selected from the group consisting of Cmpd 17-A. (7R)-7-[(Z)-2-(5-amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic acid, Cmpd 17-D. (7R)-7-[(Z)-2-(5-amino-1,2,4-thiadiazol-3-yl)-2-(hydroxyimino)acetamido]-3-{2-[2-N-(L,L)-alanylalanylaminoethylthiomethyl]pyrid-3-ylthio}-3-cephem-4-carboxylic acid, Cmpd 17-F. (7R)-7-[(Z)-2-(5-amino-1,2,4-thiadiazol-3-yl)-2-(hydroxyimino)acetamido]-3-{2-[2-N-(L)-aspartylaminoethylthiomethyl]pyrid-3-ylthio}-3-cephem-4-carboxylic acid, Cmpd 17-G. (7R)-7-[(Z)-2-(5-amino-1,2,4-thiadiazol-3-yl)-2-(hydroxyimino)acetamido]-3-{2-[2-N-(L)-alanylaminoethylthiomethyl]pyrid-3-ylthio}-3-cephem-4-carboxylic acid, Cmpd 17-L. (7R)-7-[(Z)-2-(5-amino-1,2,4-thiadiazol-3-yl)-2-(hydroxyimino)acetamido]-3-{2-[2-N-(L)-lysylaminoethylthiomethyl]pyrid-3-ylthio}-3-cephem-4-carboxylic acid, Cmpd 17-N. (7R)-7-[(Z)-2-(5-amino-1,2,4-thiadiazol-3-yl)-2-(hydroxyimino)acetamido]-3-{2-[2-N-(L)-glutaminylaminoethylthiomethyl]pyrid-3-ylthio}-3-cephem-4-carboxylic acid, and Cmpd 17-O. (7R)-7-[(Z)-2-(5-amino-1,2,4-thiadiazol-3-yl)-2-(hydroxyimino)acetamido]-3-{2-[2-(5-methyl-1,3-dioxolan-4-en-2-on-4-yl)methoxycarbonyl)aminoethylthiomethyl]pyrid-3-ylthio}-3-cephem-4-carboxylic acid.

In another aspect, the invention provides for a heteroaryl compound, or a salt thereof, selected from the group consisting of 3-triphenylmethylthio-2-hydroxymethylpyridine,

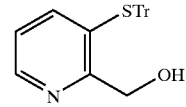

3-triphenylmethylthio-2-chloromethylpyridine,

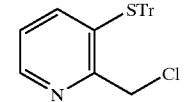

3-triphenylmethylthio-2-chloromethylpyridine hydrochloride,

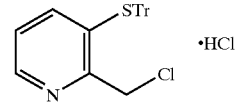

3-triphenylmethylthio-2-[2-N-(t-butoxycarbonyl)aminoethylthiomethyl)]pyridine,

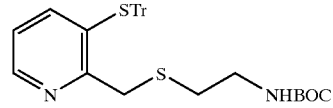

2-(2-aminoethylthiomethyl)-3-mercaptopyridine,

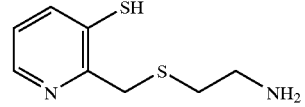

bis(2-(2-aminoethylthiomethyl)pyrid-3-yl)disulfide,

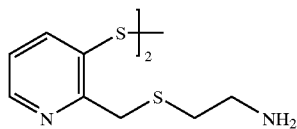

and the compound of the following formula:

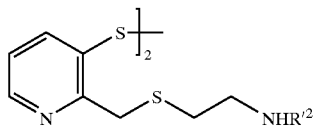

where R'² is as defined herein.

In another aspect, the invention relates to a compound selected from the group consisting of 7-amino-3-chloro-3-cephem-4-carboxylate, t-butyl ester,

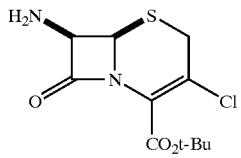

(7R)-7-[(Z)-2-(5-amino-1,2,4-thiadiazol-3-yl)-2-(triphenylmethoxyimino)acetamido-3-chloro-3-cephem-4-carboxylate, t-butyl ester,

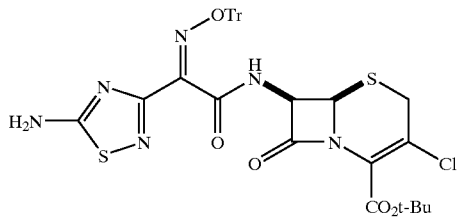

and the compound of the following formula:

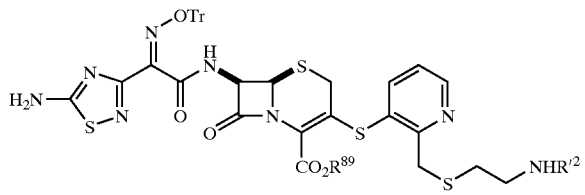

where R'² and R⁸⁹ are as defined herein.

In a further aspect, the invention relates to a method of synthesizing a compound of formula VI

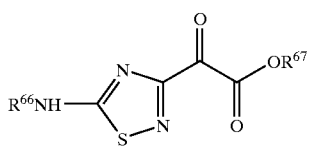

(VI)

comprising reacting a compound of formula VII with an amine-N-oxide,

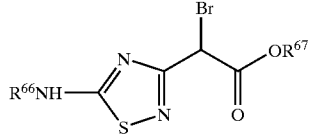

(VII)

where:
R⁶⁶ is selected from the group comprising of hydrogen, alkyl, benzyl, —C(O)—R⁶⁸,
where R⁶⁸ is selected from the group consisting of hydrogen, alkyl, aryl, alkoxyl, and aryloxy;
R⁶⁷ is alkyl or benzyl; and
the amine-N-oxide is selected from the group consisting of trialkylamine-N-oxide and pyridine-N-oxide.

Preferably, R⁶⁶ is benzyl or —C(O)—OCH₂CH₃; R⁶⁷ is methyl or benzyl; and the amine-N-oxide is selected from the group consisting of trimethylamine-N-oxide, N-methylmorpholine-N-oxide, and pyridine-N-oxide.

In another aspect, the invention relates to a compound of formula VIII

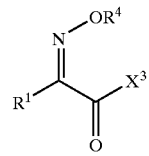

(VIII)

where
R¹ is selected from the group consisting of optionally substituted aryl and optionally substituted heterocycle, where the heterocycle is selected from the group consisting of pyridyl, thiadiazolyl, and thiazolyl; and
where the aryl and heterocycle are each independently and optionally substituted with substituents selected from the group consisting of hydroxyl, bromo, fluoro, chloro, iodo, mercapto, cyano, alkylthio, carboxyl, oxo, alkoxycarbonyl, alkyl, alkenyl, nitro, amino, alkoxyl, and carboxamido;
R⁴ is a protecting group selected from the group consisting of benzyl, p-nitrobenzyl, o-nitrobenzyl, 2,2,2-trichloroethyl, allyl, cinnamyl, benzhydryl, 2-chloroallyl, t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4- or 2-methoxybenzyl, 2,4-dimethoxybenzyl, 3,4-dimethoxybenzyl, 2,4,6-trimethoxybenzyl, methoxymethyl, benzhydryl, and 3,3-dimethylallyl; and
X³ is selected from the group consisting of —OP(O)—(O-phenyl)₂, and —OP(O)—Cl₂.

Preferably, R¹ is 5-amino-1,2,4-thiadiazol-3-yl and R⁴ is trityl.

The summary of the invention described above is non-limiting and other features and advantages of the invention will be apparent from the following description of the preferred embodiments, and from the claims.

DETAILED DESCRIPTION OF THE PREFERRED EMBODIMENTS

I. Definitions

As used herein, the term "alkyl" denotes a branched, unbranched, or cyclic hydrocarbon group, preferably containing between one and six, more preferably one and four, carbon atoms, such as methyl, ethyl, n-propyl, iso-propyl, n-butyl, sec-butyl, iso-butyl, tert-butyl, and 2-methylpentyl. These groups may be optionally substituted with one or more functional groups which are attached commonly to such chains, such as hydroxyl, bromo, fluoro, chloro, iodo, mercapto, cyano, alkylthio, heterocycle, aryl, heteroaryl, carboxyl, alkoxycarbonyl, alkyl, alkenyl, nitro, amino, alkoxyl, amido, and optionally substituted isothioureido, amidino, guanidino, and the like to form alkyl groups such as trifluoromethyl, 3-hydroxyhexyl, 2-carboxypropyl, 2-fluoroethyl, carboxymethyl, 4-cyanobutyl, 2-guanidinoethyl, 3-N,N'-dimethylisothiouroniumpropyl, and the like.

The term "alkylene" refers to a straight chain or branched chain of carbon atoms, all bearing hydrogen atoms so that there are no unsaturated carbon atoms in the chain, where the chain is substituted with a chemical group other than hydrogen at two ends. Thus, the —$CH_2$— group (known as methylene), the —$CH_2CH_2$— group (known as ethylene), the, —$CH_2CH_2CH_2$— group (known as propylene), and —$CH_2CH(CH_3)CH_2$— (known as isopropylene) are examples without limitation of alkylene groups.

The term "alkenyl" denotes an alkyl group as defined above having at least one double bond, e.g., allyl, 3-hydroxy-2-buten-1-yl, 1-methyl-2-propen-1-yl and the like.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as, hydroxyl, bromo, fluoro, chloro, iodo, mercapto, cyano, alkylthio, heterocycle, aryl, heteroaryl, carboxyl, alkoxycarbonyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, cyanophenyl, pyridylphenyl, pyrrolylphenyl, pyrazolylphenyl, triazolylphenyl, tetrazolylphenyl and the like.

The term "heterocycle" denotes a chain of carbon and at least one non-carbon atoms which together form one or more aromatic or non-aromatic rings having preferably between about 5–14 atoms, such as, furyl, thienyl, imidazolyl, indolyl, pyridyl, thiadiazolyl, thiazolyl, piperazinyl, dibenzfuranyl, dibenzthienyl. These rings may be optionally substituted with one or more functional groups which are attached commonly to such rings, such as, hydroxyl, bromo, fluoro, chloro, iodo, mercapto or thio, cyano, alkylthio, heterocycle, aryl, heteroaryl, carboxyl, oxo, alkoxycarbonyl, alkyl, alkenyl, nitro, amino, alkoxyl, amido, and the like to form rings such as, 2-aminothiazol-4-yl, 2-amino-5-chlorothiazol-4-yl, 5-amino-1,2,4-thiadiazol-3-yl, 2,3-dioxopiperazinyl, 4-alkylpiperazinyl, 2-iodo-3-dibenzfuranyl and 3-hydroxy-4-dibenzthienyl and the like.

The term "heteroaromatic" or "heteroaryl" (HetAr) denotes an aromatic heterocycle as defined above.

The term "heterotricycle" denotes an aromatic heterocyclic substituent as defined above which comprises three aromatic rings.

The term "heterocyclecarbonyl" denotes the group —C(O)Het, where Het is heterocycle as defined above.

The term "alkoxyl" denotes the group —OR, where R is alkyl as defined above, such as methoxy, ethoxy, n-propoxy, iso-propoxy, n-butoxy, sec-butoxy, iso-butoxy, tert-butoxy, trifluoromethoxy, 3-hydroxyhexyloxy, 2-carboxypropyloxy, 2-fluoroethoxy, carboxymethoxy and cyanobutyloxy and the like.

The term "alkylthio" denotes the group —SR, where R is alkyl as defined above, such as methylthio, ethylthio, n-propylthio, iso-propylthio, n-butylthio, sec-butylthio, iso-butylthio, tert-butylthio, trifluoromethythio, 3-hydroxyhexylthio, 2-carboxypropylthio, 2-fluoroethylthio, carboxymethylthio and cyanobutylthio and the like.

The term "acyl" denotes groups —C(O)R, where R is hydrogen or alkyl as defined above, such as formyl, acetyl, propionyl, or butyryl.

The term "aryloxy" denotes groups —OAr, where Ar is an aryl group as defined above.

The term "aralkyl" denotes groups —RAr, where R is alkyl and Ar is aryl, both as defined above. The term encompasses groups where the R group is substituted with one or more aryl groups. Examples of aralkyl groups include, but are not limited to, benzyl, diphenylmethyl, and triphenylmethyl.

The term "heteroaralkyl" denotes groups —RHetAr where R is alkylene as defined above and HetAr is heteroaryl as defined above.

The term "trialkylsilyl" denotes the group RR'R"Si—, where R, R' and R" are alkyl as defined above.

The term "trialkylammonium" denotes the group [RR'R"N—]$^+$, where R, R' and R" are alkyl as defined above.

The term "amino" denotes the group NRR', where R and R' may independently be alkyl, aryl or acyl as defined above, or hydrogen.

The term "carboxamido" denotes the group —C(O)NRR', where R and R' may independently be alkyl, aryl or acyl as defined above, or hydrogen.

The term "β-lactam resistant bacteria" refers to bacteria against which a β-lactam antibiotic has a minimum inhibitory concentration (MIC) of greater than 32 mg/mL.

The term "methicillin-resistant bacteria" refers to bacteria that are resistant to methicillin. Examples of such bacteria are provided in Table 1 and are identified Meth$^R$. The term "methicillin sensitive bacteria" refers to bacteria that are sensitive to methicillin. Examples of such bacteria are provided in Table 1 and are identified Meth$^S$.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial. A further example of a prodrug might be a short peptide (polyaminoacid) bonded to an acid group where the peptide is metabolized to reveal the active moiety.

II. Compounds of the Invention

The present invention provides compounds, methods and compositions effective to treat bacterial infections, and, especially, infections arising from bacteria which have developed resistance to conventional β-lactam antibiotics. The present invention also provides compounds, methods and compositions effective to treat bacterial infections arising from bacteria which have developed resistance to conventional cephalosporin antibiotics.

It is understood to those skilled in the art that the compounds of the present invention can be prepared or be present as their pharmaceutically acceptable salts or as salts that may not be pharmaceutically acceptable. Such salts are within the scope and contemplation of the claims of the present invention. Such salts can exist as the combination of the compounds of the present invention and acids or bases. These acids may include trifluoroacetic acid, hydrochloric acid, methanesulfonic acid, and other organic or inorganic acids. The bases may include benzathene, chloroprocaine, choline, diethanolamine, ethylenediamine, meglumine, procain, and the hydroxide, alkoxide, carbonate, bicarbonate, sulfate, bisulfate, amide, alkylamide, or dialkylamide salts of the following metal cations: lithium, sodium, potassium, magnesium, calcium, aluminum, and zinc and other organic or inorganic bases. These salts may exist as a combination of one or more equivalents of acid or base per compound or one or more equivalents of compound per acid or base.

The names and structures of some of the compounds of the invention are shown below.

Cmpd 1 (7R)-7-[(Z)-2-(2-amino-5-chlorothiazol-4-yl)-2-(hydroxyimino)acetamido]-3-(2-aminoethylthio-1,3,4-thiadiazol-5-ylthio)-3-cephem-4-carboxylic acid

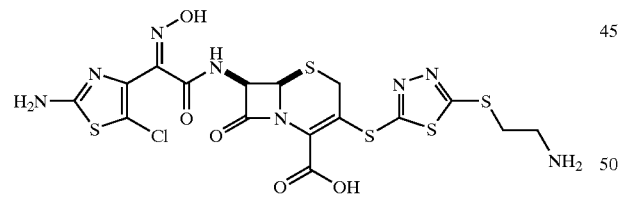

Cmpd 2 (7R)-7-[(Z)-2-(2-aminopyrid-6-yl)-2-(hydroxyimino)acetamido]-3-[4-(2-aminoethylthiomethyl)-2-methyl-1,3-thiazol-5-ylthio]-3-cephem-4-carboxylic acid

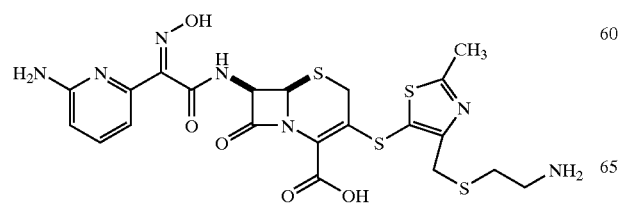

Cmpd 3 (7R)-7-[(Z)-2-(2-amino-5-chlorothiazol-4-yl)-2-(hydroxyimino)acetamido]-3-[4-(2-aminoethylthiomethyl)-2-amino-1,3-thiazol-5-ylthio]-3-cephem-4-carboxylic acid

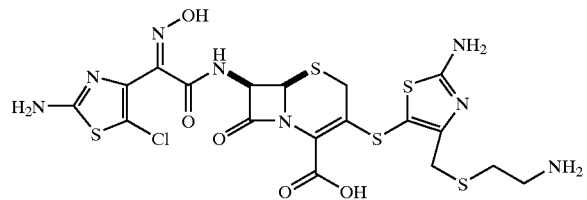

Cmpd 4 (7R)-7-[(Z)-2-(2-aminopyrid-6-yl)-2-(hydroxyimino)acetamido]-3-[4-(2-aminoethylthiomethyl)-1,3-thiazol-2-ylthio]-3-cephem-4-carboxylic acid

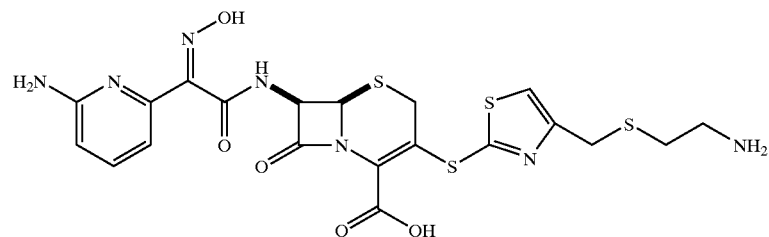

Cmpd 5 (7R)-7-[(Z)-2-(2-aminopyrid-6-yl)-2-(hydroxyimino)acetamido]-3-[4-(2-aminoethylthiomethyl)-2-methoxy-1,3-thiazol-5-ylthio]-3-cephem-4-carboxylic acid

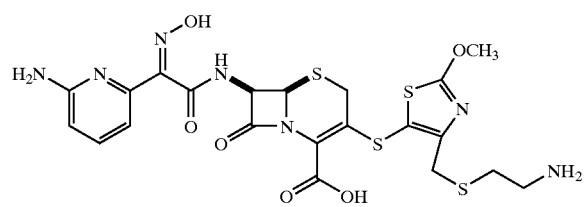

Cmpd 6 (7R)-7-[(Z)-2-(2-aminopyrid-6-yl)-2-(hydroxyimino)acetamido]-3-[2-(2-aminoethylthio)-pyridazin-6-ylthio]-3-cephem-4-carboxylic acid

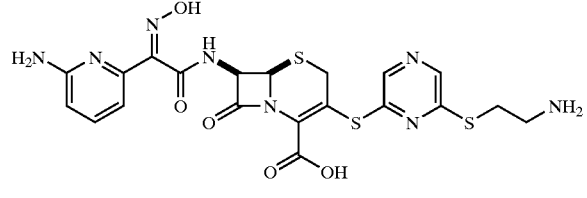

Cmpd 7 (7R)-7-[(Z)-2-(2-aminopyrid-6-yl)-2-(hydroxy-imino)acetamido]-3-[2-(2-aminoethylthio)-pyridazin-3-ylthio]-3-cephem-4-carboxylic acid

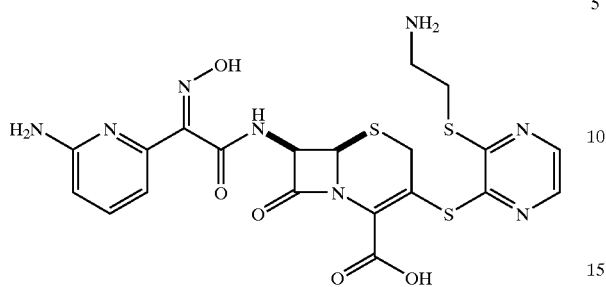

Cmpd 8 (7R)-7-[(Z)-2-(2-aminopyrid-6-yl)-2-(hydroxy-imino)acetamido]-3-[2-(2-aminoethylthio)-pyrimidin-4-ylthio]-3-cephem-4-carboxylic acid

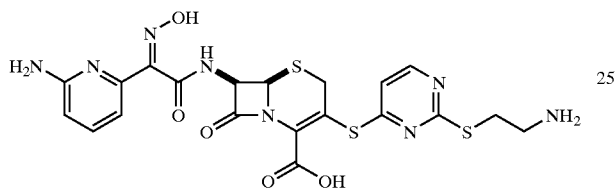

Cmpd 9 (7R)-7-[(Z)-2-(2-aminothiazol-4-yl)-2-(hydroxy-imino)acetamido]-3-[2-(2-aminoethylthiomethyl)-pyridazin-3-ylthio]-3-cephem-4-carboxylic acid

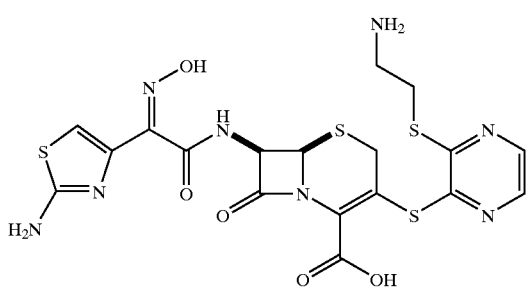

Cmpd 10 (7R)-7-[(Z)-2-(2-amino-5-chlorothiazol-4-yl)-2-(hydroxyimino)acetamido]-3-(2-aminoethylthio-methyl-1,3,4-thiadiazol-5-ylthio)-3-cephem-4-carboxylic acid

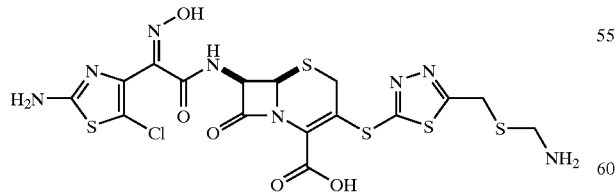

Cmpd 11 (7R)-7-[(Z)-2-(2-amino-5-chlorothiazol-4-yl)-2-(hydroxyimino)acetamido]-3-[4-(2-aminoethylthio-methyl)-2-aminoethylthio-1,3-thiazol-5-ylthio]-3-cephem-4-carboxylic acid

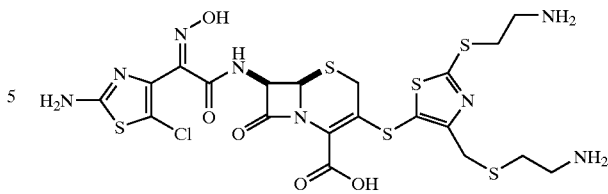

Cmpd 12 (7R)-7-[(Z)-2-(2-amino-5-chlorothiazol-4-yl)-2-(hydroxyimino)acetamido]-3-[3-(2-aminoethylthio-methyl)-1,2,4-thiadiazol-5-ylthio]-3-cephem-4-carboxylic acid

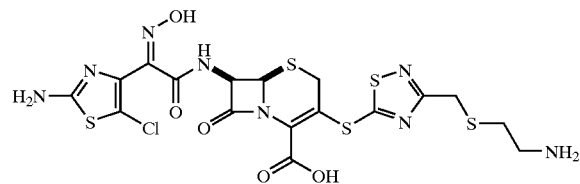

Cmpd 13 (7R)-7-[(Z)-2-(2-amino-5-chlorothiazol-4-yl)-2-(hydroxyimino)acetamido]-3-[2-(2-aminoethylthio-methyl)pyrid-3-ylthio]-3-cephem-4-carboxylic acid

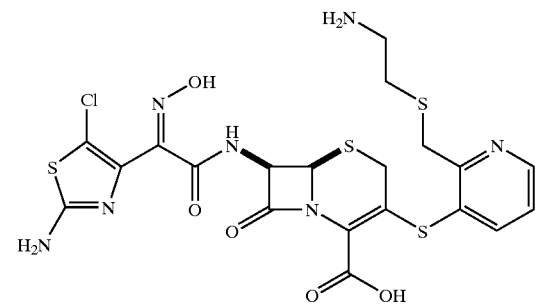

Cmpd 14 (7R)-7-[(Z)-2-(5-amino-1,2,4-thiadiazol-3-yl)-2-(hydroxyimino)acetamido]-3-[2-(2-guanidinoethyl-thiomethyl)pyrid-3-ylthio]-3-cephem-4-carboxylic acid

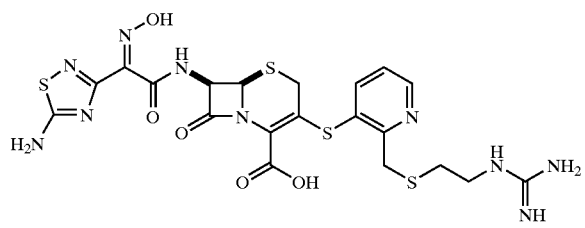

Cmpd 15 (7R)-7-[(Z)-2-(2-amino-5-chlorothiazol-4-yl)-2-(hydroxyimino)acetamido]-3-[2-(2-guanidinoethyl-thiomethyl)pyrid-3-ylthio]-3-cephem-4-carboxylic acid

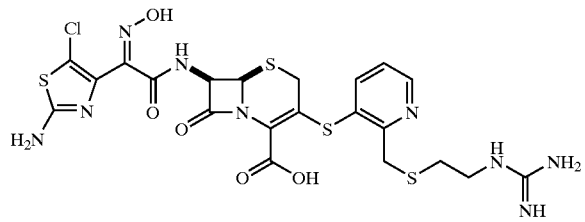

Cmpd 16 (7R)-7-[(Z)-2-(2-amino-5-chlorothiazol-4-yl)-2-(hydroxyimino)acetamido]-3-[4-(2-aminoethylthiomethyl)-2-aminoethylamino-1,3-thiazol-5-ylthio]-3-cephem-4-carboxylic acid Cmpd 19 (7R)-7-[(Z)-2-(5-aminothiazol-4-yl)-2-(hydroxyimino)acetamido]-3-[3-(2-aminoethylthiomethyl)pyrid-4-ylthio]-3-cephem-4-carboxylic acid

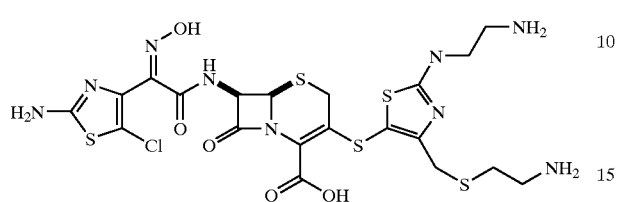

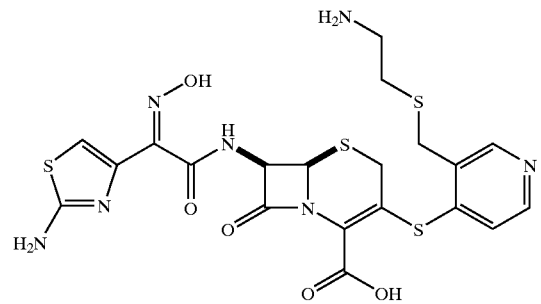

Cmpd 17 (7R)-7-[(Z)-2-(5-amino-1,2,4-thiadiazol-3-yl)-2-(hydroxyimino)acetamido]-3-[2-(2-aminoethylthiomethyl)pyrid-3-ylthio]-3-cephem-4-carboxylic acid Cmpd 20 (7R)-7-[(Z)-2-(2-amino-5-chlorothiazol-4-yl)-2-(hydroxyimino)acetamido]-3-[3-(2-aminoethylthiomethyl)pyrid-4-ylthio]-3-cephem-4-carboxylic acid

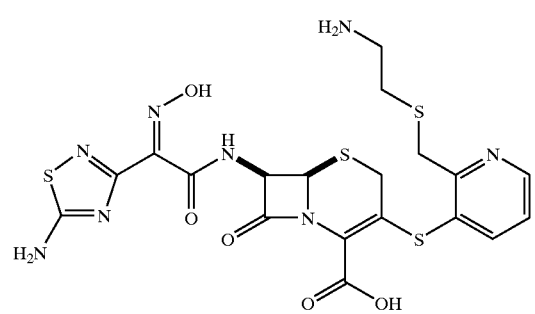

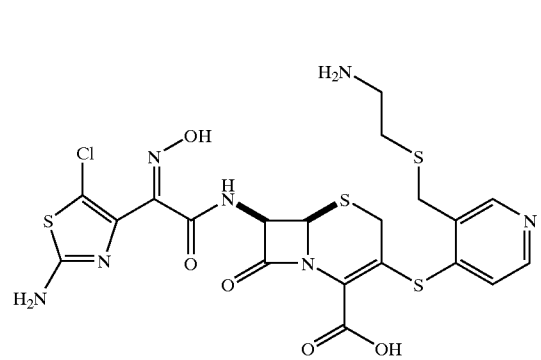

Cmpd 18 (7R)-7-[(Z)-2-(5-amino-1,2,4-thiadiazol-3-yl)-2-(hydroxyimino)acetamido]-3-[3-(2-aminoethylthiomethyl)pyrid-4-ylthio]-3-cephem-4-carboxylic acid Cmpd 21 (7R)-7-[(Z)-2-(2-amino-5-chlorothiazol-4-yl)-2-(hydroxyimino)acetamido]-3-[4-(2-aminoethylthiomethyl)pyrid-3-ylthio]-3-cephem-4-carboxylic acid

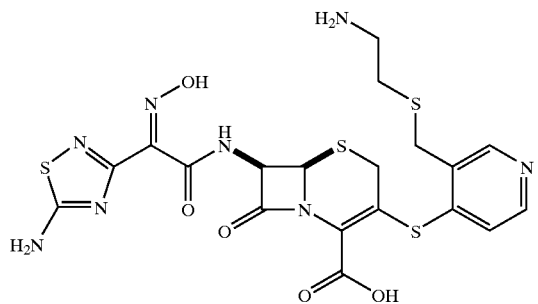

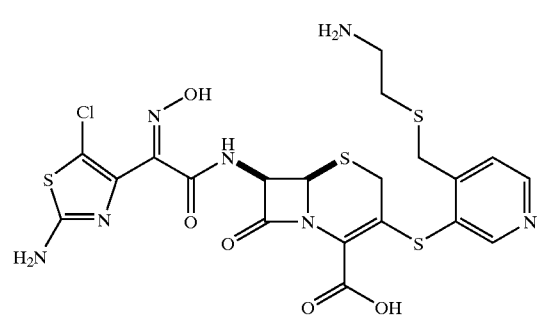

Cmpd 22 (7R)-7-[(Z)-2-(2-aminopyrid-6-yl)-2-(hydroxyimino)acetamido]-3-(2-aminoethylthio-1,3,4-thiadiazol-5-ylthio)-3-cephem-4-carboxylic acid Cmpd 25 (7R)-7-[(Z)-2-(5-amino-1,2,4-thiadiazol-3-yl)-2-(hydroxyimino)acetamido]-3-[3-(2-guanidinoethyl-thiomethyl)pyrid-4-ylthio]-3-cephem-4-carboxylic acid

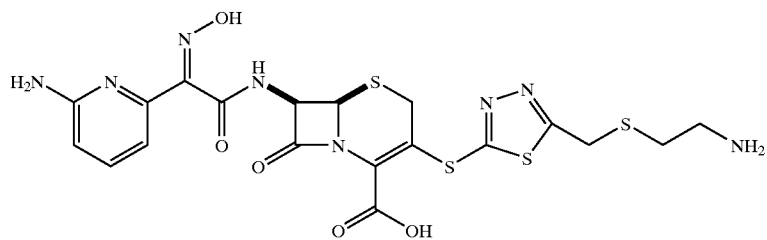

Cmpd 23 (7R)-7-[(Z)-2-(2-aminopyrid-6-yl)-2-(hydroxyimino)acetamido]-3-[4-(2-aminoethylthiomethyl)-1,3-thiazol-5-ylthio]-3-cephem-4-carboxylic acid

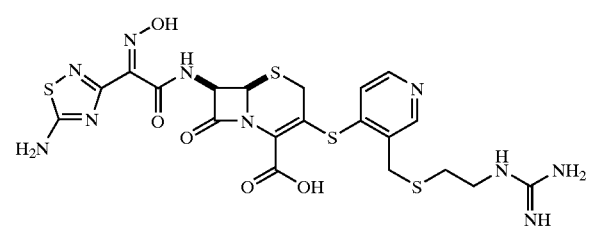

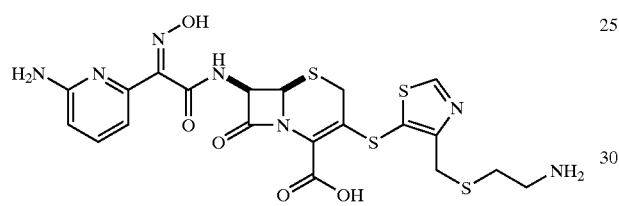

Cmpd 26 (7R)-7-[(Z)-2-(2-amino-5-chlorothiazol-4-yl)-2-(hydroxyimino)acetamido]-3-[4-(2-guanidinoethyl-thiomethyl)-2-amino-1,3-thiazol-5-ylthio]-3-cephem-4-carboxylic acid

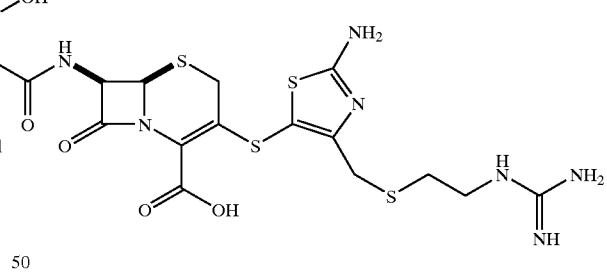

Cmpd 24 (7R)-7-[(Z)-2-(2-aminopyrid-6-yl)-2-(hydroxyimino)acetamido]-3-[3-(2-aminoethylthiomethyl)pyrid-4-ylthio]-3-cephem-4-carboxylic acid Cmpd 27 (7R)-7-[(Z)-2-(5-amino-1,2,4-thiadiazol-3-yl)-2-(hydroxyimino)acetamido]-3-[4-(2-aminoethylthiomethyl)pyrid-3-ylthio]-3-cephem-4-carboxylic acid

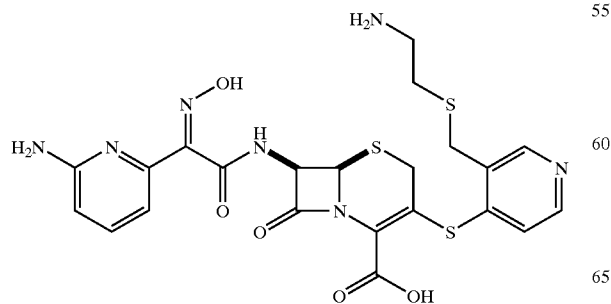
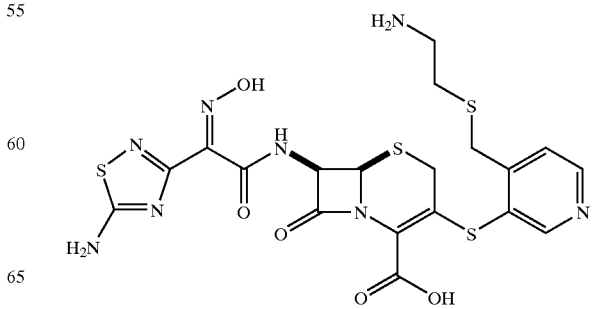

Cmpd 28 (7R)-7-[(Z)-2-(2-aminopyrid-6-yl)-2-(hydroxy-imino)acetamido]-3-[4-(2-aminoethylthiomethyl)pyrid-3-ylthio]-3-cephem-4-carboxylic acid

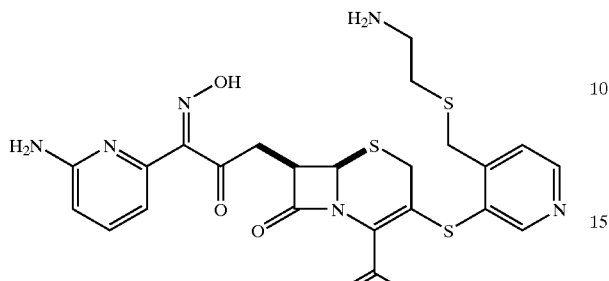

Cmpd 29 (7R)-7-[(Z)-2-(2-aminopyrid-6-yl)-2-(hydroxyimino)acetamido]-3-[2-chloro-4-(2-aminoethylthiomethyl)-1,3-thiazol-5-ylthio]-3-cephem-4-carboxylic acid

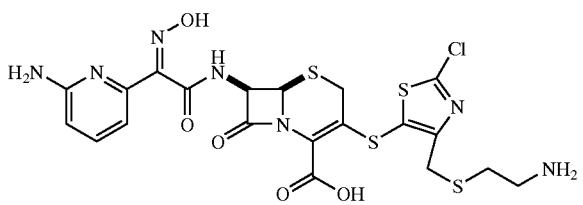

A. Synthesis of Compounds of Formula I and II

The compounds of the present invention may be readily prepared in accordance with the following schemes. However, it will be appreciated that other synthetic pathways for forming the compounds of the invention are available and that the following is offered merely by way of example, and not limitation. It will be further recognized that various protecting and deprotecting strategies will be employed which are standard in the art (see, e.g., Greene and Wuts, Protective Groups in Organic Synthesis, 2$^{nd}$ Ed., John Wiley & Sons, New York, N.Y., 1991). Those of skill in the art will recognize that the selection of any particular protecting group (e.g., a carboxyl protecting group) will depend on the stability of the protected moiety with respect to subsequent reaction conditions.

Generally, the synthesis of the cephalosporins of the present invention may be achieved using well-known methods and readily available materials (see, e.g., March; Larock, COMPREHENSIVE ORGANIC TRANSFORMATIONS (VCH Publishers, 1989); and G. I. Georg, THE ORGANIC CHEMISTRY OF β-LACTAMS, (VCH 1992), each of which is incorporated herein by reference).

Cephalosporin intermediates bearing an appropriate acylamino substituent $R^1$ and carboxyl protecting group $R^2$ and leaving group $R^{"1}$ can be reacted with a heterocyclic thiol, displacing $R^{"1}$.

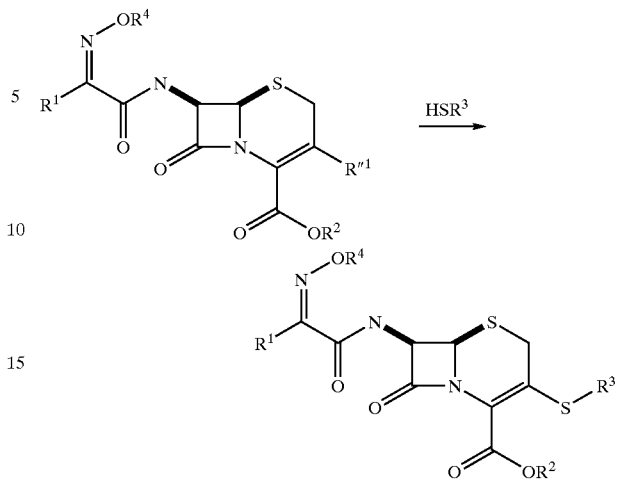

In the above structures, $R^{"1}$ is a leaving group, which may be selected from the group consisting of p-toluenesulfonate, methylsulfonate, fluorosulfonate, chloro, bromo, and $(R^{"2}O)_2PO-$, where $R^{"2}$ is selected from the group consisting of hydrogen and alkyl, as defined herein; and $R^2$ is a carboxyl protecting group, which may be selected from the group consisting of p-methoxybenzyl, benzhydryl, t-butyl, allyl, and p-nitrobenzyl. Those skilled in the art realize that other suitable leaving groups or carboxyl protecting groups may be used in place of those mentioned here for $R^{"1}$ and $R^2$, respectively. For example, the carboxyl protecting group $R^2$ may be those protecting groups amenable to reductive cleavage, such as benzyl, p- or o-nitrobenzyl, 2,2,2-trichloroethyl, allyl, cinnamyl, benzhydryl, 2-chloroallyl and the like. Alternatively, $R^2$ may be a protecting group amenable to acidic cleavage, such as t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4- or 2-methoxybenzyl, 2,4-dimethoxybenzyl, 3,4-dimethoxybenzyl, 2,4,6-trimethoxybenzyl, methoxymethyl, benzhydryl, or 3,3-dimethylallyl. Preferred protecting groups are t-butyl, p-methoxybenzyl, p-nitrobenzyl, allyl and benzhydryl. Such groups may be attached to the unprotected carboxyl group of the cephalosporin starting material using known reagents and techniques, such as those described in Greene and Wuts.

The above reaction may be carried out at room temperature, at temperatures higher than room temperature, or at temperatures lower than room temperature. The reaction is preferably carried out in the range of about −78° C. to about 50° C., more preferably in the range of about −10° C. to about 40° C., and most preferably in the range of about 0° C. to room temperature. "Room temperature" is generally in the range of about 20° C. to about 25° C. By "about" a certain temperature it is meant that the temperature range is preferably within 10° C. of the listed temperature, more preferably within 5° C. of the listed temperature, and most preferably within 2° C. of the listed temperature. Therefore, by way of example, by "about 40° C." it is meant that the temperature range is preferably 40±10° C., more preferably 40±5° C., and most preferably 40±2° C.

The reaction can also be carried out with or without an external base. If a base is used, the base is preferably a nitrogen base, an organic base, or an inorganic base. "Nitrogen bases" are commonly used in the art and are selected from acyclic and cyclic amines. Examples of nitrogen bases include, but are not limited to, ammonia, methylamine, trimethylamine, triethylamine, aniline, 1,8-diazabicyclo[5.4.0]undec-7-ene, diisopropylethylamine, pyrrolidine, piperidine, and pyridine or substituted pyridine (e.g., 2,6-di-tert-butylpyridine). "Organic bases" are bases that contain carbon atoms. Examples of organic bases include, but are not limited to, carbonate, bicarbonate, acetate, and formate anions. "Inorganic bases" are bases that do not contain any carbon atoms. Examples of inorganic bases include, but are not limited to, hydroxide, phosphate, bisulfate, hydrosulfide, and amide anions. Those skilled in the art know which nitrogen base or inorganic base would match the requirements of the reaction conditions. In certain embodiments of the invention, the base used may be pyrrolidine or piperidine. In other embodiments the base may be the hydroxide, carbonate, bicarbonate or anion, preferably used as the sodium or potassium salt.

The solvent in which the reaction is carried out may be a homogeneous solvent system, in which case no phase transfer catalyst is used. In other cases, the solvent may, be a heterogeneous solvent system, in which case a phase transfer catalyst is used. By "homogeneous solvent system" it is meant a solvent system which uses one or more solvents that are fully miscible, and therefore, form one phase. The solvents in a homogeneous solvent system are all other hydrophobic or hydrophilic. By "heterogeneous solvent system" it is meant a solvent system which uses two or more solvents that are not fully miscible, and therefore, form more than one phase, usually two phases consisting of an aqueous phase and an organic phase. Some of the solvents in a heterogeneous solvent system are hydrophobic while others are hydrophilic.

If a heterogeneous solvent system is used, then the reaction may be carried out in the presence of a phase transfer catalyst. Those skilled in the art can select a suitable phase transfer catalyst by knowing the reaction conditions or by further experimentation. Common phase transfer catalysts include, but are not limited to, quaternary ammonium salts.

Manipulation of the 7-acyl substituent can be performed after the thio-linked heterocyclic substituent is attached to the cephalosporin:

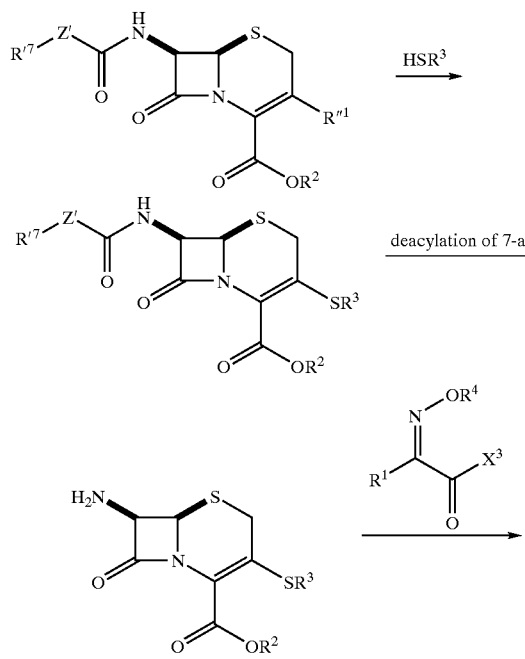

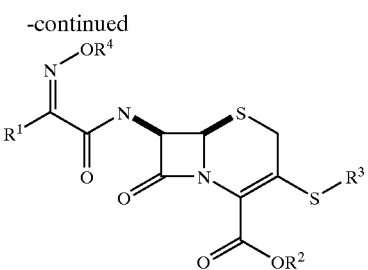

In the above scheme $R^1$, $R^2$, $R^3$, and $R^4$ are as defined herein. $R'^7$ is preferably selected from the group consisting of alkyl and aryl, as those terms are defined herein. $R'^7$ is more preferably selected from the group consisting of phenyl, tert-butyl, and benzyl. Z' is preferably selected from the group consisting of methylene (—$CH_2$—), oxygen, sulfur, and —NH—. More preferably, Z' is selected from the group consisting of methylene and oxygen. $X^3$ in the above scheme is preferably selected from the group consisting of —OP(O)—(O-phenyl)$_2$, and —OP(O)—$Cl_2$.

Alternatively, the displacement of the leaving group at the 3-position of cephalosporin can be performed at the stage of the 7-amino intermediate and then followed by acylation of the amine with appropriate acylating reagent:

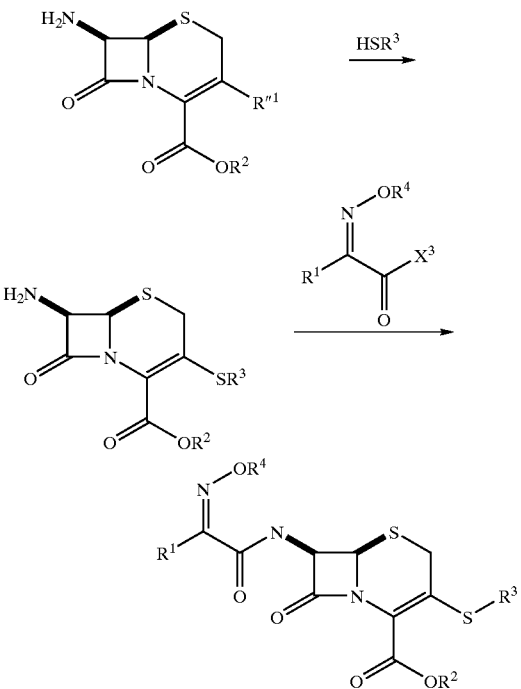

In the above scheme $R^1$, $R^2$, $R^3$, $R^4$, and $X^3$ are as defined herein.

Finally, the one-step or multi-step deprotection of the fully assembled cephalosporin, removing protecting group $R^2$, and other protecting groups present at substituents $R^3$, Z, and $R^7$ using conditions appropriate for the removal of all protecting groups is used for obtaining the biologically active cephalosporin.

The substituent $R^1$ in all of the above schemes may be any of the groups described above and are either available commercially (e.g., from Aldrich, Milwaukee, Wis.) or can be formed using known techniques and starting materials (see, e.g., March; Larock). These groups can be substituted for those present on the starting material by variety of well known techniques (see, e.g., Barrett, J. C. S. Perkin I, 1629 (1979) or Chauvette, *J. Org. Chem.* 36:1259 (1971), both of which are incorporated herein by reference), such as by transamination of an existing substituent for the desired substituent, or hydrolytic removal of the existing substituent followed by reaction with a suitably reactive form of desired substituent, such as an acyl chloride. Again, the appropriate reagents and techniques will be apparent to those of skill in the art.

B. Side Chain Synthesis

Side chains on C-7 and C-3 of the cephem core are synthesized by the procedures described below. These procedures are modified from the procedures found in chemical literature, in particular, Tatsuda, K. et al., *Bull. Chem. Soc. Jpn.*, 1994, 67, 1701–1707; Csendes, B. et al., *Journal of Antibiotics*, 1983, 36, 1020; Memoli, K. A., *Tetrahedron Lett*, 1996, 37, 3617; and Bjoork, P., et al., *J. Heterocyc. Chem*, 1995, 32 (3), 751.

The following diagrams depict the synthetic schemes for the side chains.

a. C-7 Side Chain Synthesis:

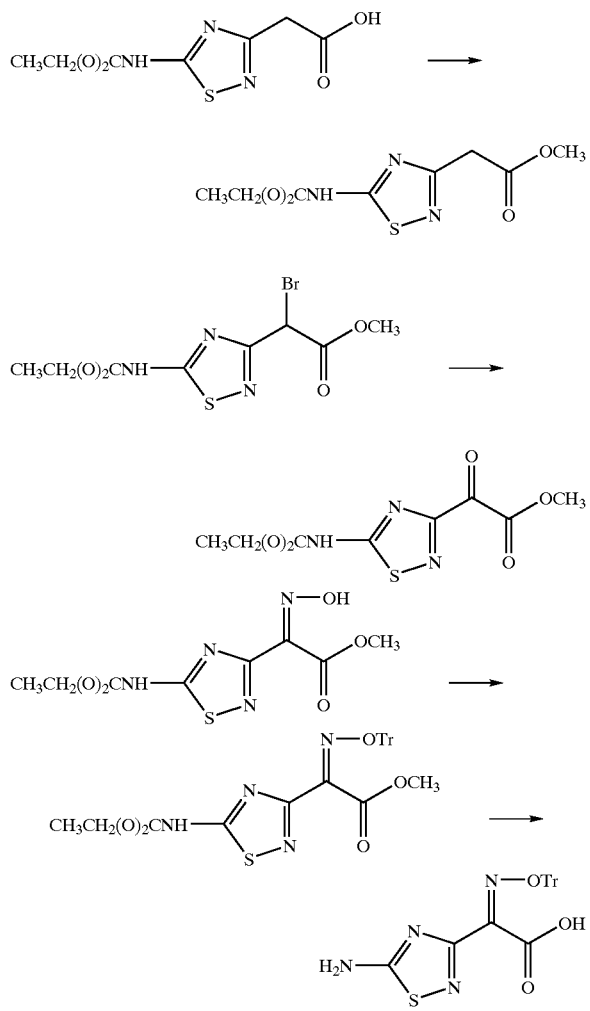

b. C-3 Side Chain Synthesis (Memoli, et al., Route):

As shown below, 3-mercapto-2-hydroxymethylpyridine is synthesized using the Memoli, et al., route.

The product of the above synthesis can be used to synthesize the C-3 side chains for the compounds of the present invention, using the synthetic schemes shown below.

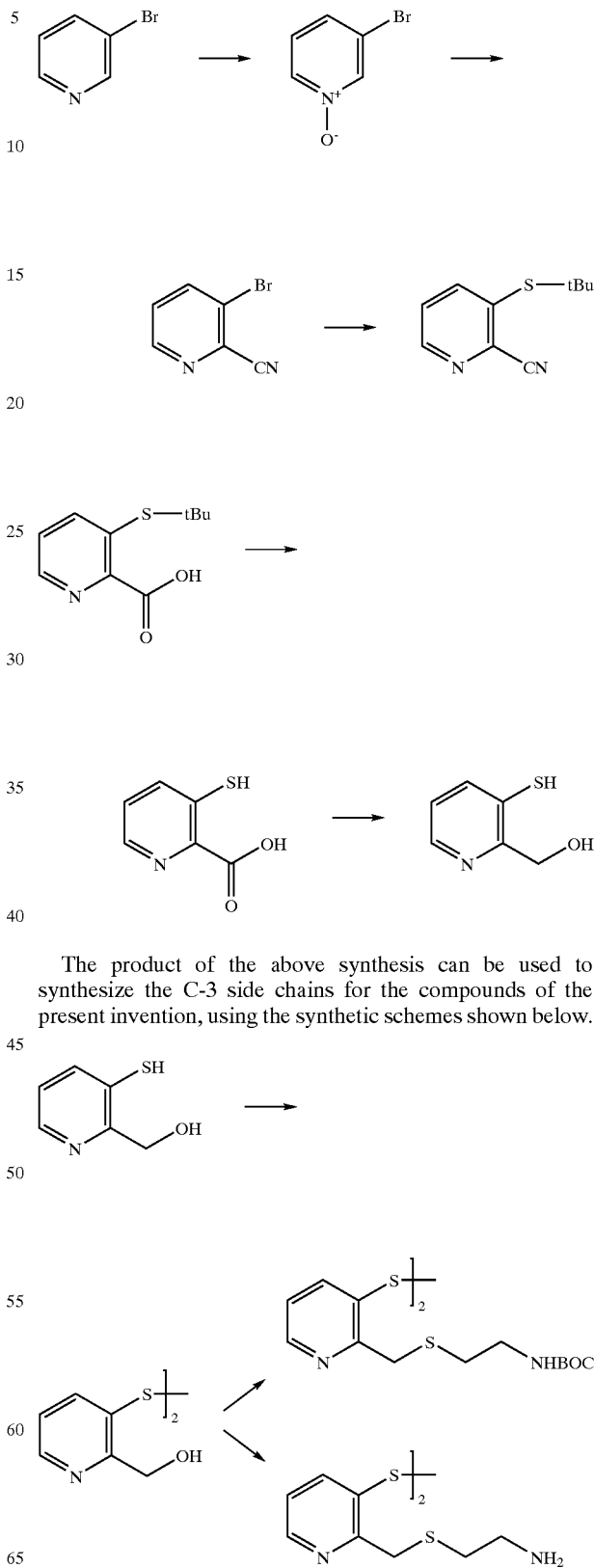

Or the following alternative pathway.

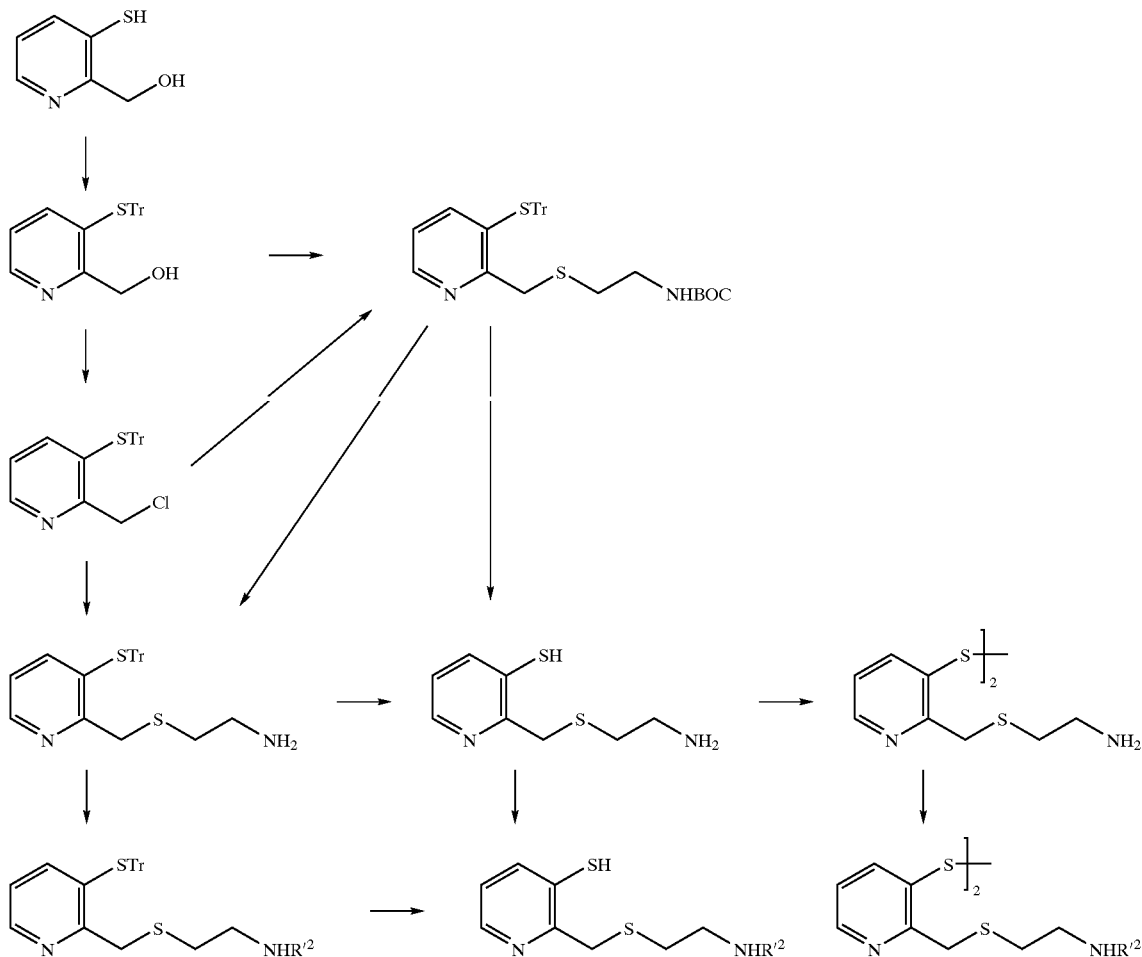

C. Other Synthetic Schemes

Some of the cephalosporin compounds of the invention can be synthesized using the scheme shown below.

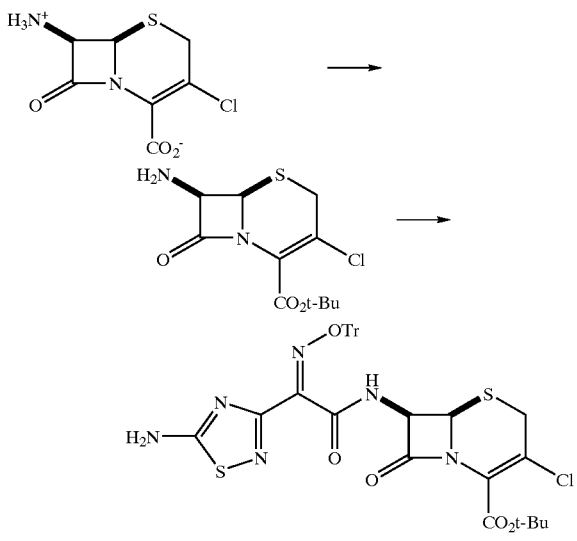

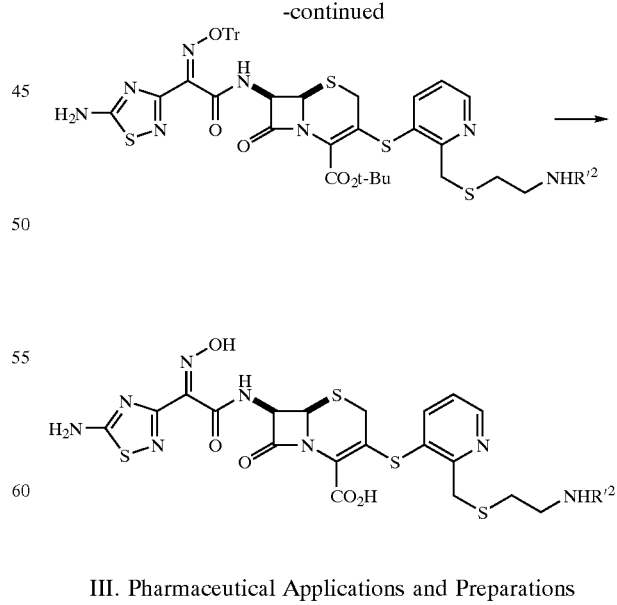

III. Pharmaceutical Applications and Preparations

According to this invention, a therapeutically or pharmaceutically effective amount of a cephalosporin and particularly, a compound of Formula I, II or III, is administered to a mammal suffering from a methicillin-resistant bacterial infection (or other β-lactam resistant bacterial infections, such as vancomycin-resistant or ampicillin-resistant infections), especially resistant *S. aureus*, in an amount effective to at least partially relieve the infection. Especially important are infections resulting from strains having similar activity to strains such as *S. aureus* Col (Meth$^R$)(lac$^-$), *S. aureus* 76 (Meth$^R$) (lac$^+$), *E. fœcium* ATCC 35667, or *E. fœcalis* ATCC 29212. Again, such compounds are also effective against bacteria sensitive to methicillin, vancomycin, and/or ampicillin and therefore have utility in such compositions and methods.

The compositions containing the compound(s) of the invention can be administered for prophylactic and/or therapeutic treatments. In therapeutic applications, the compositions are administered to a patient already suffering from an infection, as described above, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compound of the invention will be in the range of 0.1 to 1000 milligram (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between about one to four times per day.

While it is possible to administer the active ingredient of this invention alone, it is preferable to present it as part of a pharmaceutical formulation. The formulations of the present invention comprise at least one compound or inhibitor of this invention in a therapeutically or pharmaceutically effective dose together with one or more pharmaceutically or therapeutically acceptable carriers. Solid carriers include, e.g., starch, lactose, dicalcium phosphate, microcrystalline cellulose, sucrose and kaolin, and optionally other therapeutic ingredients. Liquid carriers include, e.g., sterile water, polyethylene glycols, non-ionic surfactants, and edible oils such as corn, peanut and sesame oils. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: The Pharmacological Basis of Therapeutics, 8th Ed., Pergamon Press; and Remington's supra. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. Generally, preferred routes of administration are intravenous and intraperitoneal.

These pharmacological agents can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Generally, a pharmacologically acceptable salt of the compound will be used to simplify preparation of the composition. Preferred salts include sodium, potassium, arginine, glycine, alanine, threonine, and lysine. These are prepared, preferably, in water suitably mixed with a surfactant such as hydroxypropylcellulose.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular subcutaneous, intramedullary injections, as well an intrathecal, direct intraventricular, intravenous, intraperitoneal, intranasal, or intraocular injections. just to name a few.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In soft capsules, the active compounds may be dissolved or suspended in suitable liquids, such as fatty oils, liquid paraffin, or liquid polyethylene glycols. In addition, stabilizers may be added.

IV. Prodrugs

Some of the compounds of the invention can be used as prodrugs. As explained above, a prodrug is an agent that is converted to the parent drug in vivo. The prodrugs of the present invention have the unusual and surprising characteristic of being more soluble than the parent compound at or near physiological pH. These prodrugs are converted to the parent compound in the body of the mammal that has received the prodrug. As can be seen from the structures of these prodrugs, a substituent either on C-5 of the thiadiazole group, or on C-2 of the pyridyl group can by cleaved by hydrolysis or enzymatic action in order to afford the parent compound. For instance, the amide group on the C-2 side chain of the pyridyl group of compounds 17-A, 17-B, 17-D -17-Q or the amide group on the C-5 side chain of the thiadiazole group of compound 17-C can be hydrolyzed and form an amine side chain, which is the parent compound 17.

The names and the structures of some of the prodrugs of the invention are shown below.

Cmpd 17-A (7R)-7-[(Z)-2-(5-amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic acid

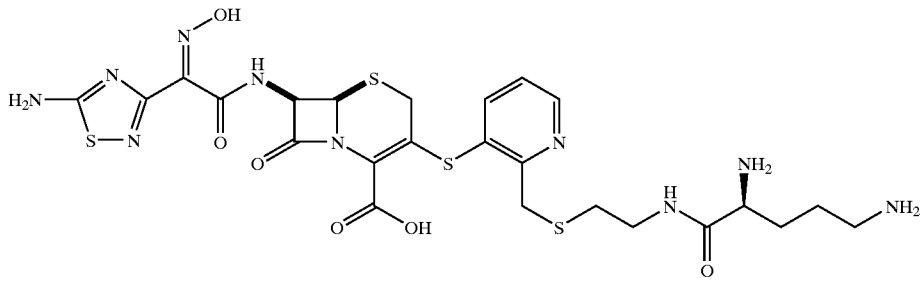

Cmpd 17-B (7R)-7-[(Z)-2-(5-amino-1,2,4-thiadiazol-3-yl)-2-(hydroxyimino)acetamido]-3-{2-[2-N-(L)-prolylaminoethylthiomethyl]pyrid-3-ylthio}-3-cephem-4-carboxylic acid

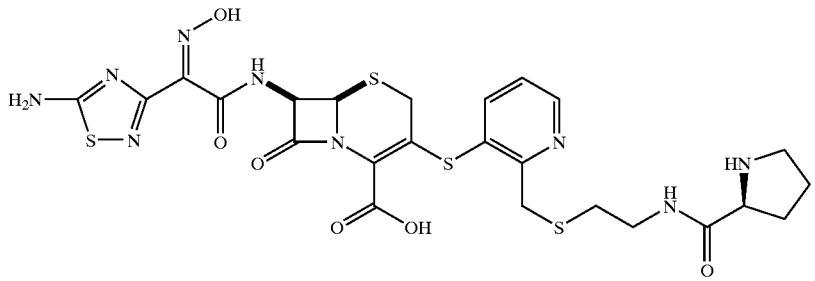

Cmpd 17-C (7R)-7-[(Z)-2-(5-N-(L)-alanylamino-1,2,4-thiadiazol-3-yl)-2-(hydroxyimino)acetamido]-3-{2-[2-aminoethylthiomethyl]pyrid-3-ylthio}-3-cephem-4-carboxylic acid

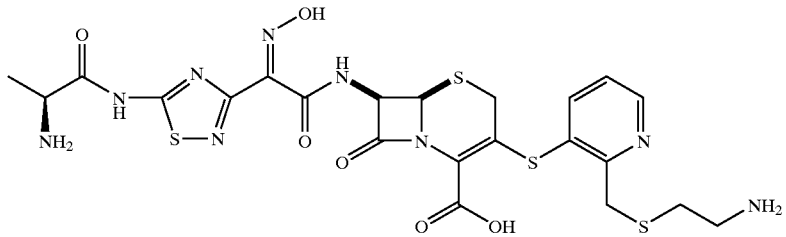

Cmpd 17-D (7R)-7-[(Z)-2-(5-amino-1,2,4-thiadiazol-3-yl)-2-(hydroxyimino)acetamido]-3-{2-[2-N-(L,L)-alanylalanylaminoethylthiomethyl]pyrid-3-ylthio}-3-cephem-4-carboxylic acid

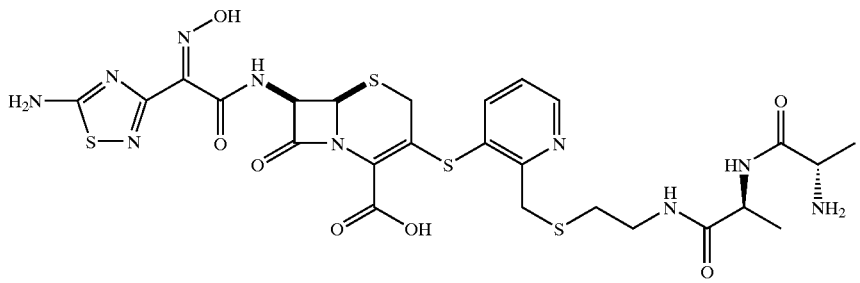

Cmpd 17-E (7R)-7-[(Z)-2-(5-amino-1,2,4-thiadiazol-3-yl)-2-(hydroxyimino)acetamido]-3-{2-[2-glycylaminoethylthiomethyl]pyrid-3-ylthio}-3-cephem-4-carboxylic acid

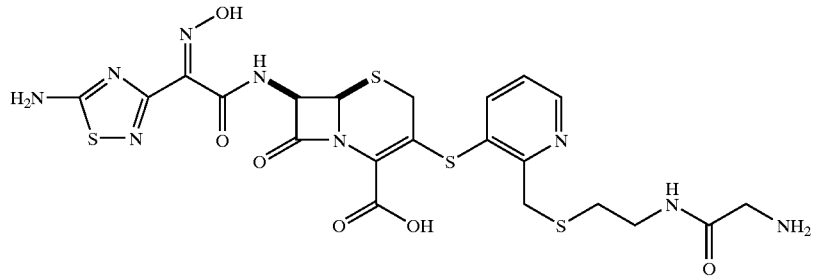

Cmpd 17-F (7R)-7-[(Z)-2-(5-amino-1,2,4-thiadiazol-3-yl)-2-(hydroxyimino)acetamido]-3-{2-[2-N-(L)-aspartylaminoethylthiomethyl]pyrid-3-ylthio}-3-cephem-4-carboxylic acid

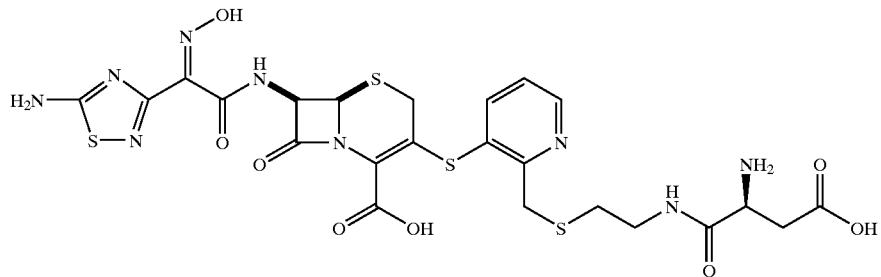

Cmpd 17-G (7R)-7-[(Z)-2-(5-amino-1,2,4-thiadiazol-3-yl)-2-(hydroxyimino)acetamido]-3-{2-[2-N-(L)-alanylaminoethylthiomethyl]pyrid-3-ylthio}-3-cephem-4-carboxylic acid

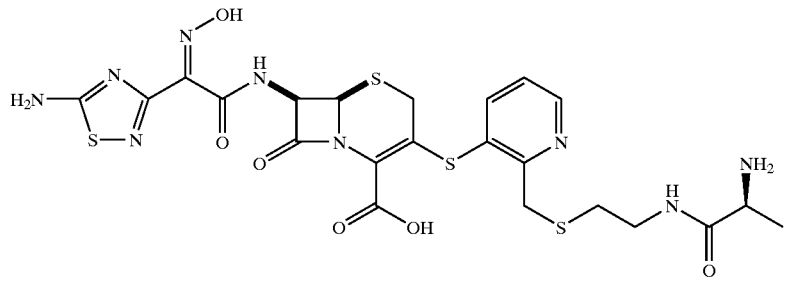

Cmpd 17-H (7R)-7-[(Z)-2-(5-amino-1,2,4-thiadiazol-3-yl)-2-(hydroxyimino)acetamido]-3-{2-[2-N-(L)-($N_\alpha$-methyl)alanylaminoethylthiomethyl]pyrid-3-ylthio}-3-cephem-4-carboxylic acid

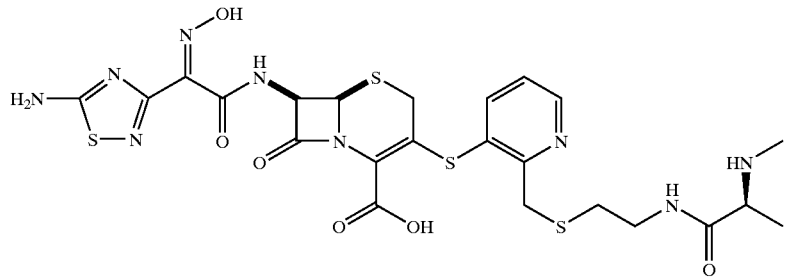

Cmpd 17-I (7R)-7-[(Z)-2-(5-amino-1,2,4-thiadiazol-3-y)-
2-(hydroxyimino)acetamido]-3-{2-[2-N-(L)-
histidylaminoethylthiomethyl]pyrid-3-ylthio}-3-
cephem-4-carboxylic acid

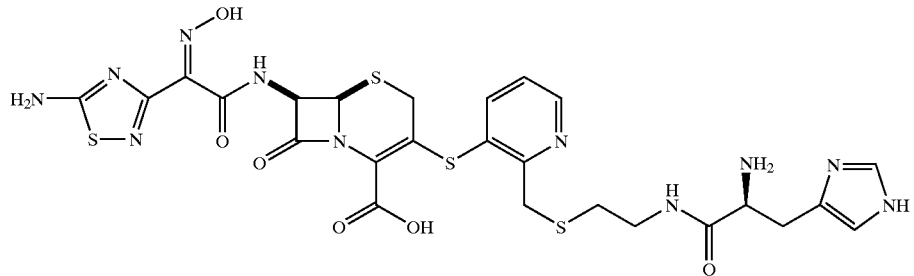

Cmpd 17-J (7R)-7-[(Z)-2-(5-amino-1,2,4-thiadiazol-3-
yl)-2-(hydroxyimino)acetamido]-3-{2-[2-N-(L)-
valylaminoethylthiomethyl]pyrid-3-ylthio}-3-cephem-
4-carboxylic acid

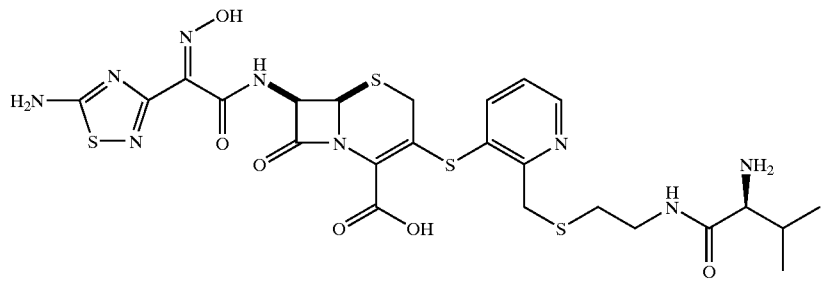

Cmpd 17-K (7R)-7-[(Z)-2-(5-amino-1,2,4-thiadiazol-3-
yl)-2-(hydroxyimino)acetamido]-3-{2-[2-N-(L)-
asparagylaminoethylthiomethyl]pyrid-3-ylthio}-3-
cephem-4-carboxylic acid

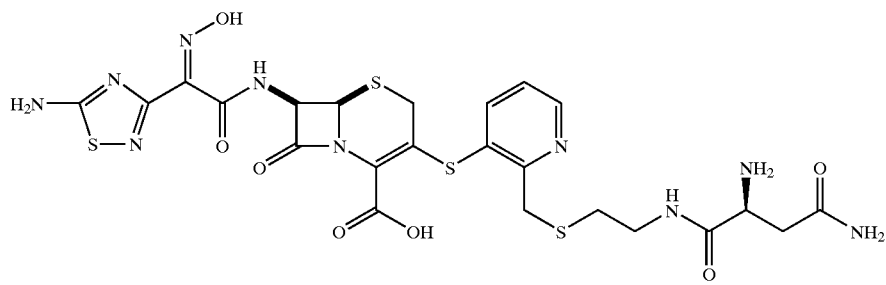

Cmpd 17-L (7R)-7-[(Z)-2-(5-amino-1,2,4-thiadiazol-3-
yl)-2-(hydroxyimino)acetamido]-3-{2-[2-N-(L)-
lysylaminoethylthiomethyl]pyrid-3-ylthio}-3-cephem-
4-carboxylic acid

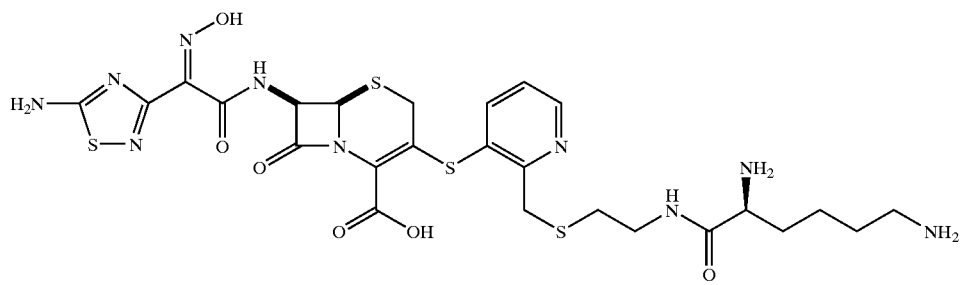

Cmpd 17-M (7R)-7-[(Z)-2-(5-amino-1,2,4-thiadiazol-3-yl)-2-(hydroxyimino)acetamido]-3-{2-[2-N-(L)-serylaminoethylthiomethyl]pyrid-3-ylthio}-3-cephem-4-carboxylic acid

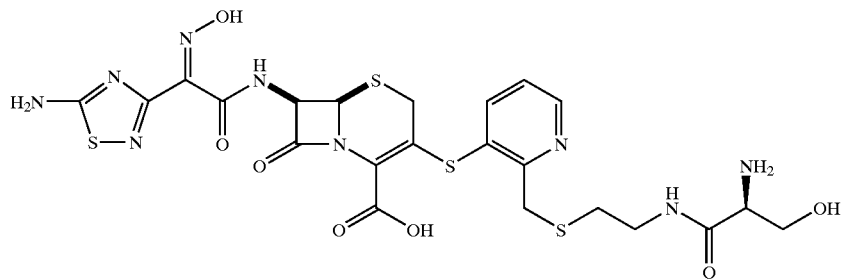

Cmpd 17-N (7R)-7-[(Z)-2-(5-amino-1,2,4-thiadiazol-3-yl)-2-(hydroxyimino)acetamido]-3-{2-[2-N-(L)-glutaminylaminoethylthiomethyl]pyrid-3-ylthio}-3-cephem-4-carboxylic acid

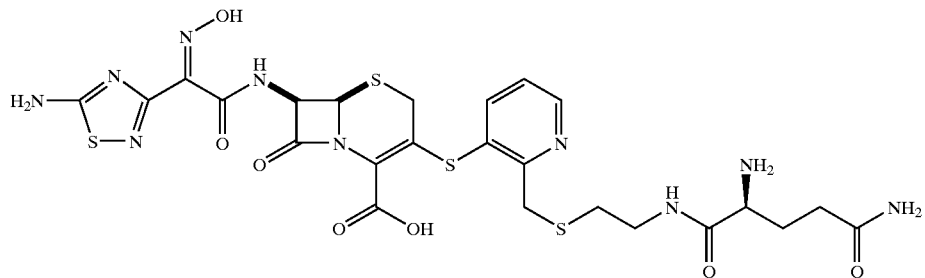

Cmpd 17-O (7R)-7-[(Z)-2-(5-amino-1,2,4-thiadiazol-3-yl)-2-(hydroxyimino)acetamido]-3-{2-[2-(5-methyl-1,3-dioxolan-4-en-2-on-4-yl)methoxycarbonyl)aminoethylthiomethyl]pyrid-3-ylthio}-3-cephem-4-carboxylic acid

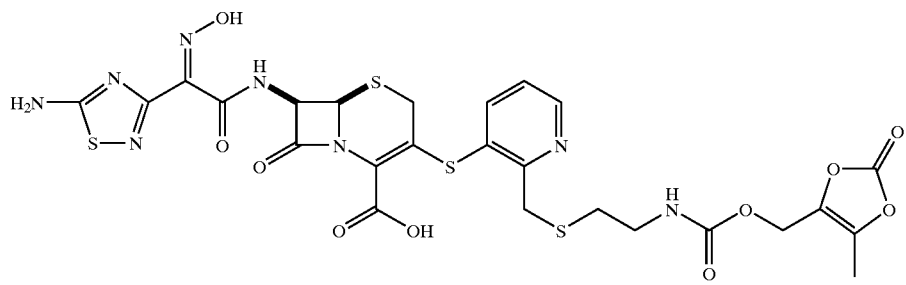

Cmpd 17-P (7R)-7-[(Z)-2-(5-amino-1,2,4-thiadiazol-3-yl)-2-(hydroxyimino)acetamido]-3-{2-(2-N-(L)-pyroglutamylaminoethylthiomethyl]pyrid-3-ylthio}-3-cephem-4-carboxylic acid

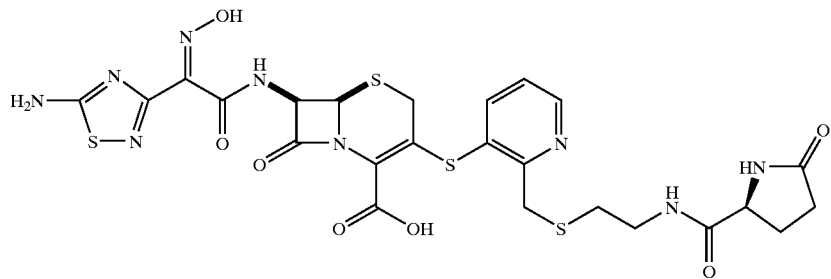

Thus, it will be appreciated that the compounds, methods and compositions of the invention are effective against various β-lactam resistant strains of bacteria which pose an increasing health risk to society.

EXAMPLES

The examples below are non-limiting and are merely representative of various aspects and features of the present invention. The examples describe methods for synthesizing compounds of the invention and various protocols.

Example 1
5-Acetylthio-4-acetylthiomethyl-2-methyl-1,3-thiazole

A mixture of L-serine (1.5 g, 14 mmol) and thiolacetic acid (12 mL) was stirred at 110° C. for 16 h in a sealed tube. The mixture became homogeneous. After cooling, the mixture was concentrated. The residue was partitioned between ethyl acetate and 5% aqueous sodium bicarbonate. The organic layer was concentrated and chromatographed (silica gel, dichloromethane), affording 600 mg of the title compound. $^1$H NMR (CDCl$_3$) δ 2.20 (3H), 2.28 (3H), 2.53 (3H), 3.64 (2H).

Example 2
4-Acetylthiomethyl-2-methyl-5-(2-phenylsulfonylethyl) thio-1,3-thiazole To a solution of 5-acetylthio-4-acetylthiomethyl-2-methyl-1,3-thiazole (600 mg, 2.3 mmol) in methanol (10 mL) was dropwise added 0.5 M sodium methoxide in methanol (4.6 mL) at 0° C. and stirred at the same temperature for 30 min. 2-Iodoethyl phenylsulfone (620 mg, 2.1 mmol) was added and stirred for an additional 30 min. The solvent was removed and the residue was partitioned between water and ethyl acetate. The organic layer was concentrated and the residue was chromatographed (silica gel, dichloromethane), affording 800 mg of the title compound. $^1$H NMR (CDCl$_3$) δ 2.30 (s, 3H), 2.64 (s, 3H), 3.00 (t, 2H), 3.30 (t, 2H), 4.23 (s, 2H), 7.58 (2H), 7.69 (1H), 7.89 (2H).

Example 3
4-[(2-tert-Butoxycarbonylaminoethyl)thiomethyl]-2-methyl-5-(2-phenylsulfonylethyl)thio-1,3-thiazole To a stirred solution of 4-acetylthiomethyl-2-methyl-5-(2-phenylsulfonylethyl)thio-1,3-thiazole (235 mg, 0.63 mmol) and 2-bromoethyl amine hydrochloride (260 mg, 1.26 mmol) in a mixed solvent of methanol (10 mL) and tetrahydrofuran (1 mL) was dropwise added 0.5 M sodium methoxide in methanol (3.8 mL). Di-tert-butyl dicarbonate (660 mg, 3.0 mmol) was then added, and was stirred at room temperature for 0.5 h. The mixture was diluted with ethyl acetate, washed with brine, and concentrated. The residue was chromatographed on silica gel (1 to 3% methanol/dichloromethane), affording 190 mg of the title compound. $^1$H NMR (CDCl$_3$) δ 1.42 (9H), 2.62 (3H), 3.64 (2H), 3.02 (2H), 3.38 (4H), 5.15 (br s, 1H), 7.5–7.9 (5H).

Example 4
(7R)-7-Amino-3-[4-(2-N-tert-butoxycarbonylaminoethylthiomethyl)-2-methyl-1,3-thiazol-5-ylthio]-3-cephem-4-carboxylate, Diphenylmethyl Ester To a solution of 4-[(2-tert-butoxycarbonylaminoethyl) thiomethyl]-2-methyl-5-(2-phenylsulfonylethyl)thio-1,3-thiazole (300 mg, 0.61 mmol) in methanol (5 mL) was added 0.5 M sodium methoxide in methanol (0.74 mL) and stirred at room temperature for 16 h. Sodium bicarbonate (180 mg, 2.14 mmol), water (3 mL) and (7R)-7-amino-3-methanesulfonyloxy-3-cephem-4-carboxylate diphenylmethyl ester p-toluenesulfonic acid salt (300 mg, 0.47 mmol) were sequentially added. The resulting homogeneous solution was stirred at room temperature for 10 min, poured into saturated aqueous sodium chloride, and extracted with ethyl acetate. The organic extract was washed with brine and concentrated. The residue was chromatographed (3% methanol/dichloromethane) and neutralized with 4-toluenesulfonic acid (56 mg, 0.29 mmol), affording 156 mg of the title compound as p-toluenesulfonic acid salt. $^1$H NMR (CDCl$_3$) δ 1.43 (9H), 2.28 (s, 3H), 2.67 (5H), 3.2–3.4 (4H), 3.77 (s, 2H), 4.80 (1H), 4.92 (1H), 5.15 (br s, 1H), 6.97 (s, 1H), 7.03 (d, 2H), 7.2–7.5 (10H), 7.68 (d, 2H).

Example 5
(7R)-7-[(Z)-2-(2-tert-Butoxycarbonylaminopyrid-6-yl)-2-(triphenylmethoxyimino)acetamido]-3-[4-(2-N-tert-butoxycarbonylaminoethylthiomethyl)-2-methyl-1,3-thiazol-5-ylthiol]-3-cephem-4-carboxylate, Diphenylmethyl Ester To a solution of 2-(2-tert-butoxycarbonylaminopyrid-6-yl)-2-(triphenylmethoxyimino)acetic acid sodium salt (129 mg, 0.21 mmol) and pyridine (31 mg, 0.39 mmol) in anhydrous N,N-dimethylformamide (1 mL) was added diphenylphosphoryl chloride (0.042 mL, 0.2 mmol) and stirred at 0° C. for 30 min. The resulting reaction mixture was added to a solution of (7R)-7-amino-3-[4-(2-N-tert-butoxycarbonylaminoethylthiomethyl)-2-methyl-1,3-thiazol-5-ylthio]-3-cephem-4-carboxylate, diphenylmethyl ester p-toluenesulfonic acid salt in tetrahydrofuran (2 mL) at −20° C. and stirred at the same temperature for 1 h. The reaction was quenched with saturated aqueous ammonium chloride. The mixture was extracted with ethyl acetate, washed with aqueous lithium chloride, and concentrated. The residue was then chromatographed on silica gel (2% methanol/dichloromethane), affording 200 mg of the title compound. $^1$H NMR (CDCl$_3$) δ 1.3–1.6 (18H), 2.64 (5H), 3.2–3.4 (4H), 3.82 (2H), 5.08 (br s, 1H), 5.14 (d, 1H), 6.22 (dd, 1H), 1H), 7.2–7.6 (27H), 7.81 (d, 1H).

Example 6
(7R)-7-[(Z)-2-(2-Aminopyrid-6-yl)-2-(hydroxyimino) acetamido]-3-(4-(2-aminoethylthiomethyl)-2-methyl-1,3-thiazol-5-ylthio)-3-cephem-4-carboxylate, Trifluoroacetic Acid Salt A mixture of (7R)-7-[(Z)-2-(2-tert-butoxycarbonylaminopyrid-6-yl)-2-(triphenylmethoxyimino)acetamido]-3-[4-(2-N-tert-butoxycarbonylaminoethylthiomethyl)-2-methyl-1,3-thiazol-5-ylthio]-3-cephem-4-carboxylate, diphenylmethyl ester (200 mg, 0.16 mmol), phenol (1.2 g, 13 mmol), dichloromethane (0.16 mL) and triethylsilane (0.40 mL, 2.5 mmol) was warmed to 47° C. Dichloroacetic acid (0.69 mL, 8.4 mmol) was then added, and stirred at the same temperature for 70 min. The reaction was quenched with diisopropyl ether. The resulting precipitate was purified by reverse-phase chromatography (HPLC, Amberchrom, eluting with 0% to 50% acetonitrile-water (containing 0.1% trifluoroacetic acid)), affording 71 mg of the title compound. $^1$H NMR (D$_2$O) δ 2.68 (3H), 2.82 (2H), 3.23 (2H), 3.42 (d, 1H, J=18), 3.58 (d, 1H, J=18), 4.04 (2H), 5.28 (d, 1H), 5.85 (d, 1H), 6.97 (d, 1H, J=8), 7.08 (d, 1H, J=8), 7.92 (t, 1H, J=8).

Example 7
2-Bromo-4-[(2-tert-butoxycarbonylaminoethyl) thiomethyl]-1,3-thiazole To a solution of 2-(tert-butoxycarbonyl)aminoethylthiol (1.52 g, 8.61 mmol) in methanol (20 mL) was added 0.5 M sodium methoxide in methanol (16.5 mL). The solvent was then removed. The residue was triturated twice with 10% ethyl acetate-hexane and dissolved in N,N-dimethylformamide (10 mL). The solution was added to a solution of 2-bromo-4-chloromethyl-1,3-thiazole (2.34 g, 11.0 mmol) in N,N-dimethylformamide (5 mL) at 0° C. After stirring for 4 h, the mixture was diluted with water and extracted with ethyl acetate. The organic extract was washed with aqueous lithium chloride and concentrated. The residue was chromatographed on silica gel (20% ethyl acetate-hexane), affording 1.65 g of the title compound. $^1$H NMR (CDCl$_3$) δ 1.54 (9H), 2.75 (t, 2H), 3.40 (m, 2H), 3.93 (s, 2H), 5.13 (br s, 1H), 7.22 (s, 1H).

Example 8
4-[(2-tert-Butoxycarbonylaminoethyl)thiomethyl]-2-methoxy-1,3-thiazole To a solution of 2-bromo-4-[(2-tert-butoxycarbonyl-aminoethyl)thiomethyl]-1,3-thiazole (650 mg, 1.85 mmol) in N,N-dimethylformamide (5 mL) was added sodium methoxide (300 mg, 5.56 mmol) and stirred at 45° C. for 3 days. The reaction was quenched with water and the mixture was extracted with ethyl acetate. The ethyl acetate extract was washed with aqueous lithium chloride and concentrated. The residue was chromatographed on silica gel (10% ethyl acetate-hexane), affording 184 mg of the title compound. $^1$H NMR (CDCl$_3$) δ 1.54 (9H), 2.78 (t, 2H), 3.42 (m, 2H), 3.74 (s, 2H), 4.18 (s, 3H), 5.24 (br s, 1H), 6.60 (s, 1H).

Example 9
4-[-(2-tert-Butoxycarbonylaminoethyl)thiomethyl]-2-methoxy-1,3-thiazole-5-thiocyanate To a stirred solution of 4-[(2-tert-butoxycarbonylamino-ethyl)thiomethyl]-2-methoxy-1,3-thiazole (200 mg, 0.66 mmol) and potassium thiocyanate (192 mg, 1.98 mmol) in methanol (3 mL) was added bromine (0.046 mL, 0.89 mmol) in three portions over 30 min. The reaction was quenched with water and the mixture was extracted with ethyl acetate. The ethyl acetate extract was washed with aqueous sodium chloride and concentrated. The residue was chromatographed on silica gel (10% ethyl acetate-hexane), affording 130 mg of the title compound. $^1$H NMR (CDCl$_3$) δ 1.54 (9H), 2.82 (t, 2H), 3.42 (m, 2H), 3.82 (2H), 4.21 (3H), 5.18 (br s, 1H).

Example 10
(7R)-7-Amino-3-[4-(2-N-tert-butoxycarbonylaminoethyl-thiomethyl)-2-methoxy-1,3-thiazol-5-ylthio]-3-cephem-4-carboxylate, Diphenylmethyl Ester To a solution of 4-[(2-tert-butoxycarbonylaminoethyl) thiomethyl]-2-methoxy-1,3-thiazole-5-thiocyanate (84 mg, 0.23 mmol) in methanol (3 mL) was added sodium borohydride (18 mg, 0.46 mmol) and stirred at 0° C. for 15 min. Aqueous sodium bicarbonate and acetic acid were sequentially added to adjust pH of the solution to 7.5. (7R)-7-Amino-3-methanesulfonyloxy-3-cephem-4-carboxylate 4-diphenylmethyl ester p-toluensulfonic acid salt (161 mg, 0.26 mmol) and methanol (1.5 mL) were added. The resulting homogeneous solution was stirred at room temperature for 1 h, and poured into saturated aqueous sodium chloride. The mixture was extracted with ethyl acetate and the organic extract was washed with brine. p-Toluenesulfonic acid (35 mg, 0.19 mmol) was added. The solution was concentrated to dryness, affording 240 mg of the crude title compound as p-Toluenesulfonic acid salt, which was used for the next reaction without further purification. $^1$H NMR (CDCl$_3$ with a few drops of deuteromethanol) δ 1.43 (9H), 2.35 (s, 3H), 2.73 (2H), 3.32 (2H), 3.60 (4H), 4.13 (s, 3H), 4.90 (1H), 5.08 (1H), 6.97 (s, 1H), 7.20 (d, 2H), 7.3–7.5 (10H), 7.77 (d, 2H).

Example 11
(7R)-7-[(Z)-2-(2-tert-Butoxycarbonylaminopyrid-6-yl)-2-(triphenylmethoxyimino)acetamido]-3-[4-(2-N-tert-butoxycarbonylaminoethylthiomethyl)-2-methoxy-1,3-thiazol-5-ylthio]-3-cephem-4-carboxylate, Diphenylmethyl Ester To a solution of 2-(2-tert-butoxycarbonylaminopyrid-6-yl)-2-(triphenylmethoxyimino)acetic acid sodium salt (179 mg, 0.34 mmol) in anhydrous N,N-dimethylformamide (1 mL) was added diphenylphosphoryl chloride (0.067 mL, 0.32 mmol) and diisopropylethyl amine (0.060 mL, 0.34 mmol), and stirred at −20 to −30° C. for 45 min. A cooled (−30° C.) solution of (7R)-7-amino-3-[4-(2-N-tert-butoxycarbonylaminoethylthiomethyl)-2-methoxy-1,3-thiazol-5-ylthio]-3-cephem-4-carboxylate, diphenylmethyl ester p-toluenesulfonic acid salt (200 mg, 0.23 mmol) and diisopropylethyl amine (0.060 mL, 0.34 mmol) in N,N-dimethylformamide (1 mL) was then added. The resulting mixture was stirred at the, same temperature for 1 h. The reaction was quenched with saturated aqueous sodium chloride. The mixture was extracted with ethyl acetate, washed sequentially with 5% aqueous sodium bicarbonate, brine, diluted hydrochloric acid and aqueous lithium chloride, and concentrated. The residue was then chromatographed on silica gel (25% ethyl acetate-hexane), affording 130 mg of the title compound. $^1$H NMR (CDCl$_3$) δ 1.3–1.6 (18H), 2.78 (2H), 3.41 (2H), 3.50 (2H), 3.80 (2H), 4.20 (s, 3H), 5.18 (br s, 1H), 5.22 (d, 1H), 6.24 (dd, 1H), 7.04 (s, 1H), 7.2–7.7 (27H), 7.92 (d, 1H).

Example 12
(7R)-7-[(Z)-2-(2-Aminopyrid-6-yl)-2-(hydroxyimino) acetamido]-3-(4-(2-aminoethylthiomethyl)-2-methoxy-1,3-thiazol-5-ylthio)-3-cephem-4-carboxylate, Trifluoroacetic Acid Salt To a mixture of (7R)-7-[(Z)-2-(2-tert-butoxycarbonylaminopyrid-6-yl)-2-(triphenylmethoxyimino) acetamido]-3-[4-(2-N-tert-butoxycarbonylaminoethyl-thiomethyl)-2-methoxy-1,3-thiazol-5-ylthio]-3-cephem-4-carboxylate, diphenylmethyl ester (130 mg, 0.11 mmol), triethylsilane (0.3 mL) and dichloromethane (0.3 mL) was added trifluoroacetic acid (1.2 mL), and stirred at room temperature for 1 h. The mixture was concentrated to dryness and triturated with diethyl ether. The residue was dissolved in water and filtered. The filtrate was freeze-dried, affording 79 mg of the title compound. $^1$H NMR (D$_2$O) δ 2.80 (t, 2H), 3.24 (t, 2H), 3.43 (d, 1H, J=18), 3.55 (d, 1H, J=18), 3.84 (s, 2H), 4.05 (s, 3H), 5.23 (d, 1H, J=5), 5.78 (d, 1H, J=5), 6.93 (d, 1H, J=8), 7.05 (d, 1H, J=8), 7.90 (t, 1H, J=8).

Example 13
3-(2-N-t-Butoxycarbonylaminoethylthiomethyl)-5-chloro-1,2,4-thiadiazole To a solution of 5-chloro-3-chloromethyl-1,2,4-thiadiazole (560 mg, 3.3 mmol) in acetonitrile (5 mL) was added sodium iodide (1.49 g, 9.9 mmol) and stirred at room temperature for 6 h. The reaction mixture was partitioned between water and ethyl acetate. The organic layer was washed with aqueous sodium thiosulfate, dried over sodium sulfate, and concentrated to dryness, affording the crude corresponding iodide. The iodide was immediately dissolved in tetrahydrofuran (5 mL). To this solution, 2-(N-t-butoxycarbonylaminoethyl)thiol (708 mg, 4.0 mmol) and triethylamine (0.56 mL, 4.0 mmol) were added, and stirred at room temperature for 16 h. The mixture was partitioned between water and ethyl acetate. The organic solution was washed with 5% hydrochloric acid and then with water, concentrated, chromatographed (silica gel, 10% ethyl acetate-hexane), affording 780 mg of the title compound. $^1$H NMR (CDCl$_3$) δ 1.40 (9H), 2.68 (2H), 3.28 (2H), 3.88 (2H).

Example 14
(7R)-7-[(Z)-2-(2-Amino-5-chlorothiazol-4-yl)-2-(triphenylmethoxyimino)acetamido]-3-[3-(2-N-tert-butoxycarbonylaminoethylthiomethyl)-1,2,4-thiadiazol-5-ylthio]-3-cephem-4-carboxylate, Diphenylmethyl Ester A solution of 3-(2-N-t-butoxycarbonylaminoethylthiomethyl)-5-chloro-1,2,4-thiadiazole (147 mg, 0.47 mmol) and sodium sulfide (125 mg, 522 mg) in wet tetrahydrofuran (10 mL) was stirred at room temperature for 16 h. The reaction mixture was concentrated and the residue was triturated with diethyl ether. The resulting sodium thiolate salt was dissolved in ethyl acetate (10 mL). (7R)-7-[(Z)-2-(2-Amino-5-chlorothiazol-4-yl)-2-(triphenylmethoxyimino)acetamido]-3-chloro-3-cephem-4-carboxylate diphenylmethyl ester (400 mg, 0.47 mmol) was then added. After stirring for 1 h at room temperature, the mixture was washed with brine and concentrated. The residue was chromatographed (1% methanol/dichloromethane), affording 530 mg of the title compound. $^1$H NMR (CDCl$_3$) δ 1.48 (9H), 3.2–3.7 (6H), 3.88 (q, 2H), 5.05 (br s, 1H), 5.26 (d, 1H, J=5), 5.87 (br s, 2H), 6.29 (dd, 1H), 7.12 (s, 1H), 7.3–7.8 (25H).

Example 15
(7R)-7-[(Z)-2-(2-Amino-5-chlorothiazol-4-yl)-2-(hydroxyimino)acetamido]-3-(3-(2-aminoethylthiomethyl)-1,2,4-thiadiazol-5-ylthio)-3-cephem-4-carboxylate, Trifluoroacetic Acid Salt To a solution of (7R)-7-[(Z)-2-(2-amino-5-chlorothiazol-4-yl)-2-(triphenylmethoxyimino)acetamido]-3-[3-(2-N-tert-butoxycarbonylaminoethylthiomethyl)-1,2,4-thiadiazol-5-ylthio]-3-cephem-4-carboxylate; diphenylmethyl ester (145 mg, 0.13 mmol) in dichloromethane (0.5 mL) was added triethylsilane (0.5 mL) followed by addition of trifluoroacetic acid (1.5 mL). After stirring at room temperature for 1.5 hr, the mixture was concentrated and triturated with diethyl ether. The residue was dissolved in water (30 mL) and filtered. The filtrate was concentrated to dryness, affording 38 mg of the title compound. $^1$H NMR (D$_2$O) δ 3.40 (t, 2H, J=6), 4.04 (d, 1H, J=18), 4.51 (d, 1H, J=18), 4.51 (s, 2H), 5.87 (d, 1H, J=5), 6.45 (d, 1H, J=5).

Example 16
2-(2-tert-Butoxycarbonylaminoethylthio)-4-[(2-tert-butoxycarbonylaminoethyl)thiomethyl]-1,3-thiazole To a solution of 2-bromo-4-[(2-tert-butoxycarbonylaminoethyl)thiomethyl]-1,3-thiazole (421 mg, 1.2 mmol) and 2-(tert-butoxycarbonylamino)ethylthiol (234 mg, 1.3 mmol) in isopropyl alcohol (5 mL) was added 1.0 M sodium t-butoxide in t-butanol (1.2 mL) and stirred at 80° C. for 1 h. After cooling, the mixture was concentrated and partitioned between ethyl acetate and water. The ethyl acetate extract was concentrated. The residue was chromatographed on silica gel (1% methanol/dichloromethane), affording 364 mg of the title compound. $^1$H NMR (CDCl$_3$) δ 1.63 (18H), 2.78 (t, 2H), 3.42 (m, 4H), 3.61 (t, 2H), 3.90 (s, 2H), 5.18 (br s, 1H), 7.13 (1H).

Example 17
2-(2-N-tert-Butoxycarbonylaminoethylthio)-4-[(2-N-tert-butoxycarbonylaminoethyl)thiomethyl]-1,3-thiazole-5-thiocyanate To a solution of 2-(2-N-tert-butoxycarbonylaminoethylthio)-4-[(2-N-tert-butoxycarbonylaminoethyl)thiomethyl]-1,3-thiazole (750 mg, 1.67 mmol) and potassium thiocyanate (486 mg, 5.0 mmol) in anhydrous methanol (7 mL) was dropwise added bromine for 1 h, until the starting material had nearly disappeared. The mixture was stirred at room temperature for additional 16 h, poured into ethyl acetate and water. The ethyl acetate layer was washed with aqueous sodium bicarbonate, and concentrated. The residue was chromatographed on silica gel (0.5% methanol-dichloromethane), affording 346 mg of the title compound. $^1$H NMR (CDCl$_3$) δ 1.65 (18H), 2.780 (t, 2H), 3.42 (m, 4H), 3.61 (t, 2H), 4.02 (s, 2H), 5.20 (br s, 1H), 5.42 (br s, 1H).

Example 18
(7R)-7-Amino-3-[2-(2-N-tert-butoxycarbonylaminoethylthio)-4-(2-N-tert-butoxycarbonylaminoethylthiomethyl)-1,3-thiazol-5-ylthio]-3-cephem-4-carboxylate, Diphenylmethyl Ester To a solution of 2-(2-N-tert-butoxycarbonylaminoethylthio)-4-[(2-N-tert-butoxycarbonylaminoethyl)thiomethyl]-1,3-thiazole-5-thiocyanate (257 mg, 0.51 mmol) in methanol (20 mL) was added sodium borohydride (18 mg, 0.51 mmol) and stirred at 0° C. for 2 h. The solvent was partially removed and diluted with water (10 mL). The pH of the solution was adjusted to about 7.5 with phosphoric acid, and then sodium bicarbonate (128 mg, 1.5 mmol) was added. (7R)-7-Amino-3-methanesulfonyloxy-3-cephem-4-carboxylate 4-diphenylmethyl ester p-toluensulfonic acid salt (353 mg, 0.56 mmol) and ethyl acetate (10 mL) were added. The resulting biphasic solution was stirred at room temperature for 1 h. The organic layer was taken, washed with brine, and concentrated. The residue was chromatographed on silica gel (1% methanol/dichloromethane), affording 320 mg of the title compound. $^1$H NMR (CDCl$_3$) δ 1.55 (18H), 2.84 (2H), 3.45 (4H), 3.55 (2H), 3.61 (2H), 3.88 (2H), 4.87 (d, 1H), 5.03 (d, 1H), 5.22 (br s, 1H), 5.5.45 (br s, 1H), 7.05 (s, 1H), 7.3–7.7 (10H).

Example 19
(7R)-7-[(Z)-2-(2-Amino-5-chlorothiazol-4-yl)-2-(triphenylmethoxyimino)acetamido]-3-[2-(2-N-tert-butoxycarbonylaminoethylthio)-4-(2-N-tert-butoxycarbonylaminoethylthiomethyl)-1,3-thiazol-5-ylthio]-3-cephem-4-carboxylate, Diphenylmethyl Ester To a cooled (−30° C.) solution of 2-(2-amino-5-chlorothiazol-4-yl)-2-(triphenylmethoxyimino)acetic acid (46 mg, 0.10 mmol) and (7R)-7-amino-3-[2-(2-N-tert-butoxycarbonylaminoethylthio)-4-(2-N-tert-butoxycarbonylaminoethylthiomethyl)-1,3-thiazol-5-ylthio]-3-cephem-4-carboxylate, diphenylmethyl ester (70 mg, 0.083 mmol) in tetrahydrofuran (10 mL) was added diisopropylethyl amine (0.036 mL, 0.21 mmol) and phosphorus oxychloride (0.012 mL, 0.12 mmol), and stirred at −20° C. for 1 h. The reaction was quenched with water (50 mL). The mixture was extracted with ethyl acetate, washed sequentially with 5% aqueous sodium bicarbonate, brine, and diluted hydrochloric acid. After removal of solvent, the residue was chromatographed on silica gel (1% methanol/dichloromethane), affording 90 mg of the title compound. $^1$H NMR (CDCl$_3$) δ 1.56 (18H), 2.80 (2H), 3.42 (6H), 3.61 (2H), 3.86 (2H), 5.15 (d, 1H), 5.18 (br s, 1H), 5.40 (br s, 1H), 5.93 (br s, 2H), 6.18 (dd, 1H), 7.07 (s, 1H), 7.2–7.7 (25H).

Example 20
(7R)-7-[(Z)-2-(2-Amino-5-chlorothiazol-4-yl)-2-(hydroxyimino)acetamido]-3-(2-aminoethylthio-4-aminoethylthiomethyl-1,3-thiazol-5-ylthio)-3-cephem-4-carboxylate, Trifluoroacetic Acid Salt To a solution of (7R)-7-[(Z)-2-(2-amino-5-chlorothiazol-4-yl)-2-(triphenylmethoxyimino)acetamido]-3-[2-(2-N-tertbutoxycarbonylaminoethylthio)-4-(2-N-tert-butoxycarbonylaminoethylthiomethyl)-1,3-thiazol-5-ylthio]-3-cephem-4-carboxylate, diphenylmethyl ester (90 mg, 0.070 mmol) in dichloromethane (0.15 mL) was added triethylsilane (0.15 mL) followed by addition of trifluoroacetic acid (0.6 mL). After stirring at room temperature for 1.5 hr, the mixture was concentrated to dryness. The residue was triturated with diethyl ether, dissolved in water (7 mL), and filtered. The filtrate was concentrated to dryness, affording 38 mg of the title compound. $^1$H NMR (D$_2$O) δ 2.72 (t, 2H, J=6), 3.19 (t, 2H, J=6), 3.34 (t, 2H), 3.40 (d, 1H, J=18), 3.45 (t, 2H), 3.53 (d, 1H, J=18), 3.88 (s, 2H), 5.14 (d, 1H, J=5), 5.76 (d, 1H, J=5).

Example 21

2-(2-N-t-Butoxycarbonylaminoethylthio)-6-chloropyrazine

To a solution of 2,6-dichloropyrazine (1.80 g, 12.2 mmol) and 2-(N-t-butoxycarbonylamino)ethylthiol (2.5 g, 14.0 mmol) in methanol (5 mL) was added 0.5 M sodium methoxide in methanol (24.4 mL) and stirred at room temperature for 3 days. The solvent was removed and the residue was partitioned between water and ethyl acetate. The organic layer was dried over sodium sulfate, and concentrated to dryness, affording 3.1 g of the crude title compound, which was used for the next reaction without further purification. $^1$H NMR (CDCl$_3$) δ 1.58 (9H), 3.41 (2H), 3.56 (2H), 5.05 (br s, 1H), 8.35 (s, 1H), 8.45 (s, 1H).

Example 22

2-(2-N-t-Butoxycarbonylaminoethylthio)-6-(methoxycarbonylethylthio)pyrazine

A solution of 2-(2-N-t-butoxycarbonylaminoethylthio)-6-chloropyrazine (355 mg, 1.22 mmol) and sodium thiolate salt of 3-mercaptopropionic acid methyl ester (160 mg, 1.35 mmol; prepared by reacting the corresponding thiol with sodium methoxide) in N,N-dimethylformamide (5 mL) was stirred at room temperature for 16 h. The reaction was quenched with water and ethyl acetate. The ethyl acetate layer was washed with aqueous lithium chloride solution, dried over sodium sulfate, and concentrated. The residue was chromatographed (silica gel, 10 to 20% ethyl acetate-hexane), affording 310 mg of the title compound. $^1$H NMR (CDCl$_3$) δ 1.55 (9H), 2.84 (2H), 3.40 (2H), 3.56 (4H), 3.82 (3H), 5.32 (br s, 1H), 8.21 (2H).

Example 23

(7R)-7-Amino-3-[6-(2-N-tert-butoxycarbonylaminoethylthio)pyraz-2-ylthio]-3-cephem-4-carboxylate, Diphenylmethyl Ester To a solution of 2-(2N-t-butoxycarbonylaminoethylthio)-6-(methoxycarbonylethylthio)pyrazine (140 mg, 0.375 mmol) in isopropanol (2 mL) was added 0.5 M sodium methoxide in methanol (0.73 mL), and stirred at room temperature for 0.5 h. After removal of solvent, the resulting thiolate was added to a mixture of ethyl acetate (5 mL), water (2 mL) and sodium bicarbonate (95 mg, 1.1 mmol). (7R)-7-Amino-3-methanesulfonyloxy-3-cephem-4-carboxylate diphenylmethyl ester p-toluensulfonic acid salt (161 mg, 0.26 mmol) was then added. After stirring for 1 h at room temperature, the organic layer was taken, washed with brine, and concentrated. The residue was chromatographed (silica gel, dichloromethane), affording 157 mg of the title compound. $^1$H NMR (CDCl$_3$) δ 1.55 (9H), 3.2–3.5 (4H), 3.52 (d, 1H, J=18), 3.82 (d, 1H, J=18), 4.98 (d, 1H), 5.14 (d, 1H), 5.15 (br s, 1H), 7.01 (s, 1H), 7.3–7.5 (10H), 8.05 (s, 1H), 8.25 (s, 1H).

Example 24

(7R)-7-[(Z)-2-(2-tert-Butoxycarbonylaminopyrid-6-yl)-2-(triphenylmethoxyimino)acetamido]-3-[6-(2-N-tert-butoxycarbonylaminoethylthio)pyraz-2-ylthio]-3-cephem-4-carboxylate, Diphenylmethyl Ester To a solution of 2-(2-tert-butoxycarbonylaminopyrid-6-yl)-2-(triphenylmethoxyimino)acetic acid sodium salt (200 mg, 0.38 mmol) in anhydrous N,N-dimethylformamide (1 mL) was added diphenylphosphoryl chloride (0.07 mL, 0.34 mmol) and diisopropylethyl amine (0.125 mL, 0.72 mmol), and stirred at −30° C. for 1 h. A cooled (−30° C.) solution of (7R)-7-amino-3-[6-(2-N-tert-butoxycarbonylaminoethylthio)pyraz-2-ylthio]-3-cephem-4-carboxylate, diphenylmethyl ester (155 mg, 0.24 mmol) in N,N-dimethylformamide (2 mL) was added, and the resulting mixture was stirred at the same temperature for 1 h. The reaction was quenched with saturated aqueous sodium chloride. The mixture was extracted with ethyl acetate, washed sequentially with 5% aqueous sodium bicarbonate, brine, diluted hydrochloric acid and aqueous lithium chloride, and concentrated. The residue was chromatographed on silica gel (25% ethyl acetate-hexane), affording 214 mg of the title compound. $^1$H NMR (CDCl$_3$) δ 1.21 (9H), 1.60 (9H), 2.8–3.9 (4H), 3.42 (d, 1H, J=18), 3.86 (d, 1H, J=18), 4.82 (br s, 1H), 5.38 (d, 1H), 6.28 (dd, 1H), 7.10 (s, 1H), 7.2–7.7 (27H), 7.91 (d, 1H), 8.02 (s, 1H), 8.22 (s, 1H), 8.68 (br s, 1H).

Example 25

(7R)-7-[(Z)-2-(2-Aminopyrid-6-yl)-2-(hydroxyimino)acetamido]-3-(6-(2-aminoethylthio)pyraz-2-ylthio)-3-cephem-4-carboxylate, Trifluoroacetic Acid Salt To a mixture of (7R)-7-[(Z)-2-(2-tert-butoxycarbonylaminopyrid-6-yl)-2-(triphenylmethoxyimino)acetamido]-3-[6-(2-N-tert-butoxycarbonylaminoethylthio)pyraz-2-ylthio]-3-cephem-4-carboxylate, diphenylmethyl ester (210 mg, 0.18 mmol), triethylsilane (0.4 mL) and dichloromethane (0.4 mL) was added trifluoroacetic acid (1.2 mL) and stirred at room temperature for 1 h. The mixture was concentrated to dryness and triturated with diethyl ether. The residue was dissolved in water and insoluble impurities were filtered out. The filtrate was freeze-dried, affording 135 mg of the title compound. $^1$H NMR (D$_2$O) δ 3.2–3.7 (m, 4H), 3.46 (d, 1H, J=18), 3.86 (d, 1H, J=18), 5.37 (d, 1H, J=5), 5.84 (d, 1H, J=5), 6.96 (d, 1H, J=8), 7.07 (d, 1H, J=8), 7.90 (t, 1H, J=8), 8.19 (s, 1H), 8.26 (s, 1H).

Example 26

3-(2-N-t-Butoxycarbonylaminoethylthio)-2-chloropyrazine

To a solution of 2,3-dichloropyrazine (1.53 g, 10.3 mmol) and 2-(N-t-butoxycarbonylamino)ethylthiol (2.1 g, 11.9 mmol) in methanol (5 mL) was added 0.5 M sodium methoxide in methanol (20.6 mL), and stirred at room temperature for 16 h. The solvent was removed, and the residue was partitioned between water and ethyl acetate. The organic layer was dried over sodium sulfate, and concentrated to dryness, affording 3.1 g of the crude title compound, which was used for the next reaction without further purification. $^1$H NMR (CDCl$_3$) δ 1.55 (9H), 3.40 (2H), 3.58 (2H), 5.03 (br s, 1H), 8.18 (d, 1H), 8.40 (d, 1H).

Example 27

3-(2-N-t-Butoxycarbonylaminoethylthio)-2-(methoxycarbonylethylthio)pyrazine

A solution of 3-(2N-t-butoxycarbonylaminoethylthio)-2-chloropyrazine (355 mg, 1.2 mmol) and sodium thiolate salt of 3-mercaptopropionic acid methyl ester (140 mg, 1.3 mmol; prepared by reacting the corresponding thiol with sodium methoxide) in N,N-dimethylformamide (5 mL) was stirred at room temperature for 16 h and heated at 45° C. for 5 h. The reaction was quenched with water and ethyl acetate. The ethyl acetate layer was washed with aqueous lithium chloride solution, dried over sodium sulfate, and concentrated. The residue was chromatographed (silica gel, dichloromethane), affording 175 mg of the title compound. $^1$H NMR (CDCl$_3$) δ 1.55 (9H), 2.88 (t, 2H), 3.46 (2H), 3.55 (4H), 3.80 (3H), 8.18 (2H).

Example 28

(7R)-7-Amino-3-[3-(2-N-tert-butoxycarbonylaminoethylthio)pyraz-2-ylthio]-3-cephem-4-carboxylate, Diphenylmethyl Ester To a solution of 3-(2-N-t-butoxycarbonylaminoethylthio)-2-(methoxycarbonylethylthio)pyrazine (257 mg, 0.69 mmol) in methanol (5 mL) was added 0.5 M sodium methoxide in methanol (1.33 mL), and stirred at room temperature for 45 min. After removal of solvent, the resulting thiolate was redissolved in methanol (3 mL). A solution of (7R)-7-amino-3-methanesulfonyloxy-3-cephem-4-carboxylate diphenylmethyl ester (479 mg as the salt, 0.76 mmol, freshly prepared from the corresponding p-toluenesulfonic acid salt) in a mixed solvent of methanol (2 mL) and ethyl acetate (5 mL) was then added. After stirring for 45 min at room temperature, the solvents were partially removed, and mixed with ethyl acetate and water. The organic layer was taken, washed with brine, and concentrated. The residue was chromatographed (silica gel, dichloromethane), affording 93 mg of the title compound. $^1$H NMR (CDCl$_3$) δ 1.55 (9H), 3.3–3.5 (4H), 3.55 (d, 1H, J=18), 3.88 (d, 1H, J=18), 4.92 (d, 1H), 5.08 (br s, 1H), 5.18 (d, 1H), 7.07 (s, 1H), 7.3–7.5 (10H), 8.17 (d, 1H), 8.22 (d, 1H).

Example 29

(7R)-7-[(Z)-2-(2-tert-Butoxycarbonylaminopyrid-6-yl)-2-(triphenylmethoxyimino)acetamido]-3-[3-(2-N-tert-butoxycarbonylaminoethylthio)pyraz-2-ylthio]-3-cephem-4-carboxylate, Diphenylmethyl Ester To a solution of 2-(2-tert-butoxycarbonylaminopyrid-6-yl)-2-(triphenylmethoxyimino)acetic acid sodium salt (81 mg, 0.16 mmol) in anhydrous N,N-dimethylformamide (2 mL) was added diphenylphosphoryl chloride (0.037 mL, 0.18 mmol) and diisopropylethyl amine (0.067 mL, 0.39 mmol) and stirred at −30° C. for 1 h. A cooled (−30° C.) solution of (7R)-7-amino-3-[3-(2-N-tert-butoxycarbonylaminoethylthio)pyraz-2-ylthio]-3-cephem-4-carboxylate, diphenylmethyl ester (84 mg, 0.13 mmol) in N,N-dimethylformamide (2 mL) was added, and the resulting mixture was stirred at the same temperature for 1 h. The reaction was quenched with saturated aqueous sodium chloride. The mixture was. extracted with ethyl acetate, washed sequentially with 5% aqueous sodium bicarbonate, brine, diluted hydrochloric acid, and aqueous lithium chloride, and concentrated. The residue was chromatographed on silica gel (0.5% methanol/dichloromethane), affording 62 mg of the title compound. $^1$H NMR (CDCl$_3$) δ 1.5 (9H), 1.58 (9H), 2.3–3.5 (5H), 3.82 (d, 1H, J=18), 5.04 (br s, 1H), 5.37 (d, 1H), 6.28 (dd, 1H), 6.88 (br s, 1H), 7.08 (s, 1H), 7.2–7.7 (27H), 7.98 (d, 1H), 8.14 (d, 1H, J=3), 8.22 (d, 1H, J=3).

Example 30

(7R)-7-[(Z)-2-(2-Aminopyrid-6-yl)-2-(hydroxyimino)acetamido]-3-(3-(2-aminoethylthio)pyraz-2-ylthio)-3-cephem-4-carboxylate, Trifluoroacetic Acid Salt To a mixture of (7R)-7-[(Z)-2-(2-tert-butoxycarbonylaminopyrid-6-yl)-2-(triphenylmethoxyimino)acetamido]-3-[3-(2-N-tert-butoxycarbonylaminoethylthio)pyraz-2-ylthio]-3-cephem-4-carboxylate, diphenylmethyl ester (62 mg, 0.05 mmol), triethylsilane (0.3 mL) and dichloromethane (0.3 mL) was added trifluoroacetic acid (1.0 mL), and stirred at room temperature for 1 h. The mixture was concentrated to dryness, and triturated with diethyl ether. The residue was dissolved in water (10 mL) and filtered. The filtrate was freeze-dried, affording 30 mg of the title compound: $^1$H NMR (D$_2$O) δ 3.34 (t, 2H), 3.45 (d, 1H, J=18), 3.52 (t, 2H), 3.84 (d, 1H, J=18), 5.37 (d, 1H, J=5), 5.91 (d, 1H, J=5), 6.95 (d, 1H, J=8), 7.07 (d, 1H, J=8), 7.88 (t, 1H, J=8), 8.19 (d, 1H), J=3), 8.28 (d, 1H, J=3).

Example 31

2-(2-N-t-Butoxycarbonylaminoethylthio)-4-chloropyrimidine

To a solution of 2,4-dichloropyrimidine (477 mg, 3.0 mmol) and 2-(N-t-butoxycarbonylamino)ethylthiol (637 mg, 3.6 mmol) in methanol (20 mL) was added 0.5 M sodium methoxide in methanol (6.0 mL) and stirred at 45° C. for 10 min. The solvent was removed, and the residue was partitioned between water and ethyl acetate. The organic layer was taken, dried over sodium sulfate, and concentrated. Crystallization of the solid residue from hexane/dichloromethane afforded 645 mg of the title compound. $^1$H NMR (CDCl$_3$) δ 1.55 (9H), 3.40 (2H), 3.59 (2H), 5.08 (br s, 1H), 7.21 (d, 1H), 8.35 (d, 1H).

Example 32

2-(2-N-t-Butoxycarbonylaminoethylthio)-4-(methoxycarbonylethylthio)pyrimidine

A solution of 2-(2-N-t-butoxycarbonylaminoethylthio)-4-chloropyrimidine (645 mg, 2.2 mmol) and sodium thiolate salt of 3-mercaptopropionic acid methyl ester (320 mg, 2.4 mmol; prepared by reacting the corresponding thiol with sodium methoxide) in methanol (5 mL) was stirred at room temperature for 16 h. The mixture was concentrated, and partitioned between water and ethyl acetate. The ethyl acetate layer was concentrated, and the residue was chromatographed (silica gel, dichloromethane), affording 175 mg of the title compound. $^1$H NMR (CDCl$_3$) δ 1.55 (9H), 2.88 (2H), 3.40 (2H), 3.55 (4H), 3.80 (3H), 5.16 (br s, 1H), 5.30 (br s, 1H), 6.92 (d, 1H), 8.18 (d, 1H).

Example 33

(7R)-7-Amino-3-[2-(2-N-tert-butoxycarbonylaminoethylthio)pyrimid-4-ylthio]-3-cephem-4-carboxylate, Diphenylmethyl Ester To a solution of 2-(2-N-t-butoxycarbonylaminoethylthio)-4-(methoxycarbonylethylthio)pyrimidine (138 mg, 0.37 mmol) in isopropanol (5 mL) was added 0.5 M sodium methoxide in methanol (0.74 mL), and stirred at room temperature for 1 h. After removal of solvent, the resulting thiolate was triturated with diethyl ether and dissolved in a mixture of tetrahydrofuran (2 mL) and methanol (0.5 mL). A solution of (7R)-7-Amino-3-methanesulfonyloxy-3-cephem-4-carboxylate diphenylmethyl ester (170 mg, 0.37 mmol) and sodium bicarbonate (60 mg, 0.71 mmol) in tetrahydrofuran (3 mL) and water (0.3 mL) was then added. After stirring for 2 h at 0° C., the mixture was quenched with saturated ammonium chloride, extracted with ethyl acetate, washed with brine, and concentrated. The residue was chromatographed (1% methanol/dichloromethane), affording 30 mg of the title compound. $^1$H NMR (CDCl$_3$) δ 1.55 (9H), 3.30 (2H), 3.41 (2H), 3.75 (d, 1H, J=18), 3.91 (d, 1H, J=18), 4.98 (d, 1H, J=5), 5.09 (br s, 1H), 5.15 (d, 1H, J=5), 6.98 (d, 1H), 7.03 (s, 1H), 7.3–7.5 (10H), 8.21 (d, 1H).

Example 34
(7R)-7-[(Z)-2-(2-tert-Butoxycarbonylaminopyrid-6-yl)-2-(triphenylmethoxyimino)acetamido]-3-[2-(2-N-tert-butoxycarbonylaminoethylthio)pyrimid-4-ylthio]-3-cephem-4-carboxylate, Diphenylmethyl Ester To a solution of 2-(2-tert-butoxycarbonylaminopyrid-6-yl)-2-(triphenylmethoxyimino)acetic acid sodium salt (54 mg, 0.1 mmol) in anhydrous N,N-dimethylformamide (1 mL) was added diphenylphosphoryl chloride (0.019 mL, 0.09 mmol), and stirred at room temperature for 30 min. The mixture was then cooled to −20° C., and a solution of (7R)-7-amino-3-[2-(2-N-tert-butoxycarbonylaminoethylthio)pyrimid-4-ylthio]-3-cephem-4-carboxylate, diphenylmethyl ester (30 mg, 0.045 mmol) in N,N-dimethylformamide (1 mL) was added. After stirring at the same temperature for 1 h, the reaction was quenched with saturated aqueous ammonium chloride. The mixture was extracted with ethyl acetate, washed sequentially with diluted hydrochloric acid, aqueous lithium chloride, saturated sodium bicarbonate, and aqueous lithium chloride, and concentrated. The residue was chromatographed on silica gel (0.5% methanol/dichloromethane), affording 20 mg of the title compound. $^1$H NMR (CDCl$_3$) δ 1.42 (9H), 1.50 (9H), 3.10 (2H), 3.35 (2H), 3.60 (d, 1H, J=18), 3.82 (d, 1H, J=18), 4.75 (br s, 1H), 5.38 (d, 1H, J=5), 6.26 (dd, 1H), 6.95 (d, 1H, J=5), 7.03 (s, 1H), 7.2–7.6 (28H), 7.81 (br s, 1H), 8.18 (d, 1H, J=5).

Example 35
(7R)-7-[(Z)-2-(2-Aminopyrid-6-yl)-2-(hydroxyimino)acetamido]-3-(2-(2-aminoethylthio)pyrimid-4-ylthio)-3-cephem-4-carboxylate, Trifluoroacetic Acid Salt To a mixture of (7R)-7-[(Z)-2-(2-tert-butoxycarbonylaminopyrid-6-yl)-2-(triphenylmethoxyimino)acetamido]-3-(2-(2-tert-butoxycarbonylaminoethylthio)-pyrimid-4-ylthio)-3-cephem-4-carboxylate, diphenylmethyl ester (20 mg, 0.02 mmol), triethylsilane (0.1 mL) and dichloromethane (0.1 mL) was added trifluoroacetic acid (0.5 mL), and stirred at room temperature for 1 h. The mixture was concentrated to dryness, and triturated with diethyl ether. The residue was dissolved in water and filtered. The filtrate was freeze-dried, affording 11 mg of the title compound. $^1$H NMR (D$_2$O) δ 3.31 (2H), 3.42 (2H), 3.50 (d, 1H, J=18), 3.93 (d, 1H, J=18), 5.37 (d, 1H), 5.87 (d, 1H), 6.97 (d, 1H, J=8), 7.08 (d, 1H, J=8), 7.18 (d, 1H, J=5), 7.89 (t, 1H, J=8), 8.18 (d, 1H, J=5).

Example 36
(7R)-7-[(Z)-2-(2-Triphenylmethylamino-5-thiazol-4-yl)-2-(triphenylmethoxyimino)acetamido]-3-[3-(2-N-tert-butoxycarbonylaminoethylthio)pyraz-2-ylthio]-3-cephem-4-carboxylate, 4-Methoxybenzyl Ester To a solution of 3-(2-N-t-butoxycarbonylaminoethylthio)-2-(methoxycarbonylethylthio)pyrazine (62 mg, 0.17 mmol) in methanol was added 0.5 M sodium methoxide in methanol (0.33 mL), and stirred at room temperature for 2 h. After removal of solvent, the resulting thiolate was dissolved in ethyl acetate and (7R)-7-[(Z)-2-(2-triphenylmethylamino-5-thiazol-4-yl)-2-(triphenylmethoxyimino)acetamido]-3-trifluoromethanesulfonyloxy-3-cephem-4-carboxylate 4-methoxybenzyl ester (186 mg, 0.27 mmol) was added. After stirring for 1 h at room temperature, the mixture was washed with brine, and concentrated. The residue was chromatographed (1% methanol/dichloromethane), affording 55 mg of the title compound. $^1$H NMR (CDCl$_3$) δ 1.55 (9H), 3.37 (d, 1H, J=18), 3.42 (2H), 3.52 (2H), 3.89 (d, 1H, J=18), 3.91 (s, 3H), 5.09 (br s, 1H), 5.27 (d, 1H, J=5), 5.33 (2H), 6.20 (dd, 1H), 6.52 (s, 1H), 6.85 (br s, 1H), 6.96 (d, 2H), 7.3–7.5 (32H), 8.07 (d, 1H), 8.21 (d, 1H).

Example 37
(7R)-7-[(Z)-2-(2-Aminothiazol-4-yl)-2-(hydroxyimino)acetamido]-3-[3-(2-aminoethylthiopyraz-2-ylthio)]-3-cephem-4-carboxylate, Trifluoroacetic Acid Salt To a solution of (7R)-7-[(Z)-2-(2-triphenylmethylamino-5-thiazol-4-yl)-2-(triphenylmethoxyimino)acetamido]-3-[3-(2-N-tert-butoxycarbonylaminoethylthio)pyraz-2-ylthio]-3-cephem-4-carboxylate, 4-methoxybenzyl ester (55 mg, 0.043 mmol) in dichloromethane (0.2 mL) was added triethylsilane (0.2 mL) followed by addition of trifluoroacetic acid (0.8 mL). After stirring at room temperature for 1 hr, the mixture was concentrated, and triturated with diethyl ether, affording 5.5 mg of the title compound. $^1$H NMR (D$_2$O) δ 3.81 (t, 2H, J=6), 3.94 (d, 1H, J=18), 4.01 (t, 2H, J=6), 4.36 (d, 1H, J=18), 5.83 (d, 1H, J=5), 6.36 (d, 1H, J=5), 7.47 (s, 1H), 8.73 (d, 1H), 8.81 (d, 1H).

Example 38
2-[(2-N-tert-Butoxycarbonylaminoethylthio)ethylthio]-5-mercapto-1,3,4-thiadiazole To a stirred suspension of 2-chloroethylamine hydrochloride (1.13 g, 9.8 mmol) and 2,5-dimercapto-1,3,4-thiadiazole (1.47 g, 9.8 mmol) in methanol (20 mL) was added sodium methoxide in methanol (39.2 mL, 0.5 M). After overnight reaction at 60° C., reaction was allowed to cool to room temperature, di-t-butyldicarbonate (2.14 g, 9.8 mmol) was added and stirring was continued for 18 hrs. Solvent was removed under reduced pressure and the residue was partitioned between 0.5 M solution of potassium carbonate and ether. Aqueous layer was neutralized with dilute hydrochloric acid and the product was extracted with ethyl acetate. Extracts were dried over sodium sulfate, and concentrated to afford semi-solid residue which upon trituration with methylene chloride produced title product (0.67 g), which was used in next step without further purification. $^1$H NMR (CDCl$_3$) δ 1.50 (s, 9H), 3.25 (m, 2H), 3.50 (m, 2H), 5.00 (s, 1H).

Example 39
(7R)-7-[(Z)-2-(2-Amino-5-chlorothiazol-4-yl)-2-(triphenylmethoxyimino)acetamido]-3-{2-[(2-t-butoxycarbonylamino)ethylthio]-1,3,4-thiadiazol-5-ylthio}-3-cephem-4-carboxylate, Diphenylmethyl Ester To a solution of 2-[(2-t-butoxycarbonylamino)ethylthio]-5-mercapto-1,3,4-thiadiazole (76 mg, 0.26 mmol) and (7R)-7-[(Z)-2-(2-amino-5-chlorothiazol-4-yl)-2-(triphenylmethoxyimino)acetamido]-3-methanesulfonyloxy-3-cephem-4-carboxylate, diphenylmethyl ester (235 mg, 0.26 mmol) in methylene chloride (5 mL) were added tetrabutylammonium bromide (8 mg, 0.026 mmol) and aqueous solution of sodium bicarbonate (5.0 mL, 0.5 M). After stirring vigorously for 20 hours at room temperature reaction mixture was partitioned between ethyl acetate and water. Organic extract was dried over sodium sulfate and concentrated under reduced pressure to produce oily residue, which was purified by radial chromatography (2% methanol in methylene chloride) on silica gel to afford protected cephem (25 mg). $^1$H NMR (CDCl$_3$) δ 1.45 (s, 9H), 3.20 (d, 1H), 3.50 (m, 5H), 5.10 (d, 1H), 5.60 (s, 1H), 6.20 (m, 1H), 7.00 (s, 1H), 7.20–7.60 (m, 25H).

Example 40
(7R)-7-[(Z)-2-(2-Amino-5-chlorothiazol-4-yl)-2-(hydroxyimino)acetamido]-3-[2-(2-aminoethylthio)-1,3,4-thiadiazol-5-ylthio]-3-cephem-4-carboxylate, Trifluoroacetic Acid Salt To a solution of (7R)-7-[(Z)-2-(2-amino-5-chlorothiazol-4-yl)-2-(triphenylmethoxyimino)acetamido]-3-{2-[(2-t- butoxycarbonylamino)ethylthio]-1,3,4-thiadiazol-5-ylthio}-3-cephem-4-carboxylate, diphenylmethyl ester (25 mg) in methylene chloride (0.5 mL) were added triethylsilane (0.25 mL) and trifluoroacetic acid (0.5 mL) at 0° C. After 30 min cooling was removed and stirring was continued for 1 hour at room temperature. Reaction mixture was concentrated under reduced pressure and the oily residue was triturated with diisopropyl ether and filtered to produce precipitate of the title product (12 mg).

Example 41
2-Amino-4-chloromethyl-1,3-thiazole

To a solution of thiourea (9.56 g, 0.125 mol) in methanol (100 mL) was added 1,3-dichloroacetone (17.57 g, 0.138 mol) at room temperature. After 30 min the reaction mixture was partitioned between ethyl acetate and aqueous sodium bicarbonate. Organic extract was dried over sodium sulfate and concentrated to afford crude title product (16.2 g) which was used immediately for next step without further purification. $^1$H NMR (CDCl$_3$/CD$_3$OD) δ 4.40 (s, 2H), 6.40 (s, 1H).

Example 42
2-Amino-4-(2-t-butyloxycarbonylaminoethylthiomethyl)-1,3-thiazole To a solution of 2-amino-4-chloromethyl-1,3-thiazole (16.2 g, 0.108 mol) in dimethylformamide (80 mL) was added 2-t-butyloxycarbonylaminoethanethiol (28.9 g, 0.163 mol) followed by potassium carbonate (45 g, 0.326 mol). After 1 hour of vigorous stirring reaction mixture was partitioned between ethyl acetate and water. Organic layer was thoroughly washed with water, dried over sodium sulfate and concentrated under reduced pressure. Flash column chromatography of the oily residue (2% methanol in methylene chloride) afforded oily product (20.0 g). $^1$H NMR (CDCl$_3$) δ 1.42 (s, 9H), 2.65 (m, 2H), 3.35 (m, 2H), 3.80 (s, 2H), 2.65 (m, 2H), 5.00 (s, 1H).

Example 43
2-Amino-4-(2-t-butyloxycarbonylaminoethylthiomethyl)-5-thiocyanato-1,3-thiazole To a stirred solution of 2-amino-4-(2-t-butyloxycarbonylaminoethylthiomethyl)-1,3-thiazole (4.27 g, 14.8 mmol) and potassium thiocyanate (2.87 g, 29.5 mmol) in methanol (30 mL) cooled to 0° C. was added dropwise bromine (3.55 g, 0.022 mol) and stirring was continued for 45 min. Reaction mixture was partitioned between ethyl acetate and water. Organic layer was dried over sodium sulfate and concentrated under reduced pressure to afford solid residue of title product in quantitative yield. Crude product was used in next step without further purification.

Example 44
2-Amino-4-(2-t-butyloxycarbonylaminoethylthiomethyl)-5-mercapto-1,3-thiazole To a stirred solution of 2-amino-4-(2-t-butyloxycarbonylaminoethylthiomethyl)-5-thiocyanato-1,3-thiazole (2.83 g, 8.19 mmol) in methanol (30 mL) at room temperature was added sodium borohydride under nitrogen (0.93 g, 24.6 mol) and stirring was continued for 1 hour. After addition of water, stirring was continued until gas evolution subsided and the aqueous solution was washed with methylene chloride to remove impurities. Aqueous thiolate solution was neutralized with dilute hydrochloric acid and the product was extracted with ethyl acetate (all manipulations were performed under nitrogen to prevent formation of disulfide). Organic layer was dried over sodium sulfate and concentrated under reduced pressure to afford pale orange foam of title product (1.72 g) which was used for further steps without further purification. $^1$H NMR (CDCl$_3$) δ 1.40 (s, 9H), 2.60 (m, 2H), 3.20 (m, 2H), 3.65 (s, 2H), 5.40 (s, 1H).

Example 45
(7R)-7-[(Z)-2-(2-Amino-5-chlorothiazol-4-yl)-2-(triphenylmethoxyimino)acetamido]-3-[2-amino-4-(2-t-butyloxycarbonylaminoethylthiomethyl)-1,3-thiazol-5-ylthio]-3-cephem-4-carboxylate, Diphenylmethyl Ester Solution of 2-amino-4-(2-t-butyloxycarbonylaminoethylthiomethyl)-5-mercapto-1,3-thiazole (1.72 g, 5.35 mmol), (7R)-7-[(Z)-2-(2-amino-5-chlorothiazol-4-yl)-2-(triphenylmethoxyimino)acetamido]-3-chloro-3-cephem-4-carboxylate, diphenylmethyl ester (4.52 g, 5.35 mmol) and tetrabutylammonium bromide (0.173 g, 0.53 mmol) in methylene chloride (30 mL) and methanol (3 mL) was vigorously stirred with aqueous solution of sodium bicarbonate (30 mL, 0.5 M) under nitrogen at room temperature. After 16 hours reaction mixture was partitioned between water and methylene chloride and the product was isolated by flash chromatography on silica gel column (ethyl acetate-hexane-2/1) in form of pale yellow foam (0.60 g). $^1$H NMR (CDCl$_3$/CD$_3$OD) δ 1.40 (s, 9H), 2.60 (m, 2H), 3.20 (m, 2H), 3.50 (m, 2H), 4.15 (s, 2H), 5.08 (d, 1H), 5.95 (d, 1H), 6.95 (s, 1H), 7.20–7.60 (m, 26H).

Example 46
(7R)-7-[(Z)-2-(2-Amino-5-chlorothiazol-4-yl)-2-(hydroxyimino)acetamido]-3-[2-amino-4-(2-aminoethylthiomethyl)-1,3-thiazol-5-ylthio]-3-cephem-4-carboxylate, Trifluoroacetic Acid Salt To a solution of (7R)-7-[(Z)-2-(2-amino-5-chlorothiazol-4-yl)-2-(triphenylmethoxyimino)acetamido]-3-[2-amino-4-(2-t-butyloxycarbonylaminoethylthiomethyl)-1,3-thiazol-5-ylthio]-3-cephem-4-carboxylate, diphenylmethyl ester (0.60 mg) in methylene chloride (20 mL) were added triethylsilane (0.5 mL) and trifluoroacetic acid (10 mL) at 0° C. After 30 min cooling was removed and stirring was continued for 1 hr at room temperature. Reaction mixture was concentrated under reduced pressure and the oily residue was triturated with diisopropyl ether and filtered to produce precipitate of the title product (0.41 g). $^1$H NMR (D$_2$O) δ 2.90 (t, J=6, 2H), 3.24 (t, J=6, 2H), 3.54 (d, J=16, 1H), 3.78 (d, J=16, 1H), 3.96 (s, 1H), 5.32 (d, J=6, 1H), 5.92 (d, J=6, 1H).

Example 47
1-(2-t-Butyloxycarbonylaminoethylthio)-3-chloropropan-2-one

To a stirred solution of 1,3-dichloroacetone (5.00 g, 39.37 mmol) in tetrahydrofuran (50 mL) were added 2-t-butyloxycarbonylaminoethanethiol (6.98 g, 37.50 mmol) and triethylamine (3.77 g, 37.50 mmol) at 0° C. After 3 hours the reaction mixture was partitioned between ethyl acetate and water. Organic layer was washed with 1 M hydrochloric acid, water, sodium bicatbonate solution and brine. Organic extract was dried over sodium sulfate and concentrated under reduced pressure to afford oily residue of title product (9.40 g). $^1$H NMR (CDCl$_3$) δ 1.58 (s, 9H), 2.76 (t, J=6, 2H), 3.40 (m, 2H), 3.58 (s, 2H), 4.42 (s, 2H), 5.00 (br s, 1H).

Example 48
4-(2-t-Butyloxycarbonylaminoethylthiomethyl)-2-mercapto-1,3-thiazole To a stirred solution of 1-(2-t-butyloxycarbonylaminoethylthio)-3-chloropropan-2-one (11.47 g, 42.8 mmol) in methanol (50 mL) was added ammonium dithiocarbamate (4.73 g, 42.9 mmol) at room temperature. After 50 hours the reaction mixture was partitioned between ethyl acetate and water.

Organic layer was extracted with dilute sodium hydroxide (100 mL, 0.4 M). Aqueous layer was then neutralized to pH=7.0 with dilute hydrochloric acid and extracted again with ethyl acetate. Organic extract was dried over sodium sulfate and concentrated under reduced pressure to afford yellow foam of title product (7.74 g), which was used for next step without further purification (all manipulations were performed under nitrogen to prevent formation of disulfide). $^1$H NMR (CDCl$_3$) δ 1.58 (s, 9H), 2.68 (t, J=6, 2H), 3.40 (m, 2H), 3.65 (s, 2H), 5.00 (br s, 1H), 6.60 (s, H).

Example 49

(7R)-7-Amino-3-[4-(2-t-butyloxycarbonylaminoethylthiomethyl)-1,3-thiazol-2-ylthio]-3-cephem-4-carboxylate, Diphenylmethyl Ester Solution of 4-(2-t-butyloxycarbonylaminoethylthiomethyl)-2-mercapto-1,3-thiazole (195 mg, 0.64 mmol) and (7R)-7-amino-3-methanesulfonyloxy-3-cephem-4-carboxylate, diphenylmethyl ester (295 mg, 0.64 mmol) in tetrahydrofuran (3 mL) and methanol (2 mL) was added tetrabutylammonium bromide (21 mg, 0.064 mmol) and aqueous sodium bicarbonate (4 mL, 0.5 M) and the mixture was stirred vigorously at room temperature. After 2 hours the reaction mixture was partitioned between ethyl acetate and water. Organic layer was dried over sodium sulfate and concentrated under reduced pressure and the residue was purified by radial chromatography on silica gel (ethyl acetate-hexane-40/60) to afford title product as yellow foam (27 mg). $^1$H NMR (CDCl$_3$) δ 1.58 (s, 9H), 2.75 (t, J=6, 2H), 3.40 (m, 2H), 3.50 (d, J=17, 1H), 3.80 (d, J=17, 1H), 3.90 (s, 2H), 4.90 (d, J=6, 1H), 5.05 (br s, 1H), 5.12 (d, J=6, 1H), 7.10 (s, 1H), 7.30–7.60 (m, 10H).

Example 50

(7R)-7-[(Z)-2-(2-tert-Butoxycarbonylaminopyrid-6-yl)-2-(triphenylmethoxyimino)acetamido]-3-(4-(2-tert-butoxycarbonylaminoethylthiomethyl)-1,3-thiazol-2-ylthio)-3-cephem-4-carboxylate, Benzhydryl Ester To a solution of [(Z)-2-(2-tert-butoxycarbonyl-aminopyrid-6-yl)-2-(triphenylmethoxyimino)acetic acid (40 mg, 0.074 mmol) in tetrahydrofuran (1 mL) cooled to 0° C. was added pyridine (30 mg, 0.38 mmol) followed by diphenylchlorophosphate (40 mg, 0.15 mmol). After TLC showed complete conversion to mixed anhydride, the solution was transferred into a flask containing a solution of (7R)-7-amino-3-[4-(2-t-butyloxycarbonylaminoethylthiomethyl)-1,3-thiazol-2-ylthio]-3-cephem-4-carboxylate, diphenylmethyl ester (10 mg, 0.015 mmol) in tetrahydrofuran (1 mL) cooled to −20° C. After 1 hour reaction at −20° C. the reaction mixture was partitioned between ethyl acetate and water. Organic layer was washed with 1 M hydrochloric acid, water, sodium bicarbonate solution and brine. Organic extract was dried over sodium sulfate and concentrated under reduced pressure to afford oily residue which was purified by radial chromatography on silica gel (1% methanol in methylene chloride) to afford protected cephem (10 mg). $^1$H NMR (CDCl$_3$/CD$_3$OD) δ 1.38 (s, 9H), 1.55 (s, 9H), 2.55 (t, J=6, 2H), 3.20 (m, 2H), 3.35 (d, J=17, 1H), 3.60 (d, J=17, 1H), 3.80 (s, 2H), 5.20 (d, J=6, 1H), 5.80 (br s, 1H), 6.10 (d, J=6, 1H), 6.95 (s, 1H) 7.10 (s, 1H), 7.10–7.40 (m, 27H), 7.45 (t, J=8, 1H), 7.80 (d, J=8, 1H).

Example 51

(7R)-7-[(Z)-2-(2-Aminopyrid-6-yl)-2-(hydroxyimino)acetamido]-3-(4-(2-aminoethylthiomethyl)-1,3-thiazol-2-ylthio)-3-cephem-4-carboxylate, Trifluoroacetic Acid Salt (7R)-7-[(Z)-2-(2-tert-Butoxycarbonylaminopyrid-6-yl)-2-(triphenylmethoxyimino)acetamido]-3-(4-(2-tert-butoxycarbonylaminoethylthiomethyl)-1,3-thiazol-2-ylthio)-3-cephem-4-carboxylate, benzhydryl ester was subjected to standard deprotection procedure to afford title product. $^1$H NMR (D$_2$O) δ 2.80 (t, J=6, 2H), 3.15 (t, J=6, 2H), 3.48 (d, J=17, 1H), 3.80 (d, J=17, 1H), 3.82 (s, 2H), 5.38 (d, J=6, 1H), 5.90 (d, J=6, 1H), 6.95 (d, J=8, 1H), 7.10 (d, J=8, 1H), 7.44 (s, 1H), 7.45 (t, J=8, 1H), 7.90 (t, J=8, 1H).

Example 52

2-(2-t-Butyloxycarbonylaminoethylthiomethyl)-5-mercapto-1,3,4-thiadiazole

To a solution of 2-mercapto-5-methyl-1,3,4-thiadiazole (1.00 g, 7.6 mmol) in tetrahydrofuran (60 mL) cooled to −78° C. was added n-butyllithium (6.1 mL, 15.2 mmol) and the reaction was stirred for 1 hour. The solution of bis(t-butyloxycarbonylaminoethyl)disulfide (2.64 g, 7.6 mmol) in tetrahydrofuran (10 mL) was added and after 1 hour at −78° C. reaction was continued for 16 hours at −20° C. Reaction mixture was partitioned between ethyl acetate and water. Aqueous layer was adjusted to pH=4.0 with dilute hydrochloric acid and extracted thoroughly with ethyl acetate. Organic extract was dried over sodium sulfate and concentrated under reduced pressure to afford oily residue, which was purified by flush chromatography on silica gel (1% methanol in methylene chloride) to produce the title product (0.37 g). $^1$H NMR (CDCl$_3$) δ 1.58 (s, 9H) 2.80 (t, J=6, 2H), 3.42 (m, 2H), 3.90 (s, 2H), 5.00 (s, 1H).

Example 53

(7R)-7-[(Z)-2-(2-Amino-5-chlorothiazol-4-yl)-2-(triphenylmethoxyimino)acetamido]-3-[2-(2-t-butyloxycarbonylaminoethylthiomethyl)-1,3,4-thiadiazol-5-ylthio]-3-cephem-4-carboxylate, Diphenylmethyl Ester To a solution of 2-(2-t-butyloxycarbonylaminoethylthiomethyl)-5-mercapto-1,3,4-thiadiazole (46 mg, 0.15 mmol), (7R)-7-[(Z)-2-(2-amino-5-chlorothiazol-4-yl)-2-(triphenylmethoxyimino)acetamido]-3-chloro-3-cephem-4-carboxylate, diphenyl ester (166 mg, 0.18 mmol) and tetrabutylammonium bromide (26 mg, 0.081 mmol) in methylene chloride (2 mL) at room temperature was added aqueous solution of sodium bicarbonate (0.5 mL, 0.5 M) and the reaction was stirred for 1 hour. Reaction mixture was partitioned between ethyl acetate and water. Organic extract was dried over sodium sulfate and concentrated under reduced pressure to afford oily residue, which was purified by repeated radial chromatography on silica gel (1% methanol in methylene chloride, then 50% ethylacetate in hexane) to produce title product (15 mg). $^1$H NMR (CDCl$_3$/CD$_3$OD) δ 1.42 (s, 9H), 2.63 (t, J=6, 2H), 3.30 (t, J=6, 2H), 3.42 (d, J=17, 1H), 3.75 (d, J=17, 1H), 4.05 (s, 2H), 5.20 (d, J=6, 1H), 6.14 (d, J=6, 1H), 7.02 (s, 1H), 7.10 (s, 1H), 7.10–7.40 (m, 25H).

Example 54

(7R)-7-[(Z)-2-(2-Amino-5-chlorothiazol-4-yl)-2-(hydroxyimino)acetamido]-3-[2-(2-aminoethylthiomethyl)-1,3,4-thiadiazol-5-ylthio]-3-cephem-4-carboxylate, Trifluoroacetic Acid Salt (7R)-7-[(Z)-2-(2-amino-5-chlorothiazol-4-yl)-2-(triphenylmethoxyimino)acetamido]-3-[2-(2-t-butyloxycarbonylaminoethylthiomethyl)-1,3,4-thiadiazol-5-ylthio]-3-cephem-4-carboxylate, diphenylmethyl ester was subjected to standard deprotection procedure to afford title product. $^1$H NMR (D$_2$O) δ 2.83 (t, J=6, 2H), 3.20 (t, J=6, 2H), 3.52 (d, J=17, 1H), 3.93 (d, J=17, 1H), 4.20 (s, 2H), 5.40 (d, J=6, 1H), 5.94 (d, J=6, 1H).

Example 55
N-Benzoyl-N'-(2-t-butyloxycarbonylaminoethyl)thiourea

To a stirred solution of 2-amino-(N-tert-butoxycarbonyl) ethylamine (1.96 g, 12.25 mmol) in methylene chloride (10 mL) at room temperature was added dropwise benzoyl isothiocyanate (2.20 g, 13.50 mmol). After 16 hours reaction product was isolated by loading crude reaction mixture on flash column to produce after chromatography pure title product as colorless solid (3.10 g). $^1$H NMR (CDCl$_3$) δ 1.60 (s, 9H), 3.60 (m, 2H), 3.98 (m, 2H), 4.95 (br s, 1H), 7.80–8.0 (m, 5H), 9.17 (br s, 1H).

Example 56
N-(2-t-Butyloxycarbonylaminoethyl)thiourea

N-benzoyl-N'-(2-t-butyloxycarbonylaminoethyl)thiourea (1.50 g, 0.44 mmol) was suspended in aqueous sodium hydroxide solution (22 mL, 2.0 M) and heated to 50° C. with stirring for 1 hour, which resulted in dissolution of starting material and consequent formation of precipitate. Reaction mixture was extracted with ethyl. acetate and the organic layer was dried over sodium sulfate and concentrated under reduced pressure to afford solid residue of title product (1.01 g), which was used for next step without further purification. $^1$H NMR (CDCl$_3$/CD$_3$OD) δ 1.40 (s, 9H), 3.20 (m, 4H), 3.55 (m, 2H).

Example 57
2-(2-t-Butyloxycarbonylaminoethylamino)-4-chloromethyl-1,3-thiazole A solution of N-(2-t-butyloxycarbonylaminoethyl) thiourea (1.00 g, 4.54 mol) in ethanol (22 mL) was added 1,3-dichloroacetone (2.60 g, 20.47 mmol) at room temperature. After 2 hours the reaction mixture was concentrated under reduced pressure. The residue was triturated with ether and filtered to afford the solid precipitate of title product (1.40 g), which was used for next step without further purification. $^1$H NMR (CDCl$_3$) δ 1.40 (s, 9H), 3.35 (m, 4H), 4.38 (s, 2H), 5.00 (br s, 1H), 6.40 (s, 1H).

Example 58
2-(2-t-Butyloxycarbonylaminoethylamino)-4-(2-t-butoxycarbonylaminoethylthiomethyl)-1,3-thiazole 2-(2-t-butyloxycarbonylaminoethylamino)-4-chloromethyl-1,3-thiazole was reacted with 2-t-butyloxycarbonylaminoethanethiol in a manner similar to that described in Example 42. $^1$H NMR (CDCl$_3$) δ 1.50 (s, 18H), 2.80 (m, 2H), 3.30–3.60 (m, 6H), 3.72 (s, 2H), 5.10 (br s, 1H), 5.40 (br s, 1H), 6.38 (s, 1H).

Example 59
2-(2-t-Butoxycarbonylaminoethylamino)-4-(2-t-butoxycarbonylaminoethylthiomethyl)-5-thiocyanato-3-thiazole 2-(2-t-butyloxycarbonylaminoethylamino)-4-(2-t-butoxycarbonylaminoethylthiomethyl)-1,3-thiazole was reacted with bromine and potassium thiocyanate in a manner similar to that described in Example 43 to produce title compound. $^1$H NMR (CDCl$_3$/CD$_3$OD) δ 1.40 (s, 18H), 2.62 (t, J=6, 2H), 3.20–3.35 (m, 6H), 3.68 (s, 2H), 5.75 (br s, 1H), 6.00 (br s, 1H).

Example 60
2-(2-t-Butoxycarbonylaminoethylamino)-4-(2-t-butoxycarbonylaminoethylthiomethyl)-5-mercapto-1,3-thiazole 2-(2-t-butoxycarbonylaminoethylamino)-4-(2-t-butoxycarbonylaminoethylthiomethyl)-5-thiocyanato-1,3-thiazole was reduced with sodium borohydride in a manner similar to that described in Example 44 to produce title compound.

Example 61
(7R)-7-[(Z)-2-(2-Amino-5-chlorothiazol-4-yl)-2-(triphenylmethoxyimino)acetamido]-3-[2-(2-t-butoxycarbonylaminoethylamino)-4-(2-t-butoxycarbonylaminoethylthiomethyl)-1,3-thiazol-5-ylthio]-3-cephem-4-carboxylate, Diphenylmethyl Ester 2-(2-t-butoxycarbonylaminoethylamino)-4-(2-t-butoxycarbonylaminoethylthiomethyl)-5-mercapto-1,3-thiazole was reacted with (7R)-7-[(Z)-2-(2-amino-5-chlorothiazol-4-yl)-2-(triphenylmethoxyimino)acetamido]-3-chloro-3-cephem-4-carboxylate, diphenylmethyl ester in a manner similar to that described in Example 45 to produce title compound. $^1$H NMR (CDCl$_3$/CD$_3$OD) δ 1.40 (s, 9H), 2.60 (t, J=6, 2H), 3.10–3.35 (m, 8H), 3.58 (s, 2H), 4.15 (s, 2H), 5.02 (d, J=6, 1H), 5.90 (d, J=6, 1H), 6.85 (s, 1H), 7.10–7.50 (m, 25H).

Example 62
(7R)-7-[(Z)-2-(2-Amino-5-chlorothiazol-4-yl)-2-(hydroxyimino)acetamido]-3-[2-(2-aminoethylamino)-4-(2-aminoethylthiomethyl)-1,3-thiazol-5-ylthio]-3-cephem-4-carboxylate, Trifluoroacetic Acid Salt (7R)-7-[(Z)-2-(2-amino-5-chlorothiazol-4-yl)-2-(triphenylmethoxyimino)acetamido]-3-[2-(2-t-butoxycarbonylaminoethylamino)-4-(2-t-butoxycarbonylaminoethylthiomethyl)-1,3-thiazol-5-ylthio]-3-cephem-4-carboxylate, diphenylmethyl ester was subjected to standard deprotection. Crude product was purified by reverse phase MPLC chromatography (Amberchrom CG-161, gradient of acetonitrile in 0.1% trifluoroacetic acid) and the fraction containing pure product was concentrated under reduced pressure and lyophilized to produce pure title product. $^1$H NMR (D$_2$O) δ 2.78 (t, J=6, 2H), 3.12 (m, 6H), 3.42 (d, J=17, 1H), 3.62 (d, J=17, 1H), 3.65 (m, 2H), 3.80 (s, 2H), 5.20 (d, J=6, 1H), 5.80 (d, J=6, 1H).

Example 63
3-t-Butylthio-2-hydroxymethylpyridine

To a suspension of 3-t-butylthio-2-carboxypyridine (10.0 g, 47.4 mmol) in tetrahydrofuran (200 mL) cooled to −5° C. was added trethylamine (8.25 mL, 47.4 mmol) followed by addition of ethyl chloroformate (4.38 g, 47.4 mmol) and reaction was stirred for 30 min at 0° C. Lithium borohydride (2.58 g, 118 mmol) was added in portions, maintaining the temperature below 5° C. After the addition was complete the reaction was allowed to warm to room temperature and stirred for 1 hour. Temperature was lowered to −5° C. and methanol (10 mL) was added followed by addition of aqueous sodium hydroxide (10 mL, 10%). After addition of ethyl acetate (50 mL) and water (40 mL) dilute hydrochloric acid was added to pH=5.0.

Precipitated inorganic salt was filtered off and organic layer of the filtrate was separated. After washing aqueous layer thoroughly with ethyl acetate combined organic extracts were dried over sodium sulfate and concentrated to produce yelow oil (7.21 g) of title product. $^1$H NMR (CDCl$_3$) δ 1.40 (s, 9H), 4.50 (br s, 1H), 4.90 (s, 2H), 7.20 (m, 1H), 7.80 (d, J=7, 1H), 8.55 (d, J=5, 1H), 1H.).

Example 64
3-t-Butylthio-2-(2-t-butoxycarbonylaminoethylthiomethyl)-pyridine A solution of Vilsmeier reagent was prepared by addition of thionyl chloride (1.09 g, 9.17 mmol) to dry dimethylformamide (10 mL) at room temperature. After 30 min. the above solution was transferred to a solution of 3-t-butylthio-2-hydroxymethylpyridine (1.20 g, 6.09 mmol) in dry dimethylformamide (5 mL).

After stirring for 30 min at room temperature powdered potassium carbonate (4.15 g, 30 mmol) was added followed by addition of 2-t-butoxycarbonylaminoethanethiol and sodium iodide (0.15 g, 1.05 mmol) and vigorous stirring was continued for 16 hours. Reaction mixture was partitioned between ethyl acetate and water. Organic extract was thoroughly washed with water, then dried over sodium sulfate and evaporated to produce oily residue, which was purified by flash chromatography on silica gel (ethyl acetate-hexane-1/2) to afford oily title product (1.10 g). $^1$H NMR (CDCl$_3$) δ 1.40 (s, 9H), 1.57 (s, 9H), 2.80 (t, J=6H, 2H), 3.43 (t, J=6H, 2H), 4.35 (s, 2H), 5.40 (br s, 1H), 7.28 (dd, J=6, J=4, 1H), 7.95 (d, J=6, 1H), 8.63 (d, J=4, 1H).

Example 65

2-(2-Aminoethylthiomethyl)-3-mercaptopyridine Dihydrochloride

A solution of 3-t-butylthio-2-(2-t-butoxycarbonylaminoethylthiomethyl)-pyridine (0.60 g) in hydrochloric acid (5 mL, 6.0 M) was refluxed for 3 days (until NMR of a sample in D$_2$O does not show any t-butyl signal) and the reaction mixture was evaporated to dryness to produce the desired solid dihydrochloride (0.40 g), which was used for next step without further purification. $^1$H NMR (D$_2$O) δ 2.85 (t, J=6H, 2H), 3.15 (t, J=6H, 2H), 4.20 (s, 2H), 7.62 (m, 1H), 7.30 (d, J=4, 1H), 7.43 (d, J=6, 1H).

Example 66 bis(2-(2-Aminoethylthiomethyl)pyrid-3-yl)disulfide

A solution of 2-(2-aminoethylthiomethyl)-3-mercaptopyridine dihydrochloride (0.40 g) in water (4 mL) basified with addition of concentrated ammonium hydroxide and a stream of air was bubbled through it for 16 hours. Reaction mixture was evaporated to dryness to produce solid residue of title product and ammonium chloride which was used for next step without further purification. $^1$H NMR (D$_2$O) δ 2.75 (t, J=6H, 2H), 3.15 (t, J=6H, 2H), 4.00 (s, 2H), 7.38 (dd, J=4, J=6, 1H), 8.21 (d, J=6, 1H), 8.38 (d, J=4, 1H).

Example 67 bis[2-(2-t-Butoxycarbonylaminoethylthiomethyl)pyrid-3-yl]disulfide

To a solution of crude bis(2-(2-aminoethylthiomethyl)pyrid-3-yl)disulfide (0.43 g, 1.08 mmol) in methanol (50 mL) were added di-t-butyldicarbonate (1.19 g, 5.46 mmol) and triethylamine (0.73 g, 7.20 mmol). After 45 min. at room temperature reaction mixture was evaporated to dryness and redissolved in methylene chloride. The insoluble residue was filtered off and the filtrate was concentrated under reduced pressure to produce oily residue. Flash chromatogaphy on silica gel (5% methanol in methylene chloride) yielded oily title product (0.28 g). $^1$H NMR (CDCl$_3$) δ 1.57 (s, 9H), 2.78 (t, J=6H, 2H), 3.40 (m, 2H), 4.12 (s, 2H), 5.20 (br s, 1H), 7.30 (dd, J=6, J=4, 1H), 8.03 (d, J=6, 1H), 8.48 (d, J=4, 1H).

Example 68

(7R)-7-[(Z)-2-(2-Amino-5-chlorothiazol-4-yl)-2-(triphenylmethoxyimino)acetamido]-3-[2-(2-t-butoxycarbonylaminoethylthiomethyl)pyrid-3-ylthio]-3-cephem-4-carboxylate, Diphenylmethyl Ester To a solution bis[2-(2-t-butoxycarbonylaminoethylthiomethyl)pyrid-3-yl]disulfide (83 mg, 0.14 mmol) in dimethylformamide (1 mL) and (7R)-7-[(Z)-2-(2-amino-5-chlorothiazol-4-yl)-2-(triphenylmethoxyimino)acetamido]-3-chloro-3-cephem-4-carboxylate, diphenylmethyl ester (175 g, 0.21 mmol) were added triphenyl phosphine (75 g, 0.28 mmol) and water (0.01 mL). After 3 hours at room temperature the reaction mixture was partitioned between water and ethyl acetate. Organic layer was dried over sodium sulfate and concentrated under reduced pressure to afford oily residue which was purified by radial chromatography on silica gel (2% methanol in methylene chloride) to yield title product (205 mg). $^1$H NMR (CDCl$_3$/CD$_3$OD) δ 1.40 (s, 9H), 2.60 (t, J=6, 2H), 3.12 (d, J=16, 1H), 3.25 (m, 3H), 3.90 (s, 2H), 5.18 (d, J=6, 1H), 6.00 (d, J=6, 1H), 6.98 (s, 1H), 7.20–7.60 (m, 2H), 7.70 (d, J=6, 1H), 8.42 (d, J=6, 1H).

Example 69

(7R)-7-[(Z)-2-(2-Amino-5-chlorothiazol-4-y)-2-(hydroxyimino)acetamido]-3-[2-(2-aminoethylthiomethyl)pyrid-3-ylthio]-3-cephem-4-carboxylate, Methanesulfonic Acid Salt (7R)-7-[(Z)-2-(2-amino-5-chlorothiazol-4-yl)-2-(triphenylmethoxyimino)acetamido]-3-[2-(2-t-butoxycarbonylaminoethylthiomethyl)pyrid-3-ylthio]-3-cephem-4-carboxylate, diphenylmethyl ester was subjected to standard deprotection. Crude product was dissolved in small volume of water and free zwitterion was isolated by loading the solution on HP20 reverse phase column, eluting with water until eluate become neutral and eluting of the product with water/acetonitrile mixture (60/40). The fractions containing pure product were evaporated to dryness under reduced pressure. The solid residue of zwitterionic product was converted into soluble methanesulfonate salt by stirring of a suspension in small volume of water and adding aqueous methanesulfonic acid until all material solubilized. Lyophilization of resulting solution produced methanesulfonate salt of title product. $^1$H NMR (D$_2$O) δ 2.55 (s, 5H), 2.66 (t, J=6, 2H), 3.21 (t, J=6, 2H), 3.30 (d, J=17, 1H), 3.74 (d, J=17, 1H), 4.20 (s, 2H), 5.33 (d, J=6, 2H), 5.88 (d, J=6, 1H), 7.80 (dd, J=4, J=6, 1H), 8.24 (d, J=6, 1H), 8.50 (d, J=4, 1H).

Example 70 bis{2-[2-N,N'-bis(t-Butoxycarbonyl)guanidinoethylthiomethyl]pyrid-3-yl}disulfide To a suspension of Bis(2-(2-aminoethylthiomethyl)pyrid-3-yl)disulfide (98 mg, 0.41 mmol) dimethylformamide was added 1-[N,N'-bis(t-butoxycarbonyl)carboxamidino]-1H-pyrazole (141 mg, 0.45 mmol) and the reaction was heated at 40° C. for 16 hours. Reaction mixture was partitioned between ethyl acetate and water. Organic extract was dried over sodium sulfate and concentrated under reduced pressure to afford oily residue which was purified by radial chromatography on silica gel (2% methanol in methylene chloride) to afford oily title product (140 mg). $^1$H NMR (CDCl$_3$) δ 1.60 (s, 18H), 2.80 (t, J=6, 2H), 3.72 (m, 2H), 4.07 (s, 2H), 7.25 (dd, J=6, J=4, 1H), 8.00 (d, J=6, 1H), 8.43 (d, J=4, 1H), 8.66 (br s, 1H).

Example 71

(7R)-7-[(Z)-2-(5-Amino-1,2,4-thiadiazol-3-yl)-2-(triphenylmethoxyimino)acetamido]-3-methanesulfonyloxy-3-cephem-4-carboxylate, Diphenylmethyl Ester To a suspension of (Z)-2-(5-amino-1,2,4-thiadiazol-3-yl)-2-(triphenylmethoxyimino)acetic acid (2.52 g, 4.00 mmol) and (7R)-7-amino-3-methanesulfonyloxy-3-cephem-4-carboxylate, diphenylmethyl ester, tosylate salt (1.71 g, 4.00 mmol) in tetrahydrofuran cooled to −50° C. was added diisopropylethylamine (1.54 g, 12.00 mmol) followed by phosphorous oxychloride (0.85 g, 5.60 mmol) and the reaction mixture was stirred for 1 hour at −30° to −35° C. Dilute hydrochloric acid was added to cold mixture and the reaction was allowed to reach room temperature. After partitioning between water and ethyl acetate the organic layer was thoroughly washed with dilute hydrochloric acid, brine, dried over sodium sulfate and filtered through a plug of silica gel to remove polar impurities. Removing of solvents under reduced pressure afforded yellowish foam of the title product (2.86 g). $^1$H NMR (CDCl$_3$/CD$_3$OD) δ 2.85 (s, 3H), 3.56 (d, J=16, 1H), 3.83 (d, J=16, 1H), 5.22 (d, J=6, 1H), 6.18 (d, J=6, 1H), 7.00 (s, 1H), 7.30–7.50 (m, 25H).

Example 72

(7R)-7-[(Z)-2-(5-Amino-1,2,4-thiadiazol-3-yl)-2-(triphenylmethoxyimino)acetamido]-3-{2-[2-N,N'-bis(t-butoxycarbonyl)guanidinoethylthiomethyl]pyrid-3-ylthio}-3-cephem-4-carboxylate, Diphenylmethyl Ester (7R)-7-[(Z)-2-(5-amino-1,2,4-thiadiazol-3-yl)-2-(triphenylmethoxyimino)acetamido]-3-methanesulfonyloxy-3-cephem-4-carboxylate, diphenylmethyl ester was reacted with di{2-[2-N,N'-bis(t-butoxycarbonyl)guanidinoethylthiomethyl]pyrid-3-yl}disulfide in a manner similar to that described for preparation of 67 to produce title compound. $^1$H NMR (CDCl$_3$/CD$_3$OD) δ 1.40 (s, 18H), 2.61 (t, J=6, 2H), 3.06 (d, J=16, 1H), 3.23 (d, J=16, 1H), 3.53 (t, J=6, 2H), 3.80 (s, 2H), 5.10 (d, J=6, 1H), 5.96 (d, J=6, 1H), 6.92 (s, 1H), 7.10–7.30 (m, 27H), 8.62 (d, J=6, 1H).

Example 73

(7R)-7-[(Z)-2-(5-Amino-1,2,4-thiadiazol-3-yl)-2-(hydroxyimino)acetamido]-3-{2-[2-guanidinoethylthiomethyl]pyrid-3-ylthio}-3-cephem-4-carboxylate, Trifluoroacetic Acid Salt To a solution of (7R)-7-[(Z)-2-(5-amino-1,2,4-thiadiazol-3-yl)-2-(triphenylmethoxyimino)acetamido]-3-{2-[2-N,N'-bis(t-butoxycarbonyl)guanidinoethylthiomethyl]pyrid-3-ylthio}-3-cephem-4-carboxylate, diphenylmethyl ester (200 mg) in methylene chloride (20 mL) were added triethyl silane (10 mL) and trifuloroacetic acid (0.5 mL) room temperature. After 40 min. reaction, the mixture was concentrated under reduced pressure and the oily residue was triturated with diisopropyl ether and filtered to produce precipitate of crude product. The resulting solid was dissolved in small amount of water and after filrering off insoluble material product was isolated from the filtrate by reverse phase MPLC chromatography (Amberchrom CG-161, gradient of acetonitrile in 0.1% trifluoroacetic acid). Fraction containing pure product was concentrated under reduced pressure and lyophilized to produce pure title product (25 mg). $^1$H NMR (D$_2$O) δ 2.80 (t, J=6, 2H), 3.30 (d, J=16, 1H), 3.38 (t, J=6, 2H), 3.75 (d, J=16, 1H), 4.21 (s, 2H), 5.35 (d, J=6, 1H), 5.89 (d, J=6, 1H), 7.88 (dd, J=4, J=6, 1H), 8.46 (d, J=6, 1H), 8.55 (d, J=4, 1H).

Example 74

(7R)-7-[(Z)-2-(2-Amino-5-chlorothiazol-4-yl)-2-(triphenylmethoxyimino)acetamido]-3-{2-[2-N,N'-bis(t-butoxycarbonyl)guanidinoethylthiomethyl]pyrid-3-ylthio)-3-cephem-4-carboxylate, Diphenylmethyl Ester Bis{2-[2-N,N'-bis(t-butoxycarbonyl)guanidinoethylthiomethyl]pyrid-3-yl}disulfide was reacted with (7R)-7-[(Z)-2-(2-amino-5-chlorothiazol-4-yl)-2-(triphenylmethoxyimino)acetamido]-3-chloro-3-cephem-4-carboxylate, diphenylmethyl ester in a manner similar to that described for preparation of 67 to produce title compound. $^1$H NMR (CDCl$_3$) δ 1.57 (s, 18H), 2.83 (m, 2H), 3.22 (d, J=16, 1H), 3.37 (d, J=16, 1H), 4.05 (d, J=10, 1H), 4.10 (d, J=10, 1H), 5.22 (d, J=6, 1H), 6.10 (m, 1H), 7.10 (s, 1H), 7.30–7.50 (m, 27H), 7.80 (d, J=6, 1H), 8.58 (d, J=4, 1H).

Example 75

(7R)-7-[(Z)-2-(2-Amino-5-chlorothiazol-4-yl)-2-(hydroxyimino)acetamido]-3-[2-(guanidinoethylthiomethyl)pyrid-3-ylthio]-3-cephem-4-carboxylate, Trifluoroacetic Acid Salt To a solution of (7R)-7-[(Z)-2-(2-amino-5-chlorothiazol-4-yl)-2-(triphenylmethoxyimino)acetamido]-3-{2-[2-N,N'-bis(t-butoxycarbonyl)guanidinoethylthiomethyl]pyrid-3-ylthio)-3-cephem-4-carboxylate, diphenylmethyl ester (160 mg, 0.128 mmol) in methylene chloride (5.0 mL) and triethylsilane (1.5 mL) colled to 0° C. was added trifluoroacetic acid (8.0 mL) and reaction was stirred at 10° C. for 7 hours. Reaction mixture was poured into ethyl ether cooled to −10° C. (80 mL) and the resulting precipitate was washed thoroughly with ether to produce solid of title product (90 mg). $^1$H NMR (D$_2$O) δ 2.80 (m, 2H), 3.05–3.2 (m, 3H), 3.78 (d, J=16, 1H), 4.12 (s, 1H), 5.38 (d, J=6, 1H), 5.92 (d, J=6, 1H), 7.85 (dd, J=4, J=6, 1H), 8.32 (d, J=6, 1H), 8.56 (d, J=4, 1H).

Example 76

(7R)-7-[(Z)-2-(5-Amino-1,2,4-thiadiazol-3-yl)-2-(triphenylmethoxyimino)acetamido]-3-[2-(t-butoxycarbonylaminoethylthiomethyl)pyrid-3-ylthio]-3-cephem-4-carboxylate, Diphenylmethyl Ester (7R)-7-[(Z)-2-(5-amino-1,2,4-thiadiazol-3-yl)-2-(triphenylmethoxyimino)acetamido]-3-methanesulfonyloxy-3-cephem-4-carboxylate, diphenylmethyl ester was reacted with di[2-(2-t-butoxycarbonylaminoethylthiomethyl)pyrid-3-yl]disulfide in a manner similar to that described for preparation of 67 to produce title compound. $^1$H NMR (CDCl$_3$/CD$_3$OD) δ 1.40 (s, 9H), 2.59 (t, J=6, 2H), 3.12 (d, J=16, 1H), 3.22 (m, 3H), 3.90 (s, 2H), 5.18 (d, J=6, 1H), 6.02 (d, J=6, 1H), 7.00 (s, 1H), 7.20–7.50 (m, 26H), 7.72 (d, J=6, 1H), 8.42 (d, J=6, 1H).

Example 77

(7R)-7-[(Z)-2-(5-Amino-1,2,4-thiadiazol-3-yl)-2-(hydroxyimino)acetamido]-3-[2-(aminoethylthiomethyl)pyrid-3-ylthio]-3-cephem-4-carboxylate, Methanesulfonic Acid Salt (7R)-7-[(Z)-2-(5-amino-1,2,4-thiadiazol-3-yl)-2-(triphenylmethoxyimino)acetamido]-3-[2-(t-butoxycarbonylaminoethylthiomethyl)pyrid-3-ylthio]-3-cephem-4-carboxylate, diphenylmethyl ester was subjected to standard deprotection. Crude product was dissolved in small volume of water and free zwitterion was isolated by loading the solution on HP20 reverse phase column, eluting with water until eluate become neutral and elution of the product with water/acetonitrile mixture (60/40). The fractions containing pure product were evaporated to dryness under reduced pressure. The solid residue of zwitterionic product was converted into soluble methanesulfonate salt by stirring suspension in small volume of water and addinq aqueous methanesulfonic acid until all material solubilized. Lyophilization of resulting solution produced methanesulfonate salt of title product. $^1$H NMR (D$_2$O) δ 2.70 (s, 2.5H), 2.80 (t, J=6, 2H), 3.15 (t, J=6, 2H), 3.21 (d, J=16, 1H), 3.68 (d, J=16, 1H), 4.10 (s, 2H), 5.29 (d, J=6, 2H), 5.83 (d, J=6, 1H), 7.65 (dd, J=4, J=6, 1H), 8.20 (d, J=6, 1H), 8.41 (d, J=4, 1H).

Example 78

2-Chloro-4-chloromethyl-5-(2-phenylsulfonylethyl)thio-1,3-thiazole

To a solution of 4-chloromethyl-5-(2-phenylsulfonylethyl)thio-1,3-thiazole (400 mg, 1.2 mmol) in N,N-dimethylformamide (3 mL) was added N-chlorosuccinimide (160 mg, 1.2 mmol), and the mixture was stirred at room temperature for 16 h. The resulting mixture was poured into water and extracted with ethyl acetate. The organic solution was washed with water, dried over sodium sulfate, and concentrated; The residue was chromatographed (silica gel, 20% ethyl acetate-hexane), affording 260 mg of the title compound. $^1$H NMR (CDCl$_3$) δ 3.09 (2H), 3.36 (2H), 4.60 (2H), 7.5–7.9 (5H).

Example 79
2-Chloro-4-[(2-N-tert-butoxycarbonylaminoethyl) thiomethyl]-5-(2-phenylsulfonylethyl)thio-1,3-thiazole A mixture of 2-chloro-4-chloromethyl-5-(2-phenylsulfonylethyl)thio-1,3-thiazole (260 mg, 0.71 mmol), sodium iodide (160 mg, 1.1 mmol), 2-aminoethanethiol hydrochloride (96 mg, 0.85 mmol), t-BOC anhydride (231 mg, 1.1 mmol), and sodium bicarbonate (178 mg, 2.1 mmol) in dioxane (6 mL) and water (4 mL) was stirred at room temperature for 16 h. The reaction mixture was diluted with ethyl acetate, washed with brine, and concentrated. The residue was chromatographed on silica gel (1% methanol/dichloromethane), affording 370 mg of the title compound. $^1$H NMR (CDCl$_3$) δ 1.46 (9H), 2.70 (2H), 3.06 (2H), 3.34 (4H), 3.80 (s, 2H), 4.96 (br s, 1H), 7.5–7.8 (5H).

Example 80
(7R)-7-Amino-3-[2-chloro-4-(2-N-tert-butoxycarbonyl-aminoethylthio)methyl-1,3-thiazol-5-ylthio]-3-cephem-4-carboxylate, Diphenylmethyl Ester To a solution of 2-chloro-4-[(2-N-tert-butoxycar-bonylaminoethyl)thiomethyl]-5-(2-phenylsulfonylethyl) thio-1,3-thiazole (140 mg, 0.30 mmol) in N,N-dimethylformamide (2 mL) was added potassium t-butoxide (40 mg, 0.35 mmol) and stirred at room temperature for 45 min and then cooled to 0° C. (7R)-7-Amino-3-methanesulfonyloxy-3-cephem-4-carboxylate 4-diphenylmethyl ester (170 mg, 0.37 mmol) was added. After stirring for 1 h at 0° C., the reaction was quenched with saturated aqueous ammonium chloride. The mixture was extracted with ethyl acetate, washed with aqueous lithium chloride solution, and concentrated after addition of p-toluenesulfonic acid (45 mg). The residue was triturated with diethyl ether, affording 200 mg of the crude title compound as its p-toluenesulfonic acid salt, which was used for the next reaction without further purification.

Example 81
(7R)-7-[(Z)-2-(2-tert-Butoxycarbonylaminopyrid-6-yl)-2-(triphenylmethoxyimino)acetamido]-3-[2-chloro-4-(2-N-tert-butoxycarbonylaminoethylthio)methyl-1,3-thiazol-5-ylthio]-3-cephem-4-carboxylate, Diphenylmethyl Ester To a cooled (−50° C.) solution of 2-(2-tert-butoxycarbonylaminopyrid-6-yl)-2-(triphenylmethoxy-imino)acetic acid sodium salt (186 mg, 0.34 mmol) in anhydrous N,N-dimethylformamide (2 mL) was added methanesulfonyl chloride (0.023 mL, 0.30 mmol), and stirred for 0.5 h. A solution of (7R)-7-amino-3-[2-chloro-4-(2-N-tert-butoxycarbonylaminoethylthio)methyl-1,3-thiazol-5-ylthio]-3-cephem-4-carboxylate, diphenylmethyl ester (200 mg, 0.23 mmol, obtained from the corresponding p-toluenesulfonic acid salt) and diisopropylethyl amine (0.12 mL, 0.68 mmol) was added, and stirred at −30° C. for an additional 2 h. The reaction was quenched with diluted hydrochloric acid. The mixture was then extracted with ethyl acetate, washed with aqueous lithium chloride, and concentrated. The residue was chromatographed on silica gel (0.5% methanol/dichloromethane), affording 86 mg of the title compound. $^1$H NMR (CDCl$_3$) δ 1.2–1.7 (18H), 2.65 (2H), 3.40 (4H), 3.82 (ABq, 2H), 4.85 (br s, 1H), 5.18 (d, 1H), 6.20 (dd, 1H), 6.95 (s, 1H), 7.2–8.1 (28H).

Example 82
(7R)-7-[(Z)-2-(2-Aminopyrid-6-yl)-2-(hydroxyimino) acetamido]-3-[2-chloro-4-(2-aminoethylthiomethyl)-1,3-thiazol-5-ylthio]-3-cephem-4-carboxylate, Trifluoroacetic Acid Salt To a mixture of (7R)-7-[(Z)-2-(2-tert-butoxycar-bonylaminopyrid-6-yl)-2-triphenylmethoxyimino) acetamido]-3-[2-chloro-4-(2-N-tert-butoxycarbonylamino-ethylthio)methyl-1,3-thiazol-5-ylthio]-3-cephem-4-carboxylate, diphenylmethyl ester (86 mg, 0.071 mmol), triethylsilane (0.3 mL) and dichloromethane (0.3 mL) was added trifluoroacetic acid (1.4 mL), and stirred at room temperature for 1 h. The mixture was concentrated to dryness and triturated with diethyl ether. The residue was purified by reverse-phase chromatography on Amberchrom column (eluting with 0% to 50% acetonitrile-water (containing 0.1% trifluoroacetic acid), affording 8 mg of the title compound. $^1$H NMR (D$_2$O) δ 3.11 (2H), 3.42 (2H), 3.70 (2H), 4.20 (2H), 5.50 (1H), 5.60 (1H), 7.20 (1H), 7.35 (1H), 8.18 (1H).

Example 83
Methyl 6-tert-Butoxycarbonylamino-2-pyridinecarboxylate

To a suspension of 2,6-pyridinedicarboxylic acid (8.35 g, 50 mmol) and triethylamine (5.05 g, 50 mmol) in tert-butyl alcohol (ca. 60 mL) was dropwise added diphenylphospho-ryl azide (13.8 g, 50 mmol), and the mixture was stirred at room temperature until the reaction mixture became a clear solution. The solution was then slowly heated and refluxed for 2.5 hour. After cooling, the mixture was partitioned between ethyl acetate-hexane (1:1, v/v) and 1% aqueous sodium hydroxide. The organic layer was washed again with 1% aqueous sodium hydroxide. All the aqueous solutions were combined and neutralized to pH=5 with concentrated hydrochloric acid in the presence of ethyl acetate. The ethyl acetate layer was washed with brine, dried over sodium sulfate and concentrated to obtain 5.0 g of 6-tert-butoxycarbonylamino-2-pyridinecarboxylic acid.

This acid (1.38 g, 5.8 mmol) was added to an ethyl acetate solution (20 mL) of Vilsmeier reagent (prepared from phos-phorus oxychloride (1.06 g, 6.9 mmol) and N,N-dimethylformamide (0.51 g, 6.9 mmol)) and stirred at 0° C. for 1 h. Anhydrous methanol (10 mL) was added, and the mixture was stirred for an additional 15 min. The mixture was then concentrated and partitioned between ethyl acetate and saturated aqueous sodium bicarbonate. The organic phase was washed with 1% aqueous lithium chloride and then brine, dried over sodium sulfate, and concentrated to afford 1.4 g of the title compound as a white crystalline solid. $^1$H NMR (CDCl$_3$) δ 1.51 (9H), 3.98 (3H), 7.54 (br s, 1H), 7.80 (2H), 8.16 (1H).

Example 84
Methyl 6-tert-Butoxycarbonylamino-2-pyridineglyoxylate

To a solution of methyl 6-tert-butoxycarbonylamino-2-pyridinecarboxylate (5.3 g, 21 mmol) and methyl methyl-sulfinylmethyl sulfide (3.7 g, 29 mmol) in N,N-dimethylformamide (15 mL) was added sodium hydride (60% in oil, 1.3 g, 34 mmol) at 0° C., and the mixture was stirred at room temperature for 2 h. Diethyl ether (100 mL) was added and the mixture was stirred for 30 min. The resulting precipitate was collected, dissolved in water, neu-tralized to pH=5 with 6% hydrochloric acid, and extracted with diethyl ether. The ether extract was dried and concentrated, to afford 3.5 g of the adduct.

This adduct was dissolved in dichloromethane (10 mL), and pyridine (3.1 g, 40 mmol) and trifluoroacetic anhydride (4.2 g, 20 mmol) were added at 0° C. After stirring at room temperature for 30 min, 0.5 M sodium methoxide in metha-nol (15 mL) was added. The mixture was then stirred for 1 h and concentrated. Extraction with ethyl acetate from aqueous sodium bicarbonate followed by evaporation afforded 3.7 g of the crude dithioorthoester.

The above crude (10 g) was dissolved in acetic acid (30 mL) and sodium perborate monohydrate (8.4 g, 84 mmol) was added. The resulting suspension was stirred for 2.5 h. The solvent was evaporated and ethyl acetate was added. The resulting solution was then washed with aqueous sodium bicarbonate, concentrated, and chromatographed (silica gel, dichloromethane) to afford 3.2 g of the title compound. $^1$H NMR (CDCl$_3$) δ 1.53 (9H), 3.98 (3H), 7.32 (br s, 1H), 7.77 (d, 1H), 7.86 (t, 1H), 8.24 (d, 1H).

Example 85
2-(2-tert-Butoxycarbonylaminopyrid-6-yl)-2-(triphenylmethoxyimino)acetic Acid To a solution of methyl 6-tert-butoxycarbonylamino-2-pyridineglyoxylate (1.6 g, 5.7 mmol) in 95% ethanol were added hydroxylamine hydrochloride (0.6 g, 8.6 mmol) and pyridine (0.96 mL, 9.7 mmol), and the mixture was stirred at room temperature for 1.5 h. The solvent was removed in vacuo and the oily residue was partitioned between ethyl acetate and water. The organic solution was washed with 3% hydrochloric acid and then water, dried over sodium sulfate, and concentrated to give 1.63 g of the crude hydroxyimino ester.

The crude ester was dissolved in dichloromethane and cooled to 0° C. Trityl chloride (1.87 g, 6.7 mmol) and triethylamine (0.84 mL, 6.7 mmol) were added and stirred for 2 h. The mixture was diluted with dichloromethane, washed with 1% hydrochloric acid and concentrated to afford 3.1 g of the tritylated ester. Crystallization from hexane-ethyl acetate provided the syn-oxyimino product that was free from the anti-isomer.

The above ester (4.25 g, 7.91 mmol) was dissolved in a mixed solvent of isopropyl alcohol, tetrahydrofuran and water (10:5:1, v/v/v) containing sodium hydroxide (0.64 g, 16 mmol) and was stirred at 65° C. for 1 h. The reaction mixture was concentrated to dryness, triturated with hexane, and partitioned between dichloromethane and diluted hydrochloric acid. The organic layer was concentrated, affording 3.7 g of the title compound. $^1$H NMR (CDCl$_3$) δ 1.53 (9H), 7.05–7.50 (16H), 7.55 (1H), 7.64 (1H).

Example 86
4-Chloromethyl-5-(2-phenylsulfonylethyl)thio-1,3-thiazole

Thionyl chloride (1.5 mL) was mixed with N,N-dimethylformamide (15 mL) and stirred at room temperature for 30 min. The resulting solution was then transferred via syringe to a solution of 4-hydroxymethyl-5-(2-phenylsulfonylethyl)thio-1,3-thiazole (1.69 g, 5.36 mmol) in N,N-dimethylformamide (5 mL). After 2 h, the mixture was partitioned between ethyl acetate and water. The organic solution was washed with 5% aqueous sodium bicarbonate, dried over sodium sulfate, and concentrated to dryness, affording 1.78 g of the title compound. $^1$H NMR (CDCl$_3$) δ 3.05 (2H), 3.35 (2H), 4.70 (2H), 7.50–7.85 (5H), 8.82 (s, 1H).

Example 87
4-[(2-tert-Butoxycarbonylaminoethyl)thiomethyl]-5-(2-phenylsulfonylethyl)thio-1,3-thiazole A mixture of 4-chloromethyl-5-(2-phenylsulfonylethyl)thio-1,3-thiazole (2.3 g, 6.9 mmol), sodium iodide (1.55 g, 10.3 mmol), 2-aminoethanethiol hydrochloride (0.94 g, 8.3 mmol), t-BOC anhydride (2.25 g, 10.3 mmol), sodium bicarbonate (1.74 g, 20.6 mmol) in dioxane (50 mL) and water (50 mL) was stirred at room temperature for 6 h. The reaction mixture was diluted with ethyl acetate, washed with brine, and concentrated. The residue was chromatographed on silica gel (1% methanol/dichloromethane), affording 2.9 g of the title compound. $^1$H NMR (CDCl$_3$) δ 1.42 (9H), 2.62 (2H), 3.05 (2H), 3.30 (4H), 3.87 (s, 2H), 5.03 (br s, 1H), 7.50–7.85 (5H), 8.80 (s, 1H).

Example 88
(7R)-7-Amino-3-(4-(2-tert-butoxycarbonylaminoethylthiomethyl)-1,3-thiazol-5-ylthio)-3-cephem-4-carboxylate, Benzhydryl Ester, p-Toluenesulfonic Acid Salt To a solution of 4-[(2-tert-butoxycarbonylaminoethyl)thiomethyl]-5-(2-phenylsulfonylethyl)thio-1,3-thiazole (260 mg, 0.55 mmol) in N,N-dimethylformamide (5 mL) was added potassium tert-butoxide in tetrahydrofuran (1 M, 0.5 mL), and the mixture was stirred at room temperature for 30 min. (7R)-7-amino-3-methanesufonyloxy-3-cephem-4-carboxylate, diphenylmethyl ester (freed from its p-toluenesulfonic acid salt form just prior to use, 314 mg, 0.5 mmol) was added and stirred for 1 h. The mixture was quenched with aqueous sodium bicarbonate, extracted with ethyl acetate, and then concentrated. The crude was chromatographed on silica gel, affording 185 mg of the free base, which was then treated with p-toluenesulfonic acid (52 mg) in ethyl acetate. Removal of the solvent yielded the title compound. $^1$H NMR of the free base (CDCl$_3$) δ 1.42 (9H), 2.64 (2H), 3.35 (4H), 3.94 (2H), 4.76 (1H), 4.92 (1H), 5.02 (br s, 1H), 6.98 (1H), 6.20–7.60 (10H), 8.93 (s, 1H).

Example 89
(7R)-7-[(Z)-2-(2-tert-Butoxycarbonylaminopyrid-6-yl)-2-(triphenylmethoxyimino)acetamido]-3-(4-(2-tert-butoxycarbonylaminoethylthiomethyl)-1,3-thiazol-5-ylthio)-3-cephem-4-carboxylate, Benzhydryl Ester To a solution of (7R)-7-amino-3-(4-(2-tert-butoxycarbonylaminoethylthiomethyl)-1,3-thiazol-5-ylthio)-3-cephem-4-carboxylate, benzhydryl ester, p-toluenesulfonic acid salt (232 mg, 0.28 mmol) and 2-(2-tert-butoxycarbonylaminopyrid-6-yl)-2-(triphenylmethoxyimino)acetic acid (173 mg, 0.33 mmol) in anhydrous tetrahydrofuran (30 mL) were sequentially added phosphorous oxychloride (0.04 mL, 0.41 mmol) and diisopropylethylamine (0.17 mL, 0.97 mmol) at −30° C. The resulting solution was stirred for 1.5 h and the reaction was quenched with 0.1% hydrochloric acid. The mixture was extracted with ethyl acetate and concentrated. The residue was then immediately chromatographed on silica gel (0.5% methanol/dichloromethane), affording 170 mg of the title compound. $^1$H NMR (CDCl$_3$) δ 1.37 (9H), 1.45 (9H), 2.63 (2H), 3.27 (4H), 3.85 (q, 2H), 5.12 (d, 1H, J=5), 5.21 (br s, 1H), 6.09 (1H), 6.97 (s, 1H), 7.12 (d, 1H, J=8), 7.22–7.42 (25H), 7.53 (1H), 7.80 (d, 1H, J=8), 8.89 (s, 1H).

Example 90
(7R)-7-[(Z)-2-(2-Aminopyrid-6-yl)-2-(hydroxyimino)acetamido]-3-(4-(2-aminoethylthiomethyl)-1,3-thiazol-5-ylthio)-3-cephem-4-carboxylate, Trifluoroacetic Acid Salt To a mixture of (7R)-7-[(Z)-2-(2-tert-butoxycarbonylaminopyrid-6-yl)-2-(triphenylmethoxyimino)acetamido]-3-(4-(2-tert-butoxycarbonylaminoethylthiomethyl)-1,3-thiazol-5-ylthio)-3-cephem-4-carboxylate, benzhydryl ester (91 mg, 0.08 mmol) and phenol (200 mg) at 45° C. was added methanesulfonic acid (17 mg, 0.18 mmol), and the mixture was stirred for 1.5 h. After cooling, diisopropyl ether was added. The resulting precipitate was collected, dissolved in water, and filtered. The filtrate was subjected to reverse phase chromatography on Amberchrom column (from 0 to 50% water (containing 0.1% trifluoroacetic acid)/acetonitrile) to give 18 mg of the title compound. $^1$H NMR (D$_2$O) δ 2.91 (2H), 3.30 (2H), 3.46 (d, 1H, J=18), 3.60 (d, 1H, J=18), 4.12 (2H), 5.35 (11H) 5.88 (1H), 7.02 (d, 1H, J=8), 7.17 (d, 1H, J=8), 7.98 (t, 1H, J=8), 9.20 (s, 1H).

Example 91
4-Hydroxymethyl-3-mercaptopyridine

To a suspension of 3-mercaptoisonicotinic acid (1.80 g, 11.6 mmol) in dry THF (70 mL) was added slowly borane in THF (52 mL, 1 M, 52 mmol) and the reaction mixture was stirred for 30 min. The solvent was evaporated under reduced pressure, methanol (40 mL) was added, and after gas evolution stopped, concentrated hydrochloric acid (3.6 mL) was added. The solution was filtered and the filtrate was evaporated to dryness. The residue was redissolved in a small volume of water, concentrated aqueous ammonia (3.6 mL) was added and the reaction mixture was evaporated to dryness. After overnight drying under vacuum, a quantitative yield of the title product was obtained, which was used for the next step without purification. $^1$H NMR (CD$_3$OD) δ 4.78 (s, 2H), 8.13 (d, 2H, J=6), 8.60 (d, 2H, J=6), 8.70 (s, 1H).

Example 92
3-(Triphenylmethylthio)-4-hydroxymethylpyridine 4-hydroxymethyl-3-mercaptopyridine (100 mg, 0.71 mmol) was dissolved in DMF (5 mL) and diisipropylethylamine (0.12 mL, 0.71 mmol) was added followed by triphenylmethylchloride (197 mg, 0.71 mmol). After 30 min. the reaction mixture was partitioned between water and ethyl acetate, and the organic layer was thoroughly washed with water and dried with anhydrous sodium sulfate. Purification by radial chromatography on silica gel produced pure title material (67 mg, 25% yield). $^1$H NMR (CDCl$_3$) δ 4.17 (s, 2H), 7.20–7.40 (m, 15H), 7.42 (d, 1H, J=6), 8.22 (s, 1H), 8.40 (d, 1H, J=6).

Example 93
4-{[(2-N-tert-Butoxycarbonylaminoethyl)thio]methyl}-3-(triphenylmethylthio)pyridine A solution of thionyl chloride (126 mg, 1.05 mmol) in dry DMF (2 mL) was stirred for 30 min. at room temperature. This solution was then cannulated into a solution of 3-(triphenylmethylthio)-4-hydroxymethylpyridine (270 mg, 0.70 mmol) in DMF (2 mL) at room temperature and the reaction was stirred for 30 min. 2-(N-t-butoxycarbonylaminoethyl)thiol (187 mg, 1.05 mmol) and powdered potassium carbonate (486 mg, 3.52 mmol) were added to the reaction mixture and stirring was continued for an additional 30 min. The reaction was partitioned between water and ethyl acetate and the organic layer was thoroughly washed with water and dried. After removing the solvent under reduced pressure the residue was purified by radial chromatography on silica gel (hexane/ethyl acetate-4/1) to yield the title material as an off-white solid (220 mg, 58%). $^1$H NMR (CDCl$_3$)δ 8 1.46 (s, 9H), 2.42 (t, 2H, J=6), 3.18 (s, 2H), 3.23 (m, 2H), 4.80 (br s, 1H), 7.10 (d, 1H, J=6), 7.20–7.45 (m, 15H), 8.28 (m, 2H).

Example 94
4-[(2-N-tert-Butoxycarbonylaminoethylthio)methyl]-3-(tert-butoxycarbonylthio)pyridine To 4-(2-N-t-butoxycarbonylaminoethylthiomethyl)-3-(triphenylmethylthio)pyridine (790 mg, 1.45 mmol) and triethylsilane (2 mL, 12.5 mmol) dissolved in methylene chloride (15 mL) was added trifluoroacetic acid (15 mL). After 1 hour stirring at room temperature, the reaction mixture was evaporated to dryness under reduced pressure and the residue was dissolved in dry tetrahydrofuran (10 mL). To this solution diisopropylethylamine (1.40 mL, 7.84 mmol) was added, followed by di-t-butyldicarbonate (1280 mg, 5.88 mmol), and after 3 hr. reaction at room temperature the solvent was removed at reduced pressure. Purification on silica gel by radial chromatography (methylene chloride/methanol-50/1) produced pure title product as a yellow foam (460 mg, 79%). $^1$H NMR (CDCl$_3$) δ 1.42 (s, 9H), 1.50 (s, 9H), 2.58 (t, 2H, J=6), 3.23 (t, 2H, J=6), 3.84 (s, 2H), 4.95 (br s, 1H), 7.42 (d, 1H, J=6), 8.58 (d, 1H, J=6), 8.70 (s, 1H).

Example 95
4-(2-N-t-Butoxycarbonylaminoethylthiomethyl)-3-mercaptopyridine

To a solution of 4-(2-N-t-butoxycarbonylaminoethylthiomethyl)-3-(tert-butoxycarbonylthio)pyridine (415 mg, 1.04 mmol) in methanol (2 mL) was added under nitrogen a methanolic solution of sodium methoxide (1.04 mL, 1.0 M), and the reaction mixture was heated at 50 for 30 min. After evaporating the solvent in vacuum the reaction was partitioned between water and ethyl acetate with addition of acetic acid (125 mg, 2.08 mmol). Evaporation of the solvent under reduced pressure yielded the title material (298 mg, 96% yield) which was used in the next step without further purification. $^1$H NMR (CD$_3$OD) δ 1.42 (s, 9H), 2.60 (m, 2H), 3.20 (m, 2H), 4.0 (s, 2H), 4.95 (br s, 1H), 7.52 (d, 1H, J=6), 8.00 (d, 1H, J=6), 8.40 (s, 1H).

Example 96
(7R)-7-[(Z)-2-(2-Amino-5-chlorothiazol-4-yl)-2-(triphenylmethoxyimino)acetamido]-3-[4-(N-tert-butoxycarbonylaminoethylthio)pyrid-3-ylthio]-3-cephem-4-carboxylate, Diphenylmethyl Ester To a solution of 4-(2-N-t-butoxycarbonylaminoethylthiomethyl)-3-mercaptopyridine (298 mg, 0.99 mmol) in ethyl acetate (5 mL) was added (7R)-7-[(Z)-2-(2-amino-5-chlorothiazol-4-yl)-2-(triphenylmethoxyimino)acetamido]-3-methanesulfonyloxy-3-cephem-4-carboxylate diphenylmethyl ester. After 1 hour stirring at room temperature the reaction was partitioned between ethyl acetate and dilute sodium bicarbonate solution (30 mL, 1%). The organic layer was dried over anhydrous sodium sulfate and was evaporated under reduced pressure. The residue was purified by radial chromatography on silica gel to yield pure title product (366 mg, 33%). $^1$H NMR (CD$_3$OD) δ 1.40 (s, 9H), 2.50 (m, 2H), 3.20 (m, 2H), 3.12 (d, 1H, J=16) 3.80 (s, 2H), 3.38 (d, 1H, J=16), 5.25 (d, 1H, J=6), 6.00 (d, 1H, J=6), 7.00 (s, 1H), 7.20–7.40 (m, 25H), 7.42 (d, 1H, J=6) 8.40 (d, 1H, J=6), 8.50 (s, 1H).

Example 97
(7R)-7-[(Z)-2-(2-Amino-5-chlorothiazol-4-yl)-Z-(hydroxyimino)acetamido]-3-(4-aminoethylthiopyrid-3-ylthio)-3-cephem-4-carboxylate, Trifluoroacetic Acid Salt To a suspension of (7R)-7-[(Z)-2-(2-amino-5-chlorothiazol-4-yl)-2-(triphenylmethoxyimino)acetamido]-3-[4-(N-tert-butoxycarbonylaminoethylthio)pyrid-3-ylthio]-3-cephem-4-carboxylate, diphenylmethyl ester (342 mg, 0.31 mmol) in methylene chloride (3.5 mL) was added triethylsilane (1.7 mL, 4.06 mmol) followed by addition of trifluoroacetic acid (4.5 mL). After stirring at room temperature for 1 hr. the reaction was cooled to 0° C. and isopropyl ether (30 mL) was added. Stirring was continued at 0° C. for 10 min and the resulting precipitate was filtered and washed thoroughly with diisopropyl ether and dried in vacuum, yielding the title deprotected cephem bis-trifluoroacetate salt (222 mg, 85%). $^1$H NMR (D$_2$O) δ 2.90 (t, 2H, J=6), 3.31 (t, 2H, J=6), 3.43 (d, 1H, J=17), 3.85 (d, 1H, J=17), 4.18 (s, 2H), 5.43 (d, 1H, J=4.5), 5.97 (d, 1H, J=4.5), 8.10 (d, 1H, J=6), 8.66–8.68 (m, 2H).

The following compounds were also prepared by methods essentially analogous to those used for preparation of the compounds described above:

Example 98
(7R)-7-[(Z)-2-(5-Amino-1,2,4-thiadiazol-3-yl)-2-(hydroxyimino)acetamido]-3-[2-2-aminoethylthiomethyl)pyrid-4-ylthio]-3-cephem-4-carboxylate, Trifluoroacetic Acid Salt $^1$H NMR (CD$_3$OD) δ 2.90 (t, 2H, J=6), 3.27 (t, 2H, J=6), 3.47 (d, 1H, J=18), 4.08 (s, 2H), 5.49 (d, 1H, J=5), 6.11 (d, 1H, J=5), 7.66 (d, 1H, J=6), 8.55 (d, 1H, J=6), 8.69 (s, 1H).

Example 99
(7R)-7-[(Z)-2-(2-Aminopyrid-6-yl)-2-(hydroxyimino)acetamido]-3-[2-(2-aminoethylthio)-1,3,4-thiadiazol-5-ylthio]-3-cephem-4-carboxylate, Trifluoroacetic Acid Salt $^1$H NMR (D$_2$O) δ 3.20 (t, J=6, 2H), 3.42 (t, J=6, 2H), 3.30 (d, J=17, 1H), 3.80 (d, J=17, 1H), 5.42 (d, J=6, 1H), 6.00 (d, J=6, 1H), 7.03 (d, J=8, 1H), 7.20 (t, J=8, 1H), 8.00 (t, J=8, 1H).

Example 100
(7R)-7-[(Z)-2-(2-Aminopyrid-6-yl)-2-(hydroxyimino)acetamido]-3-[3-(2-aminoethylthiomethyl)pyrid-4-ylthio]-3-cephem-4-carboxylate, Trifluoroacetic Acid Salt

Example 101
(7R)-7-[(Z)-2-(5-Amino-1,2,4-thiadiazol-3-yl)-2-(hydroxyimino)acetamido]-3-[3-(2-guanidinoethylthiomethyl)pyrid-4-ylthio]-3-cephem-4-carboxylate, Trifluoroacetic Acid Salt $^1$H NMR (CD$_3$OD) δ 2.93 (s, 3H), 2.95 (t, 2H, J=6), 3.57 (d, 1H, J=18), 3.59 (t, 2H, J=6), 4.13 (d, 1H, J=18), 5.58 (d, 1H, J=5), 6.21 (d, 1H, J=5), 7.83 (d, 1H, J=6), 8.68 (d, 1H, J=6), 8.84 (s, 1H).

Example 102
(7R)-7-[(Z)-2-(2-Amino-5-chlorothiazol-4-yl)-2-(hydroxyimino)acetamido]-3-[2-amino-4-(2-guanidinoethylthiomethyl)-1,3-thiazol-5-ylthio]-3-cephem-4-carboxylate, Trifluoroacetic Acid Salt

Example 103
(7R)-7-[(Z)-2-(5-Amino-1,2,4-thiadiazol-3-yl)-2-(hydroxyimino)acetamido]-3-[4-(2-aminoethylthiomethyl)pyrid-3-ylthio]-3-cephem-4-carboxylate, Trifluoroacetic Acid Salt $^1$H NMR (CD$_3$OD) δ 2.85 (t, 2H, J=9), 3.33 (t, 2H, J=9), 3.43 (d, 1H, J=24), 3.78 (d, 1H, J=24), 4.18 (d, 2H, J=5), 5.32 (d, 1H, J=7), 5.94 (d, 1H, J=7), 8.11 (d, 1H, J=7), 8.72 (d, 1H, J=8), 8.77 (s, 1H).

Example 104
(7R)-7-[(Z)-2-(2-Aminopyrid-6-yl)-2-(hydroxyimino)acetamido]-3-[4-(2-aminoethylthiomethyl)pyrid-3-ylthio]-3-cephem-4-carboxylate, Trifluoroacetic Acid Salt $^1$H NMR (CD$_3$OD) δ 2.68 (t, 2H, J=9), 3.09 (t, 2H, J=9), 2.41 (2H, J=23), 3.90 (s, 2H), 5.22 (d, 1H, J=6), 5.81 (d, 1H, J=6), 6.88 (d, 1H, J=9), 6.98 (d, 1H, J=10), 7.70 (s, 1H), 7.82 (t, 1H, J=9), 8.41 (d, 1H, J=7), 8.55 (d, 1H, J=7).

Example 105
2-(5-Ethoxycarbonylamino-1,2,4-thiadiazol-3-yl)acetic Acid

Into a 5 L round bottom flask equipped with mechanical stirrer, thermometer and nitrogen purge was charged a mixture of 2-(5-ethoxycarbonylamino-1,2,4-thiadiazol-3-yl)acetaldehyde and its dimethyl acetal (200 g) followed by acetic acid (1.2 L) and water (30 mL). The slurry was slowly heated to 30–35° C. and maintained at this temperature until complete conversion of the dimethyl acetal to the aldehyde was confirmed by proton NMR analysis. The solution was cooled to 15–20° C. and a 30% solution of peracetic acid was charged dropwise over 45 minutes. The solution was allowed to warm to 20° C. and then stirred at this temperature overnight. The white crystals which had formed overnight were collected by vacuum filtration and washed with cold ethyl acetate (3×250 mL). The solid was dried under high vacuum at 20° C. for 12 hours to give 141 grams of the title compound. $^1$H NMR (DMSO): δ 1.42 (t, 3H); 3.84 (s, 3H); 4.40 (q, 2H); 12.70 (bs, 1H).

Example 106
Methyl-2-(5-ethoxycarbonylamino-1,2,4-thiadiazol-3-yl)acetate

Into a 3 L round bottom flask equipped with mechanical stirrer, thermometer and nitrogen purge was charged 2-(5-ethoxycarbonylamino-1,2,4-thiadiazol-3-yl)acetic acid (185 g, 0.80 mol, 1.0 eq.) followed by methanol (925 mL) and the resulting solution was cooled to 0° C. To the solution was bubbled in HCl gas for 30 minutes and the thinning slurry was allowed to stir overnight at 20° C. Proton NMR analysis shows complete conversion to the title compound. The solvent was removed by rotary evaporation to 400 mL and then cooled to 0° C. and seeded with pure title compound. The thickening reaction mixture was stirred at 0° C. for two hours and the white solid was collected by vacuum filtration. The solid was dried under high vacuum for 12 hours at 20° C. to give 172.2 grams of the title compound as an off white solid. $^1$H NMR (CD$_3$OD): δ 1.47 (t, 3H); 3.83 (s, 3H); 3.97 (s, 2H); 4.45 (q, 2H).

Example 107
Methyl 2-(5-Ethoxycarbonylamino-1,2,4-thiadiazol-3-yl)-bromoacetate Into a 1 L round bottom flask was charged methyl 2-(5-ethoxycarbonylamino-1,2,4-thiadiazol-3-yl)acetate (50.0 g, 0.204 mol, 1.0 eq) followed by methanol (500 mL). The resulting slurry was cooled to 0° C. To the cooled slurry was charged a pre-made solution of bromine (9.9 mL, 0.194 mol, 0.95 eq) in methanol (100 mL) dropwise over 30 minutes maintaining the temperature between 0–5° C. The cold bath was removed and the solution was allowed to warm to room temperature and stirred for two hours. Proton NMR analysis of the reaction mixture showed reaction completion. The orange solution was evaporated to an orange oil. The orange oil was taken up in diethyl ether (400 mL) and the organic was washed with water (2×100 mL), saturated 1:1 NaHCO$_3$/Na$_2$S$_2$O$_4$ (2×100 mL) and then brine (100 mL). The clear colorless ether layer was dried with sodium sulfate, filtered and evaporated in vacuo to give 54.5 grams of the title compound as a clear colourless oil. $^1$H NMR (CDCl$_3$) δ 1.38 (t, 3H); 3.98 (s, 3H); 4.55 (q, 2H); 5.81 (s, 1H).

Example 108
Methyl 2-(5-Ethoxycarbonylamino-1,2,4-thiadiazol-3-yl)-oxoacetate Into a 1 L round bottom flask equipped with mechanical stirring and reflux condenser was charged methyl 2-(5-ethoxycarbonylamino-1,2,4-thiadiazol-3-yl)-bromoacetate (50.0 g, 0.154 mol, 1.0 eq.) followed by acetonitrile (500 mL). To the clear light yellow solution was charged pyridine N-oxide (37.0 g, 0.385 mol, 2.5 eq) and the reaction mixture was heated to reflux and maintained there for three hours until reaction completion was determined by proton NMR analysis. The solution was cooled and the acetonitrile was removed by rotary evaporation to give a thin yellow oil. The oil was dissolved in dichloromethane (500 mL) and the organic was washed once with brine (1×200 mL). The brine solution was extracted several times with dichloromethane (5×100 mL) and the organic layers were combined and dried with sodium sulfate, filtered and the solvent evaporated to give a clear slightly yellow oil which solidified upon standing at room temperature. The solid was dried under high vacuum to give 37.36 grams of the title compound. $^1$H NMR (CDCl$_3$) δ 1.40 (t, 3H); 4.06 (s, 3H); 4.46 (q, 2H).

Example 109
Methyl 2-(5-Ethoxycarbonylamino-1,2,4-thiadiazol-3-yl)-oxyiminoacetate Into a 1 L round bottom flask equipped with mechanical stirrer and nitrogen purge was charged methyl 2-(5-ethoxycarbonylamino-1,2,4-thiadiazol-3-yl)-oxoacetate. (50.0 g, 0.193 mol., 1.9 eq) followed by ethanol (500 mL). To the clear solution was charged hydroxylamine hydrochloride (20.0 g, 0.290 mol, 1.5 eq) followed by pyridine (23.5 mL, 0.290 mol, 1.5 eq) and the resulting light orange coloured solution was allowed to stir overnight at 20° C. The solvent was then evaporated to give a thin oil which was taken up in ethyl acetate (400 mL) and the organic was washed with water (2×100 mL), 5% HCl (100 mL) and then brine (100 mL). The organic was dried with sodium sulfate, filtered and evaporated under vacuum to give 40.93 grams of the title compound, as a white solid. $^1$H NMR (CDCl$_3$): 1.25 (t, 3H), 3.86 (s, 3H), 4.23 (q, 2H).

Example 110
(Z)-Methyl-2-(5-ethoxycarbonylamino-1,2,4-thiadiazol-3-yl)-2-triphenylmethyl-oxyiminoacetate Into a 1 L round bottom flask equipped with a mechanical stirrer and nitrogen purge was charged methyl 2-(5-ethoxycarbonylamino-1,2,4-thiadiazol-3-yl)-oxyiminoacetate (40.0 g, 0.146 mol, 1.0 eq) followed by dichloromethane (400 mL). The clear solution was cooled to 0° C. at which time triphenylmethylchloride (40.7 g, 0.146 mol, 1.0 eq) was charged followed by dropwise addition of triethylamine (20.3 mL, 0.146 mol, 1.0 eq). The solution was allowed to warm to room temperature and maintained there for two hours. To the reaction solution was charged water (200 mL) and the phases were separated. The organic phase was washed with water (2×100 mL) and then brine (2×100 mL), dried with sodium sulfate, filtered and evaporated under reduced pressure to a volume of 100 mL where it was allowed to stand in the refrigerator overnight. The crystals which had formed overnight were collected and washed with dichloromethane. Proton NMR analysis showed the crystals to be a 20:1 mixture of syn/anti tritylated oximes. The white solid was suspended in 320 mL of dichloromethane and refluxed gently until total dissolution was apparent. The clear solution was slowly cooled in the freezer and was seeded with pure syn isomer at 10° C. After standing overnight in the freezer the white solid which had formed was filtered and washed with cold dichloromethane. $^1$H NMR and TLC analysis showed this 53.1 grams of material to be the title compound. $^1$H NMR (CDCl$_3$) δ 1.41 (t, 3H); 4.05 (s, 3H); 4.31 (q, 2H); 7.25–7.45 (m, 15H).

Example 111
(Z)-2-(5-Amino-1,2,4-thiadiazol-3-yl)-2-triphenylmethyl-oxyimino Acetic Acid Into a 500 mL round bottom flask equipped with mechanical stirrer, reflux condenser and nitrogen purge was charged (Z)-methyl-2-(5-ethoxycarbonylamino-1,2,4-thiadiazol-3-yl)-triphenylmethyloxyiminoacetate (20.0 g, 0.04 mol, 1.0 eq) followed by 200 mL of a 2:1 solution of 2.5 M NaOH/ethanol. The resulting biphasic solution was heated to reflux and maintained there for 15 hours. The solution was cooled to 5° C. and the pH was slowly adjusted to 3–3.5 with concentrated HCl. The precipitated white solid was filtered and washed with cold water (3×100 mL). Removal of water by coevaporation with toluene (3×200 mL), followed by drying under high vacuum at 40° C. gave 15.44 grams of the title compound as a white fluffy solid. $^1$H NMR (DMSO) δ 7.20–7.45. Mass spectral analysis confirms product identity.

Example 112
7-Amino-3-chloro-3-cephem-4-carboxylate, t-Butylester

Into a 3 L round bottom flask equipped with magnetic stirrer, thermometer and nitrogen purge was charged 7-amino-3-chloro-3-cephem-4-carboxylic acid (97.8 g, 0.418 mol, 1.0 eq.) followed by t-butyl acetate (1 L). To the solution was added BF$_3$ etherate (317 mL, 2.51 mol, 6 eq.) dropwise over 20 minutes and the reaction mixture was stirred at 20° C. for two hours. The reaction mixture was poured into 2.5 L of ice/water. The layers were separated and the aqueous layer was cooled to 5° C. and the pH was adjusted to 6–7 with the addition of 2 M NaOH (approximately 2 L). The aqueous layer was extracted with ethyl acetate (3×300 mL) and the organic layers were combined and washed with brine (2×200 mL). A pre-made solution of p-TSA (70.7 g, 0.372 mol, 0.9 eq.) in ethyl acetate (1.4 L) was added and immediately a white solid began to precipitate out of solution. The solvent was evaporated to 500 mL (5 volumes on the starting I), was cooled to 10° C. and was allowed to stir at this temperature for 30 minutes. The white solid was vacuum filtered and the filter cake was washed with ethyl acetate (3×150 mL). The white solid was dried under high vacuum at 20° C. for 16 hours to give 117 grams of the title compound. $^1$H NMR (CD$_3$OD) δ 1.65 (s, 9H); 2.47 (s, 3H); 3.85 (d, 1H); 4.15 (d, 1H); 5.27 (d, 1H), 5.44 (d, 1H); 7.37 (d, 2H); 7.81 (d, 2H).

Example 113
(7R)-7-[(Z)-2-(5-Amino-1,2,4-thiadiazol-3-yl)-2-(triphenylmethoxyimino)acetamido-3-chloro-3-cephem-4-carboxylate, t-Butyl Ester Into a 1 L round bottom flask equipped with mechanical stirrer, thermometer and nitrogen purge was charged 7-amino-3-chloro-3-cephem carboxylate, t-butyl ester (15 g, 0.036 mol, 1 eq.) followed by (Z)-2-(5-amino-1,2,4-thiadiazol-3-yl)-2-(triphenylmethoxyimino)acetic acid (15 g, 0.036 mol, 1 eq.) and THF (350 mL) and the slurry was cooled to −35° C. at which time Hunig's base (13.93 g, 0.108 mol, 3.0 eq) was charged dropwise over 5 minutes maintaining the solution temperature between −30° C. to −35° C. To the now clear light yellow solution was charged phosphorous oxychloride (8.29 g, 0.054 mol, 1.5 eq.) dropwise over 10 minutes, maintaining the solution temperature between −30° C. and −35° C. The solution was allowed to stir at −35° C. for one hour until reaction completion was determined by TLC analysis (1:1 ethyl acetate-hexane). To the reaction solution was charged cold water (150 mL) followed by ethyl acetate (200 mL). The organic layer was separated and the aqueous layer was extracted with ethyl acetate (2×75 mL). The organic layers were combined and were washed with 0.5 M HCl (100 mL), water (2×200 mL) and brine (2×200 mL). The organic layer was dried with sodium sulfate, filtered and evaporated to dryness. The white solid was taken up in 30 mL of ethyl acetate and was poured into rapidly stirring hexane (400 mL) to give a white precipitated solid. The solid was vacuum filtered and the filter cake was washed with hexane (3×30 mL). The white solid was dried under high vacuum at 20° C. for 16 hours to give 17.9 grams of the title compound. $^1$H NMR (CDCl$_3$) δ

1.62 (s, 9H); 3.50 (d, 1H); 3.85 (d, 1H); 5.20 (d, 1H); 6.15 (q, 1H); 6.60 (d, 1H); 7.43 (m, 15H).

Example 114
3-Triphenylmethylthio-2-hydroxymethylpyridine

Into a 3 L round bottom flask equipped with mechanical stirrer and nitrogen purge was charged 3-mercapto-2-hydroxymethylpyridine hydrochloride (25.0 g, 0.141 mol, 1 eq.) followed by DMF (1.2 L) and to the cloudy suspension was charged finely powdered potassium carbonate (58.5 g, 0.423 mol, 3.0 eq.). To the resulting solution was charged triphenylmethylchloride (38.1 g, 0.137 mol, 0.97 eq) and the reactions mixture was allowed to stir at room temperature for three hours until TLC analysis showed reaction completion (ethyl acetate-hexanes). The DMF solution was poured into 3 L of 4:1 water/ethyl acetate. The aqueous layer was separated and extracted an additional time with ethyl acetate (200 mL). The organics were combined and hexane (150 mL) was added. The organic layer was washed with water (2×200 mL) then brine (2×200 mL). The organic layer was dried with sodium sulfate, filtered and evaporated in vacuo to give 48.63 g of the title compound as a brown oil which was taken directly on to the next reaction. $^1$H NMR (CDCl$_3$) δ 5.05 (s, 2H); 7.1–7.4 (m, 16H); 8.20 (d, 1H); 8.58 (d, 1H).

Example 115
3-Triphenylmethylthio-2-(N-t-butoxycarbonylamino-ethylthiomethyl)pyridine Into a 3 L round bottom flask equipped with a mechanical stirrer, thermometer and nitrogen purge was charged 3-triphenylmethylthio-2-hydroxymethylpyridine (40.0 g, 0.104 mol, 1 eq.) followed by DMF (1.2 L). The solution was cooled to 0° C. and a pre-formed solution of thionyl chloride (12.4 g, 0.104 mol, 1.0 eq.) in DMF (200 mL) was charged dropwise over approximately 5 minutes. To this orange coloured solution was charged BOC-cysteamine (18.4 g, 0.104 mol, 1 eq.) followed by finely powdered potassium carbonate (43.1 g, 0.104 mol, 1 eq) and the resulting suspension was vigorously stirred for two hours until TLC analysis showed reaction completion (1:1 EtOAc/hexanes). The solution was poured into a 3 L of a 4:1 mixture of ice water/4:1 ethyl acetate-hexane. The aqueous was separated and extracted with an additional 200 mL of 4:1 ethyl acetate-hexane. The organics were combined and washed with water (2×200 mL) then brine (2×200 mL). The organic layer was dried with sodium sulfate, filtered and the solvent was removed in vacuo to give 54 grams of a brown oil. This oil was purified by column chromatography on silica gel to give 41 grams of the title compound as a light yellow oil. $^1$H NMR (CDCl$_3$) δ 1.41 (s, 9H); 2.77 (t, 2H); 3.42 (t, 3H); 4.11 (s, 2H); 7.05–7.45 (m, 16H); 8.22 (d, 1H); 8.65 (d, 1H).

Example 116
3-Mercapto-2-(aminoethylthiomethyl)pyridine Trifluoroacetate

Into a 1 L round bottom flask equipped with a mechanical stirrer, thermometer and nitrogen purge was charged 3-triphenylmethylthio-2-(t-butoxycarbonylaminoethyl-thiomethyl)pyridine (40.0 g, 0.074 mol, 1 eq) followed by dichloromethane (200 mL). The light yellow solution was cooled to 0° C. and triethylsilane (60 mL) was added followed by dropwise addition of trifluoroacetic acid (200 mL) over approximately five minutes. The cold bath was removed and the solution was allowed to warm to room temperature (over 30 minutes) and was then allowed to stir at 20° C. for 30 minutes. The solvent was removed by rotary evaporation to give 27.75 g of the title compound as an orange waxy solid. $^1$H NMR (D$_2$O) δ 2.88 (t, 2H); 3.28 (t, 3H); 4.18 (s, 2H); 7.45 (dd, 1H); 8.22 (d, 1H); 8.55 (d, 1H).

Example 117
bis(2-Aminoethylthiomethylpyrid-3-yl)disulfide

Into a 1 L round bottom flask equipped with magnetic stirrer and thermometer was placed a 18 gauge stainless steel needle subsurface (to bubble in house air). To this apparatus was charged 3-mercapto-2-(aminoethylthiomethyl)pyridine trifluoroacetate (25 g, 0.125 mol, 1 eq) followed by methanol (300 mL) and the solution was cooled to 0° C. Concentrated ammonium hydroxide was added until a pH of 8 was reached. Solid ferric chloride (2.03 g, 0.0125 mol, 0.1 eq.) was added and air was vigorously bubbled in over a period of six hours during which time the black suspension of iron chloride became a light brown chunky solid. Mass spectral analysis confirmed the conversion to the di-sulfide. The methanolic solution was filtered over a small pad of celite to give a green colored filtrate. The methanol was removed in vacuo to give a brownish-green waxy solid. Removal of water by coevaporation with toluene (4×50 mL) gave 23.1 g of the title compound as a green waxy solid. $^1$H NMR (D$_2$O) δ 2.88 (t, 2H); 3.28 (t, 3H); 4.18 (s, 2H); 7.45 (dd, 1H); 8.22 (d, 1H); 8.55 (d, 1H). Mass spectrum: M+1 peak=399.

Example 118
bis(2-N-tert-Butoxycarbonylaminoethylthiomethylpyrid-3-yl)disulfide

Into a 1 L round bottom flask equipped with mechanical stirrer was charged XII (15 g, 0.038 mol, 1 eq.) followed by 150 mL of 5:1 water/dioxane. To this homogenous solution was charged finely powdered potassium carbonate (10.5 g, 0.076 mol. 2.0 eq.) and BOC-anhydride (9.2 g, 0.042 mol, 1.1 eq.). The solution was allowed to stir at 20° C. for three hours until reaction was determined to be complete by TLC analysis (1:1 hexane/EtOAc). The dioxane was removed by rotary evaporation at which time a white powder began to precipitate out of solution. The solution was allowed to cool to room temperature and the white solid was collected by vacuum filtration and the solid was washed twice with cold water to give 17.88 g of the title compound. $^1$H NMR (CDCl$_3$) δ 1.55 (s, 9H); 2.80 (t, 2H); 3.42 (t, 2H); 4.12 (s, 2H); 7.30 (dd, 1H); 8.02 (d, 1H); 8.48 (d, 1H).

Example 119
(7R)-7-[(Z)-2-(5-Amino-1,2,4-thiadiazol-3-yl)-2-(triphenylmethoxyimino)acetamido]-3-[2-(N-tert-butoxycarbonylaminoethylthiomethyl)pyrid-3-ylthio]-3-cephem-4-carboxylate, t-Butyl Ester Into a 250 mL round bottom flask equipped with magnetic stirrer and nitrogen purge was charged (7R)-7-[(Z)-2-(5-amino-1,2,4-thiadiazol-3-yl)-2-(triphenylmethoxyimino) acetamido]-3-chloro-3-cephem-4-carboxylate, t-butyl ester (5 g, 0.007 mol, 1 eq.) followed by DMF (80 mL) and water (0.8 mL) and to the resulting clear yellow solution was charged bis(2-N-tert-butoxycarbonylaminoethyl-thiomethylpyrid-3-yl)disulfide (3.29 g, 0.0035 mol., 0.5 eq) followed by triphenylphosphine (1.83 g, 0.007 mol, 1.0 eq). The yellow solution was allowed to stir at 20° C. for 3 hours. The reaction solution was poured into ice/water and extracted with 3:1 ethyl acetate-hexane (3×100 mL). The organics were combined and washed with water (2×100 mL) and then brine (2×50 mL). The organic layer was dried with sodium sulfate, filtered and the solvent removed in vacuo to give 6.55 g of the title compound as a light yellow foam. $^1$H NMR (CDCl$_3$) δ 1.42 (s, 18H); 1.61 (s, 9H); 2.87 (m, 3H); 2.95 (dd, 1H); 3.20 (d, 1H); 3.53 (d, 1H); 3.60 (t, 2H); 4.09

(s, 2H); 4.55 (bs, 1H); 5.20 (d, 1H); 5.80 (bs, 1H); 6.17 (q, 1H); 6.99 (bs, 1H); 7.2–7.8 (m, 17H); 8.60 (d, 1H).

Example 120

(7R)-7-[(Z)-2-(5-Amino-1,2,4-thiadiazol-3-yl)-2-(hydroxyimino)-3-[2-aminoethylthiomethyl)pyrid-3-ylthio]-3-cephem 4-Carboxylic Acid bis-TFA Salt Into a 250 mL round bottom flask equipped with magnetic stirrer and nitrogen purge was charged (7R)-7-[(Z)-2-(5-amino-1,2,4-thiadiazol-3-yl)-2-(triphenylmethoxyimimo)acetamido]-3-[2-(N-tert-butoxycarbonylaminoethyl-thiomethyl)pyrid-3-ylthio]-3-cephem-4-carboxylate, t-butyl ester (3.5 g, 0.003 mol, 1.0 eq.) followed by dichloromethane (20 mL). To the clear light yellow solution was charged triethylsilane (10.5 mL) followed by trifluroacetic acid (35 mL) dropwise over 2 minutes. The resulting yellow solution was allowed to stir at 20° C. for 8 hours until complete de-protection was confirmed by HPLC analysis. The acidic solution was poured into rapidly stirring 0° C. diethyl ether (300 mL) and the resulting white solid was collected by vacuum filtration and the filter cake was washed with additional diethyl ether (2×20 mL). The material was collected and was allowed to dry under high vacuum at 20° C. for one hour to give the title compound as an off-white solid. $^1$H NMR (CD$_3$OD) δ 2.80 (t, 2H); 3.02 (m, 2H); 3.61 (m, 3H); 4.17 (s, 2H); 4.28 (q, 1H); 5.38 (d, 1H); 6.05 (d, 1H); 7.51 (q, 1H); 8.05 (d, 1H); 8.57 (d, 1H).

Example 121

(7R)-7-[(Z)-2-(5-Amino-1,2,4-thiadiazol-3-yl)-2-(hydroxyimino)-3-[2-aminoethylthiomethyl)pyrid-3-ylthio]-3-cephem-4-carboxylate Zwitterion A 1 inch diameter glass column was packed with 30 grams of HP-20 resin and the acidic solution of (7R)-7-[(Z)-2-(5-amino-1,2,4-thiadiazol-3-yl)-2-(hydroxyimino)-3-[2-aminoethylthiomethyl)pyrid-3-ylthio]-3-cephem-4-carboxylic acid bis-TFA salt (1.2 g, 0.0013 mol) in water (20 mL) was charged on top of the resin and distilled water was eluted through until the pH of the eluent reached 5–6 (from <2). The solvent system was changed immediately to 4:1 water/acetonitrile and the zwitterionic compound was eluted in approximately 100 mL of eluent. The acetonitrile was removed in vacuo at <40° C. and the remaining water was lyophilized to give 0.79 g of the title compound as a white fluffy solid.

Example 122

Synthesis of Prodrugs bis[2-[2-(bis-N$_{\alpha,N\delta}$-t-Butoxycarbonyl)-N-(L)-ornithylaminoethylthiomethyl]-pyrid-3-yl]disulfide

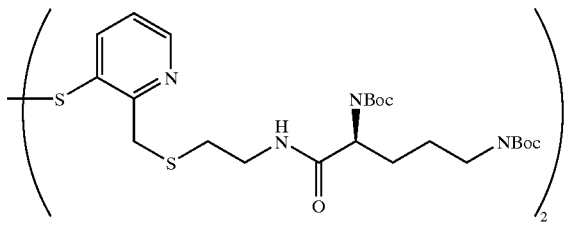

To DMF (7 mL) was added N-Boc-Orn-(Boc)-OH (0.504 g, 1.5 mmol), bis(2-(2-aminoethylthiomethyl)pyrid-3-yl) disulfide tetra HCl salt (0.389 g, 0.71 mmol), diisopropyl-ethylamine (0.641 g, 5.0 mmol, 0.86 mL), and PyBOP (0.780 g, 1.5 mmol), respectively. The reaction was stirred at room temperature for 2 hr, and then diluted with ethyl acetate (50 mL). The organics were washed with water (2×20 mL), brine (2×20 mL), separated dried over sodium sulfate, filtered and concentrated in vacuo. Purification of the title compound was achieved via SiO$_2$ column chromatography eluting with ethyl acetate affording 0.412 g (56%) of a white foamy solid.

Compound 17-A (7R)-7-[(Z)-2-(5-Amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic Acid, Methanesulfonic Acid Salt To a predried 25 mL round-bottomed flask was added DMF (1.5 mL), (7R)-7-[(Z)-2-(5-amino-1,2,4-thiadiazol-3-yl)-2-(triphenylmethoxyimino)acetamido]-3-methanesulfonyl-3-cephem-4-diphenylmethyl carboxylate (0.69, 0.8 mmol, bis[2-[2-(bis-N$_\alpha$,N$_\delta$-t-butoxycarbonyl)-N-(L)-ornithylaminoethylthiomethyl]pyrid-3-yl]disulfide (0.41 g, 0.4 mmol), water (0.036 mL), and triphenylphosphine (0.209 g, 0.8 mmol), respectively. The reaction mixture was stirred for 2 hr and then diluted with ethyl acetate (50 mL). The organics were washed with water (2×25 mL) and brine (2×25 mL). The organics were separated, dried over sodium sulfate, filtered, and concentrated in vacuo. Purification was achieved via SiO$_2$ column chromatography eluting with hexanes/ethyl acetate ramping from 1/1 to ethyl acetate (100%) affording 0.45 g (45%) of a white foamy solid. The white foamy solid was dissolved in methylene chloride/triethylsilane (2 mL; 1/1) and then cooled to 0° C., then trifluoroacetic acid (5 mL) was added via syringe. The reaction was stirred for 30 mm and then triturated with cold diethyl ether (30 mL) resulting in the precipitation of the desired TFA salt. The TFA salt was dissolved in water (5 mL) and placed atop a column of HP20 resin in water. The column was washed with water until an effluent pH of 6.5. The column was then eluted with acetonitrile/water (1/4; v/v). The UV active fractions were combined and tritiated with methanesulfonic acid to a pH=3.0. The organics were removed in vacuo and the product was obtained via lyophilization affording 0.095 g as a white amorphous solid. $^1$H NMR (D$_2$O) δ 2.00 (m, 2H), 2.18 (m, 2H), 3.00 (t, 2H, J=7), 3.26 (t, 2H, J=7), 3.51 (d, 1H, J=18), 3.66 (m, 2H), 4.00 (d, 1H, J=18), 4.24 (t, 1H, J=7), 4.43 (s, 2H), 5.59 (d, 1H, J=5), 6.13 (d, 1H, J=5), 8.05 (dd, 1H, J=7, 5), 8.51 (d, 1H, J=8), 8.77 (d, 1H, J=5).

The following compounds were synthesized in a similar manner as described above. The acylation of bis(2-(2-aminoethylthiomethyl)pyrid-3-yl)disulfide tetra HCl salt could also be performed utilizing activated esters (pentafluorophenol or N-hydroxysuccinimide) of the respective amino acids with similar results.

Compound 17-B

7R)-7-[(Z)-2-(5-Amino-1,2,4-thiadiazol-3-yl)-2-(hydroxyimino)acetamido]-3-{2-[2-N-(L)-prolylaminoethylthiomethyl]pyrid-3-ylthio)-3-cephem-4-carboxylate, Methane Sulfonic Acid Salt $^1$H NMR (D$_2$O) δ 2.12 (m, 3H), 2.52 (m, 1H), 2.87 (m, 2H), 2.92 (s, 3H), 3.58 (d, AB, 1H, J=17), 3.51 (m, 2H), 3.75 (d, AB, 1H, 17), 4.18 (m, 1H), 5.43 (d, 1H, J=5), 6.01 (d, 1H, J=5), 7.49 (dd, 1H, J=7, 5), 8.45 (d, 1H, J=5).

Compound 17-C (7R)-7-[(Z)-2-(5-N-(L)-Alanylamino-1,2,4-thiadiazol-3-yl)-2-(hydroxyimino)acetamido]-3-{2-[2-aminoethylthiomethyl]pyrid-3-ylthio}-3-cephem-4-carboxylate, Trifluoroacetic Acid Salt $^1$H NMR (CD$_3$OD) δ 1.74 (d, 3H, J=7), 2.94 (t, 2H, J=7), 3.38 (t, 2H, J=7), 3.41 (d, 1H, J=17), 3.70 (d, 1H, J=17), 4.18

(s, 2H), 4.41 (s, 2H), 5.33 (d, 1H, J=5), 6.04 (d, 1H, J=5), 7.45 (dd, 1H, J=7, 5), 8.01 (d, 1H, J=8), 8.53 (d, 1H, J=5).

Compound 17-D
(7R)-7-[(Z)-2-(5-Amino-1,2,4-thiadiazol-3-yl)-2-(hydroxyimino)acetamido]-3-{2-[2-N-(L,L)-alanylalanylaminoethylthiomethyl]pyrid-3-ylthio}-3-cephem-4-carboxylate, Trifluoroacetic Acid Salt $^1$H NMR (D$_2$O) δ 1.59 (d, 3H, J=8), 1.75 (d, 3H, J=8), 2.98 (t, 2H, J=7), 3.54 (d, 1H, J=17), 3.68 (m, 2H), 4.01 (d, 1H, J=17), 4.30 (q, 1H, J=8), 4.46 (s, 2H), 4.50 (q, 1H, J=8), 5.59 (d, 1H, J=5), 6.14 (d, 1H, J=5), 8.09 (dd, 1H, J=7, 5), 8.59 (d, 1H, J=8), 8.77 (d, 1H, J=5).

Compound 17-E
(7R)-7-[(Z)-2-(5-Amino-1,2,4-thiadiazol-3-yl)-2-(hydroxyimino)acetamido]-3-{2-[2-N-glycylaminoethyl-thiomethyl]pyrid-3-ylthio}-3-cephem-4-carboxylate, Methanesulfonic Acid Salt $^1$H NMR (D$_2$O) δ 2.88 (t, 2H, J=7), 2.92 (s, 3H), 3.41 (d, 1H, J=16), 3.54 (m, 2H), 3.88 (d, 1H, J=16), 3.91 (s, 2H), 4.30 (s, 2H), 5.48 (d, 1H, J=5), 5.94 (d, 1H, J=5), 7.89 (dd, 1H, J=8, 5), 8.34 (d, 1H, J=8), 8.59 (d, 1H, J=5).

Compound 17-F
(7R)-7-[(Z)-2-(5-Amino-1,2,4-thiadiazol-3-yl)-2-(hydroxyimino)acetamido]-3-{2-[2-N-(L)-aspartylamino-ethylthionethyl]pyrid-3-ylthio}-3-cephem-4-carboxylate, Trifluoroacetic Acid Salt $^1$H NMR (CD$_3$OD) δ 2.93 (m, 2H), 3.07 (dd, 1H, J=24, 9), 3.17 (dd, 1H, J=24, 5), 3.47 (d, 1H, J=18), 3.58 (m, 2H), 3.76 (d, 1H, J=18), 4.28 (s, 2H), 4.36 (m, 1H), 5.45 (d, 1H, J=5), 6.11 (d, 1H, J=5), 7.52 (dd, 1H, J=7,5), 8.22 (d, 1H, J=8), 8.67 (d, 1H, J=5).

Compound 17-G
(7R)-7-[(Z)-2-(5-Amino-1,2,4-thiadiazol-3-yl)-2-(hydroxyimino)acetamido]-3-{2-[2-N-(L)-alanylamino-ethylthiomethyl]pyrid-3-ylthio}-3-cephem-4-carboxylate, Methanesulfonic Acid Salt $^1$H NMR (CD$_3$OD) δ 1.69 (d, 3H, J=8), 2.89 (s, 3H); 2.91 (t, 2H, J=7), 3.43 (t, 2H, J=17), 3.63 (t, 2H, J=7), 3.73 (d, 1H, J=17), 4.09 (q, 1H, J=8), 4.25 (s, 2H), 5.44 (d, 1H, J=5), 6.09 (d, 1H, J=5), 7.54 (dd, 1H, J=7, 5), 8.02 (d, 1H, J=7), 8.62 (d, 1H, J=5).

Compound 17-H
(7R)-7-[(Z)-2-(5-Amino-1,2,4-thiadiazol-3-yl)-2-(hydroxyimino)acetamido]-3-{2-[2-N-(L)-(N$_α$-methyl)alanylaminoethylthiomethyl]pyrid-3-ylthio}-3-cephem-4-carboxylate, Methanesulfonic Acid Salt $^1$H NMR (CD$_3$OD) δ 1.70 (d, 3H, J=10), 2.87 (s, 3H), 2.88 (s, 3H), 2.95 (t, 2H, J=7), 3.53 (d, 1H, J=18), 3.67 (t, 2H, J=7), 3.83 (d, 1H, J=18), 4.15 (q, 1H, J=8), 4.34 (s, 2H), 5.48 (d, 1H, J=5), 6.12 (d, 1H, J=5), 7.58 (dd, 1H, J=7, 5), 8.36 (d, 1H, J=7), 8.73 (d, 1H, J=5).

Compound 17-I
(7R)-7-[(Z)-2-(5-Amino-1,2,4-thiadiazol-3-yl)-2-(hydroxyimino)acetamido]-3-{2-[2-N-(L)-histidylamino-ethylthiomethyl]pyrid-3-ylthio}-3-cephem-4-carboxylate, Methanesulfonic Acid Salt $^1$H NMR (CD$_3$OD) δ 2.88 (t, 2H, J=7), 2.90 (s, 3H), 3.50 (d, 1H, J=17), 3.57 (t, 2H, J=6), 3.76 (d, 1H, J=17), 4.26 (s, 2H). 4.38 (t, 2H, J=7), 5.46 (d, 1H, J=5), 6.07 (d, 1H, J=5), 7.65 (m, 1H), 8.21 (d, 1H, J=6), 8.66 (m, 1H), 9.08 (s, 1H).

Compound 17-J
(7R)-7-[(Z)-2-(5-Amino-1,2,4-thiadiazol-3-yl)-2-(hydroxyimino)acetamido]-3-{2-[2-N-(L)-valylamino-ethylthiomethyl]pyrid-3-ylthio}-3-cephem-4-carboxylate, Methanesulfonic Acid Salt $^1$H NMR (D$_2$O) δ 1.12 (d, 3H, J=6), 1.13 (d, 3H, J=6), 2.30 (septet, 1H, J=6), 2.91 (t, 2H, J=6), 2.92 (s, 3H), 3.43 (d, AB, J=18), 3.54 (m, 1H), 3.67 (m, 1H), 3.88 (d, 1H, J=6), 3.91 (d, AB, J=18), 4.33 (s, 2H), 5.50 (d, 1H, J=5), 6.05 (d, 1H, J=5), 7.93 (dd, 1H, J=7, 5), 8.40 (d, 1H, J=7), 8.64 (d, 1H, J=5).

Compound 17-K
(7R)-7-[(Z)-2-(5-Amino-1,2,4-thiadiazol-3-yl)-2-(hydroxyimino)acetamido]-3-{2-[2-N-(L)-asparagylamino-ethylthiomethyl]pyrid-3-ylthio}-3-cephem-4-carboxylate, Trifluoroacetic Acid Salt $^1$H NMR (D$_2$O) δ 2.74–2.79 (m, 4H), 2.93 (t, 2H, J=6), 3.27 (dd, 1H, J=18, 13), 3.32–3.50 (m, 3H), 3.75 (d, 1H, J=18), 4.17 (s, 2H), 4.29 (t, 1H, J=14), 5.35 (d, 2H, J=5), 5.90 (d, 1H, J=5), 7.75 (dd, 1H, J=8, 5), 8.22 (d, 1H, J=8), 8.45 (d, 1H, J=5).

Compound 17-L
(7R)-7-[(Z)-2-(5-Amino-1,2,4-thiadiazol-3-yl)-2-(hydroxyimino)acetamido]-3-{2-[2-N-(L)-lysylamino-ethylthiomethyl]pyrid-3-ylthio}-3-cephem-4-carboxylate, Methanesulfonic Acid Salt $^1$H NMR (CD$_3$OD) δ 1.73 (m, 1H), 1.92 (m, 1H), 2.09 (m, 1H), 2.91 (s, 3H), 2.98 (m, 3H), 3.18 (t, H, J=6), 3.49 (d, AB, 1H, J=17), 3.65 (m, 2H), 3.75 (d, AB, 1H, J=17), 4.09 (t, 1H, J=6), 4.31 (s, 2H), 5.48 (d, 1H, J=5), 6.09 (d, 1H, J=5), 7.61 (dd, 1H, J=7, 5), 8.19 (d, 1H, J=7), 8.69 (d, 1H, J=5).

Compound 17-M
(7R)-7-[(Z)-2-(5-Amino-1,2,4-thiadiazol-3-yl)-2-(hydroxyimino)acetamido]-3-{2-[2-N-(L)-serylamino-ethylthiomethyl]pyrid-3-ylthio}-3-cephem-4-carboxylate, Methanesulfonic Acid Salt $^1$H NMR (D$_2$O) δ 2.85 (m, 3H), 3.35 (d, 1H, J=17), 3.45 (t, 2H, J=6), 3.84 (d, 1H, J=17), 3.99 (ddd, 2H, J=24, 12, 5), 4.17 (t, 2H, J=5), 4.26 (s, 2H), 5.42 (d, 1H, J=5), 5.97 (d, 1H, J=5), 7.80 (dd, 1H, J=8, 5), 8.24 (d, 1H, J=5), 8.49 (d, 1H, J=5).

Compound 17-N
(7R)-7-[(Z)-2-(5-Amino-1,2,4-thiadiazol-3-yl)-2-(hydroxyimino)acetamido]-3-{2-[2-N-(L)-glutaminyl-aminoethylthiomethyl]pyrid-3-ylthio}-3-cephem-4-carboxylate, Methanesulfonic Acid Salt $^1$H NMR (D$_2$O) δ 2.19 (q, 2H, J=7), 2.50 (t, 2H, J=8), 2.85 (m, 5H), 3.34 (d, 1H, J=18), 3.51 (m, 2H), 3.84 (d, 1H, J=18), 4.08 (t, 1H, J=7), 4.28 (s, 2H), 5.43 (d, 1H, J=5), 5.97 (d, 1H, J=5), 7.90 (dd, 1H, J=8), 8.37 (d, 1H, J=8), 8.58 (d, 1H, J=8).

bis-{2-[2-(5-Methyl-1,3-dioxolan-4-en-2-on-4-yl)methoxycarbonyl)aminoethylthiomethyl]pyrid-3-yl}disulfide

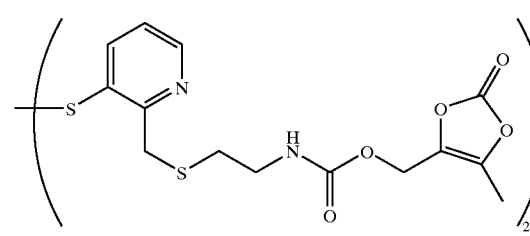

To a predried 25 mL round-bottomed flask charged with DMF (15 mL) was added bis(2-(2-aminoethylthiomethyl)pyrid-3-yl)disulfide tetra HCl salt (1.0 g, 3.39 mmol) and (5-methyl-2-oxo-1,3-dioxolan-4-enyl)methyl p-nitrophenyl carbonate (0.922 g, 1.69 mmol). With stirring, triethylamine (3.6 mL, 21 mmol) was added dropwise via syringe. Following complete consumption of the starting materials, as monitored by thin layer chromatography (ethyl acetate), the reaction was diluted with 20 mL of water, and extracted with ethyl acetate (2×20 mL). The organic layer was separated, washed with 1 N HCl (1×10 mL), 2% sodium bicarbonate (1×10 mL), water (1×10 mL), and brine (1×10 mL), respectively. The organics were separated, dried over sodium sulfate, filtered, and concentrated in vacuo. Purification of the title compound was achieved via $SiO_2$ column chromatography eluting with ethyl acetate (100%) affording 0.252 g (10%) as a yellow solid.

Compound 17-O
(7R)-7-[(Z)-2-(5-Amino-1,2,4-thiadiazol-3-yl)-2-(hydroxyimino)acetamido]-3-{2-[2-(5-methyl-1,3-dioxolan-4-en-2-on-4-yl)methoxycarbonyl)aminoethylthiomethyl]pyrid-3-ylthio}-3-cephem-4-carboxylate, Sodium Salt To a predried 25 mL round-bottomed flask charged with DMF (3 mL) were added (7R)-7-[(Z)-2-(5-amino-1,2,4-thiadiazol-3-yl)-2-(triphenylmethoxyimino)acetamido]-3-methanesulfonyl-3-cephem-4-diphenylmethyl carboxylate (0.200 g, 0.23 mmol), bis-{2-[2-(5-methyl-1,3-dioxolan-4-en-2-on-4-yl)methoxycarbonyl)aminoethylthiomethyl]pyrid-3-yl}disulfide (0.080 g, 0.12 mmol), water (0.010 mL), and triphenylphosphine (0.060 g, 0.24 mmol), respectively. Upon stirring for 2.5 hr, the reaction was diluted with ethyl acetate (10 mL) and the organics were washed with water (1×10 mL) and brine (1×10 mL). The organics were separated and dried over anhydrous sodium sulfate, filtered and concentrated in vacuo. Purification was achieved via $SiO_2$ column chromatography eluting with ethyl acetate (100%) affording 0.212 g (82%) as a yellow foamy solid. The yellow solid was dissolved in methylene chloride/triethylsilane (2 mL; 1/1, v/v) and cooled to 0° C. To the reaction flask was added dichloroacetic acid (4.2 mL) and the mixture was stirred for 1 hr. The reaction was triturated with diisopropyl ether (15 mL) resulting in the precipitation of the desired product. The solids were collected, dissolved in water (5 mL), and tritiated with 0.5 M sodium bicarbonate until the solution became homogenous. The solution was loaded atop a column of HP20 resin packed with water and the column was washed with water until the pH of the effluent became 7. The column was then eluted with acetonitrile/water (7/1). The UV active fractions were combined, reduced in vacuo to remove the acetonitrile, and the title compound was isolated via lyophilization affording 0.070 g (50%) of the title compound as a white amorphous solid. $^1$H NMR ($D_2O$) δ 2.21 (s, 3H), 2.90 (bt, 2H, J=7), 3.47 (m, 2H), 3.80 (d, 1H, J=18), 4.20 (s, 2H), 4.95 (s, 2H), 5.56 (d, 1H, J=5), 6.02 (d, 1H, J=5), 7.53 (dd, 1H, J=7, 5), 8.03 (d, 1H, J=7), 8.51 (d, 1H, J=5).

The following compound was converted to its respective sodium salt in a similar manner as described above.

Compound 17-P
(7R)-7-[(Z)-2-(5-Amino-1,2,4-thiadiazol-3-yl)-2-(hydroxyimino)acetamido]-3-}2-(2-N-(L)-pyroglutaminylaminoethylthiomethyl]pyrid-3-ylthio}-3-cephem-4-carboxylate, Sodium Salt $^1$H NMR ($CD_3OD$) δ 2.50 (m, 4H), 2.82 (t, 2H, J=7), 3.30 (s, 3H), 3.35 (d, 1H, J=17), 3.52 (m, 2H), 3.71 (d, 1H, J=17), 4.17 (s, 2H), 4.35 (m, 1H), 5.38 (d, 1H, J=5), 7.41 (dd, 1H, J=7, 5), 8.42 (m, 1H).

Example 123
2-Chloromethyl-3-triphenylmethylthiopyridine Hydrochloride

A thick suspension of 2-hydroxymethyl-3-triphenylmethylthiopyridine (90.3 g, 235 mmol) in N,N-dimethylformamide (270 mL) in a flask equipped with efficient mechanical stirring was chilled to 2° C. Thionyl chloride (25.8 mL, 354 mmol) was added in 5 mL portions over the period of 1 h while maintaining a temperature below 10° C. After completing the addition the reaction mixture was allowed to reach room temperature and was stirred for 30 min. The precipitate was filtered, washed with ethyl acetate (500 mL) and dried to give 86.7 g (84%) 2-chloromethyl-3-triphenylmethylthiopyridine hydrochloride as colorless crystals.

Example 124
2-(2-Aminoethylthiomethyl)-3-triphenylmethylthiopyridine

To a stirred solution of sodium methoxide (0.787 mol) in methanol (425 mL) were added at room temperature under nitrogen 2-chloromethyl-3-triphenylmethylthiopyridine hydrochloride (86 g, 0.196 mol) and cysteamine hydrochloride (33.0 g, 0.290 mol). After 2.5 h, the reaction mixture was partitioned between ethyl acetate (500 mL), water (500 mL) and brine (250 mL). The organic layer was separated and the aqueous layer was extracted with ethyl acetate (250 mL). The combined organic extracts were washed with brine (3×500 mL) and dried over anhydrous sodium sulfate. Following filtration, evaporation of the filtrate under reduced pressure produced 2-(2-aminoethylthiomethyl)-3-triphenylmethylthiopyridine as a yellowish oil (92.7 g, after correcting for residual solvent by NMR, 87.0 g, quantitative yield).

Example 125
2-(2-Aminoethylthiomethyl)3-triphenylmethylthiopyridine

Into a 20 mL flask was charged 2-(2-N-tert-butoxycarbonylaminoethylthiomethyl)3-triphenylmethylthiopyridine (0.20 g, 0.37 mmol, 1.0 eq.) and 4.5 M HCl (dry) in methanol (2.0 mL, 9.0 mmol, 24 eq). The solution was placed in the refrigerator (4° C.) for 2 h. At the end of two hours, the reaction solution was pipetted into 20 mL water with ice chips and a suspension immediately formed. The bis-HCl salt was next neutralized with saturated sodium bicarbonate (1 mL) and extracted with ethyl acetate (15 mL). The phases were separated and the aqueous phase was extracted with additional ethyl acetate (10 mL). The combined organic extracts were dried with sodium sulfate, filtered, and the solvent removed in vacuo to give a white powder (80 mg, 50%) containing predominantly 3-triphenylmethylthio-2-(2-aminoethylthiomethyl)pyridine (HPLC, NMR). $^1$H NMR (4:1 $CDCl_3$:$CD_3OD$) δ 2.65 ppm (t, 2H), 3.00 (t, 2H), 3.52 (s, 2H), 6.82 (d, 1H), 7.00–7.40 (m, 15H), 8.20 (d, 1H).

Example 126
2-[2-L-(N-tert-Butoxycarbonyl-4-tert-butylaspartyl)aminoethylthiomethyl]-3-triphenylmethylthiopyridine To a stirred solution of 2-(2-aminoethylthiomethyl)3-triphenylmethylthiopyridine (57.1 g, 129 mmol) in ethyl acetate (285 mL) was added a solution of N-(tert-butoxycarbonyl)-4-tert-butyl-L-aspartic acid pentafluorophenol ester (52.8 g, 116 mmol) and the mixture was stirred at room temperature for 4 h. The reaction mixture was washed with an aqueous solution of sodium carbonate (0.9 M, 1 L). The organic layer was separated, washed twice with brine (500 mL) and dried over anhydrous sodium sulfate. Hexane (400 mL) was added with stirring until a slight cloudiness persisted, and then ethyl acetate was added to give a clear solution. The resulting solution was filtered through a plug of silica gel (300 mL; 2 inch layer) followed by washing with ethyl acetate-hexane solution (1 L). The combined filtrates were concentrated to an oily residue and purified by chromatography over silica gel using a step-gradient elution with ethyl acetate-hexane solution (1:2, then 1:1 and finally, 2:1). The filtrates were evaporated to an oily residue of 2-[2-L-(N-tert-butoxycarbonyl-4-tertbutylaspartyl)aminoethylthiomethyl]-3-triphenylmethyl-thiopyridine (65 g, 75%) which was used immediately in the next step.

Example 127
2-(2-L-Aspartylaminoethylthiomethyl)-3-mercaptopyridine Dihydrochloride To a stirred solution of 2-[2-L-(N-tert-butoxycarbonyl-4-tert-butylaspartyl)aminoethylthiomethyl]-3-triphenyl-methylthiopyridine (65 g, 87 mmol) in dichloromethane (130 mL) under nitrogen was added triethylsilane (130 mL, 810 mmol) and the solution was cooled to 0° C. Trifluoroacetic acid (650 mL) was added and the mixture was allowed to return to room temperature and stirred for 3.5 h. The mixture was concentrated under reduced pressure to a syrupy residue (~30° C. bath) which was then dissolved in ethyl acetate (300 mL). To this solution was added with stirring a solution of dry HCl in ethyl acetate (150 mL, 1.75 M, 262 mmol) followed by addition of more ethyl acetate (300 mL) to facilitate stirring. After stirring for an additional 30 min solids were collected by filtration under nitrogen, washed with ethyl acetate and dried in vacuo to yield 2-(2-L-aspartylaminoethylthiomethyl)-3-mercaptopyridine dihydrochloride as a white powder (33.7 g, 99%).

Example 128
bis(2-[2-L-(N-tert-Butoxycarbonyl-4-tert-butylaspartyl)aminoethylthiomethyl]pyrid-3-yl)disulfide A flask was charged with bis(2-aminoethylthiomethyl)pyrid-3-yl)disulfide (80 mg, 0.20 mmol, 1.0 eq.), aqueous 1M sodium bicarbonate (2.0 mL, 2.0 mmol, 10 eq.), and water (5 mL). To this was added N-(tert-butoxycarbonyl)-4-tert-butyl-L-aspartic acid pentafluorophenol ester (0.18 g, 0.40 mmol, 2.0 eq.) dissolved in ethyl acetate (2.5 mL), followed by sodium chloride (50 mg, 10% solution). The biphasic mixture was stirred vigorously at room temperature and after 24 h. The layers were separated and the aqueous phase was washed with additional ethyl acetate (2.5 mL). The organic extracts were combined and washed with brine (2×5 mL), dried with sodium sulfate, filtered and the solvent was removed in vacuo. The resulting oily product was purified by radial chromatography first with 1:5 (v/v) hexane-ethyl acetate to remove less polar materials, followed by neat ethyl acetate to afford pure bis(2-[2-L-(N-tert-butoxycarbonyl-4-tert-butylaspartyl)aminoethylthio-methyl]pyrid-3-yl)disulfide (100 mg, 54% yield). $^1$H NMR (CDCl$_3$) δ 1.50 ppm (s, 18H), 1.55 (s, 18H), 2.72 (m, 6H), 2.92 (d, 2H), 2.98 (q, 2H), 3.55 (q, 4H), 4.55 (d, 2H), 5.80 (d, 2H), 7.35 (m, 4H), 8.10 (d, 2H), 8.50 (d, 2H).

Example 129
2-[2-L-(N-tert-Butoxycarbonyl-4-tert-butylaspartyl)aminoethylthiomethyl]-3-mercaptopyridine To a stirred solution of bis(2-[2-L-(N-tert-butoxycarbonyl-4-tert-butylaspartyl)aminoethylthiomethyl]pyrid-3-yl)disulfide (19.3 g, 41.0 mmol) in N,N-dimethylformamide (170 mL) was added water (1.7 mL, 94 mmol) followed by triphenylphosphine (11.8 g, 45 mmol). After 4 h at room temperature, additional triphenylphosphine (5.38 g, 20.5 mmol) was added and the reaction was continued at room temperature overnight. The reaction mixture was partitioned between water (500 mL) and 3:1 (v/v) ethyl acetate-hexane. The organic extract was washed with brine (3×250 mL), dried over sodium sulfate and concentrated under reduced pressure to produce 2-[2-L-(N-tert-butoxycarbonyl-4-tert-butylaspartyl)aminoethylthiomethyl]-3-mercaptopyridine, which was used immediately in the next reaction.

Example 130
2-[2-L-(N-tert-Butoxycarbonyl-4-tert-butylaspartyl)aminoethylthiomethyl]-3-mercaptopyridine A flask equipped with a mechanical stirrer was charged with 2-(2-aminoethylthiomethyl)-3-mercaptopyridine dihydrochloride (2.1 g, 7.7 mmol, 1.07 eq.), N-(tert-butoxycarbonyl)-4-tert-butyl-L-aspartic acid pentafluorophenol ester (3.3 g, 7.2 mmol, 1.0 eq.), triethylamine (2.1 mL, 15 mmol, 2.1 eq.) and N,N-dimethylformamide (55 mL). The solution was allowed to stir at 20° C. for 3 h. The solution was diluted to 200 mL with water and washed with 3:1 (v/v) ethyl acetate-hexanes (2×50 mL). The combined organic extracts were washed with brine (3×100 mL), dried with sodium sulfate, filtered and the solvent removed in vacuo to give 2-[2-L-(N-tert-butoxycarbonyl-4-tert-butylaspartyl)aminoethylthiomethyl]-3-mercaptopyridine which was used in the next step without further purification.

Example 131
2-(2-L-Aspartylaminoethylthiomethyl)-3-mercaptopyridine Dihydrochloride A flask equipped with a magnetic stirrer was charged with 2-[2-L-(N-tert-butoxycarboryl-4-tert-butylaspartyl)aminoethylthiomethyl]-3-mercaptopyridine (0.24 g, 0.51 mmol, 1.0 eq.), followed by CH$_2$Cl$_2$ (1.2 mL) and triethyl-silane (1.2 mL). Dropwise, trifluoroacetic acid (4.8 mL) was added to the solution, which was allowed to stir at 20° C. for 3 h. The solution was concentrated in vacuo, and the residue was dissolved in ethyl acetate (25 mL). Into this solution was bubbled anhydrous HCl. The white solid, which precipitated almost immediately, was carefully filtered and washed with ethyl acetate, while avoiding exposure to moisture, and dried in vacuo to yield 0.18 g (90%) 2-(2-L-aspartylaminoethylthiomethyl)-3-mercaptopyridine dihydrochloride as a white powder.

Example 132
Sodium (Z)-2-(5-Amino-1,2,4-thiadiazol-3-yl)-2-(triphenylmethyl)oxyiminoacetate A suspension of methyl (Z)-2-(5-ethoxycarbonylamino-1,2,4-thiadiazol-3-yl)-2-(triphenylmethyl)oxyiminoacetate (7.3 g, 14.1 mmol) was heated at 80° C. under reflux in 55 mL of 2:1 (v/v) aqueous NaOH (2.5 M) and ethanol. After 24 h the reaction mixture was allowed to cool to room temperature and the precipitate was collected by filtration, washed with water (washes were not combined with the original filtrate) and dried in vacuo to produce crystalline sodium (Z)-2-(5-amino-1,2,4-thiadiazol-3-yl)-2-(triphenylmethyl)oxyiminoacetate (3.08 g, 48% yield). The filtrate was resubjected to an additional 24 h of heating at 80° C. and the above described workup procedure was repeated to produce a second crop of sodium (Z)-2-(5-amino-1,2,4-thiadiazol-3-yl)-2-(triphenylmethyl)oxyiminoacetate (1.43 g, 22% yield). A third crop of sodium (Z)-2-(5-amino-1,2,4-thiadiazol-3-yl)-2-(triphenylmethyl)oxyiminoacetate (0.49 g, 8% yield) was obtained after subjecting the filtrate to another 24 h period of heating at 80° C.

Example 133
(7R)-7-Amino-3-chloroceph-3-em-4-carboxylate, tert-Butyl Ester

To a suspension of 7-amino-3-chloroceph-3-em-4-carboxylate (23.7 g, 101.2 mmol) in t-butyl acetate (510 mL), under nitrogen, was added BF$_3$ etherate (80 mL) and the mixture was stirred vigorously at room temperature until complete dissolution was observed. After 2.5 h the reaction mixture was poured into stirred ice water (1 L) and the organic layer was discarded. The aqueous layer was washed with 1:1 (v/v) ethyl acetate-hexane (200 mL) and separated. To this aqueous solution with ice cooling and stirring was added ethyl acetate (500 mL) followed by portionwise addition of sodium carbonate (216 g) until a pH of 8–8.5 was reached. The organic layer was separated and the aqueous layer was extracted with ethyl acetate (100 mL). The combined organic extracts were dried over anhydrous sodium sulfate and concentrated under reduced pressure to give an oily residue (28 g) which solidified after removing the flask from the bath. To this residue was added toluene (100 mL; partial dissolution) followed by hexane (100 mL). After 10 min of additional stirring crystalline (7R)-7-amino-3-chloroceph-3-em-4-carboxylate, tert-butyl ester was filtered, washed with hexane and dried under reduced pressure (15.4 g; 52%).

Example 134
(7R)-7-[(Z)-2-(5-Amino-1,2,4-thiadiazol-3-yl)-2-(triphenylmethyloxyimino)acetamido-3-chloroceph-3-em-4-carboxylate, tert-Butyl Ester To a stirred suspension of sodium (Z)-2-(5-amino-1,2,4-thiadiazol-3-yl)-2-triphenylmethyloxyiminoacetate (14.38 g, 31.7 mmol) in dry THF (170 g) was added diphenyl chlorophosphate (9.9 mL, 47.8 mmol, 1.5 eq.). After a few minutes of stirring most of the starting material dissolved. Stirring was continued for 1 h at ambient temperature and tert-butyl (7R)-7-amino-3-chloroceph-3-em-4-carboxylate (9.19 g, 31.7 mmol, 1.0 eq.) was added followed by addition of 2,6-lutidine (3.7 mL, 31.7 mmol, 1.0 eq.). After 3 h at room temperature the reaction mixture was partitioned between ethyl acetate (200 mL) and 0.5 M HCl (100 mL). Following phase separation, the organic layer was washed again with 0.5 M HCl (100 mL), then with 0.5 M NaHCO$_3$ solution (2×100 mL). The organic phase was dried over anhydrous sodium sulfate and concentrated to a volume of about 60 mL. To this solution was added 1:2 ethyl acetate-hexane (80 mL) and after seeding, the product, (7R)-7-[(Z)-2-(5-amino-1,2,4-thiadiazol-3-yl)-2-(triphenylmethyloxyimino)acetamido-3-chloroceph-3-em-4-carboxylate, tert-butyl ester was allowed to crystallize overnight. Solids were collected by filtration and dried in vacuum to afford 14.1 g (63%) of product.

Example 135
(7R)-7-[(Z)-2-(5-Amino-1,2,4-thiadiazol-3-yl)-2-(triphenylmethyloxyimino)acetamido-3-[2-(2-L-(N-tert-butoxycarbonyl-4-tert-butylaspartyl)aminoethylthiomethyl)pyrid-3-ylthio]ceph-3-em-4-carboxylate, tert-Butyl Ester To a nitrogen purged flask equipped with a magnetic stirrer was added at room temperature N,N-dimethylformamide (335 mL, deoxygenated by prolonged purging with a stream of dry nitrogen), (7R)-7-[(Z)-2-(5-amino-1,2,4-thiadiazol-3-yl)-2-(triphenylmethyloxyimino) acetamido-3-chloroceph-3-em-4-carboxylate, tert-butyl ester (16.0 g, 22.8 mmol), bis(2-[2-L-(N-tert-butoxycarbonyl-4-tert-butylaspartyl)aminoethylthiomethyl]pyrid-3-yl)disulfide (10.8 g, 11.4 mmol), water (3.4 mL) and triphenylphosphine (6.6 g, 25.1 mmol). After overnight reaction the reaction mixture was partitioned between etyl acetate/hexane 3:1 (v/v) mixture (900 mL) and water (1.5 L). Organic layer was thoroughly washed with water and concentrated under reduced pressure to produce oliy residue. Chromatography on silica gel column (gradient elution with hexane-ethyl acetate) provided (7R)-7-[(Z)-2-(5-amino-1,2,4-thiadiazol-3-yl)-2-(triphenylmethyloxyimino)acetamido-3-[2-(2-L-(N-tert-butoxycarbonyl-4-tert-butylaspartyl)aminoethylthiomethyl)pyrid-3-ylthio]ceph-3-em-4-carboxylate, tert-butyl ester (18.4 g, 84%) contaminated with small amount of triphenylphosphine oxide.

Example 136
(7R)-7-[(Z)-2-(5-Amino-1,2,4-thiadiazol-3-yl)-2-(triphenylmethyloxyimino)acetamido-3-(2-(2-L-aspartylaminoethylthiomethyl)pyrid-3-ylthio)ceph-3-em-4-carboxylate, tert-Butyl Ester To a nitrogen purged flask equipped with a magnetic stirrer was added N,N-dimethylformamide (45 mL, deoxygenated by prolonged purging with a stream of dry nitrogen), (7R)-7-[(Z)-2-(5-amino-1,2,4-thiadiazol-3-yl)-2-(triphenylmethyloxyimino)acetamido-3-chloroceph-3-em-4-carboxylate, tert-butyl ester (10.5 g, 14.9 mmol) and 2-(2-L-aspartylaminoethylthiomethyl)-3-mercaptopyridine dihydrochloride (7.5 g, 19.3 mmol). The mixture was stirred until complete dissolution of starting materials and was then cooled to 0° C. (ice water bath). Triethanolamine (5.8 g, 38.9 mmol) solution in N,N-dimethylformamide (6 mL) was added in one portion. After 4.5 h additional amounts of 2-(2-L-aspartylaminoethylthiomethyl)-3-mercaptopyridine dihydrochloride (0.7 g, 1.8 mmol) in in N,N-dimethylformamide (5 mL) and triethanolamine (0.54 g, 3.6 mmol) in N,N-dimethylformamide (1 mL) were added. After an additional 1 h, the reaction mixture was poured into a flask containing a vigorously stirred mixture of water (100 mL) and crushed ice (200 mL). Stirring was continued until all of the ice melted. The precipitated crude product was filtered, washed thoroughly with water and dried overnight in vacuo. The crude product was washed three times with ethyl acetate (3×200 mL) with repeated thorough trituration with the spatula. The resulting yellow precipitate was dried in vacuo to produce (7R)-7-[(Z)-2-(5-amino-1,2,4-thiadiazol-3-yl)-2-(triphenylmethyloxyimino)acetamido-3-(2-(2-L-aspartylaminoethylthiomethyl)pyrid-3-ylthio)ceph-3-em-4-carboxylate, tert-butyl ester (13.2 g, 90% yield).

Example 137
(7R)-7-[(Z)-2-(5-Amino-1,2,4-thiadiazol-3-yl)-2-(triphenylmethyloxyimino)acetamido-3-(2-(2-L-aspartylaminoethylthiomethyl)pyrid-3-ylthio)ceph-3-em-4-carboxylate, tert-Butyl Ester To a nitrogen purged flask equipped with a magnetic stirrer was added N,N-dimethylformamide (2.4 mL), deoxygenated by prolonged purging with a stream of dry nitrogen 2-(2-L-aspartylaminoethylthiomethyl)-3-mercaptopyridine dihydrochloride (0.22 g, 0.57 mmol) was added. The mixture was stirred until complete dissolution of starting materials and was then cooled to 0° C. (ice water bath). A solution of sodium hydroxide in water (0.38 mL, 3.0 M, 1.14 mmol) was added followed by addition of (7R)-7-[(Z)-2-(5-amino-1,2,4-thiadiazol-3-yl)-2-(triphenylmethyloxyimino) acetamido-3-chloroceph-3-em-4-carboxylate, tert-butyl ester (0.40 g, 0.57 mmol). After 4 h the reaction mixture was poured into a flask containing a vigorously stirred ice water. The precipitated crude product was filtered, washed thoroughly with water and dried overnight in vacuum. The crude product was washed three times with ethyl acetate with repeated thorough trituration with the spatula. The resulting yellow precipitate was dried in vacuo to produce (7R)-7-[(Z)-2-(5-amino-1,2,4-thiadiazol-3-yl)-2-(triphenylmethyloxyimino)acetamido-3-(2-(2-L-aspartylaminoethylthiomethyl)pyrid-3-ylthio)ceph-3-em-4-carboxylate, tert-butyl ester (0.46 g, 90% yield).

Example 138

(7R)-7-[(Z)-2-(5-Amino-1,2,4-thiadiazol-3-yl)-2-(hydroxyimino)acetamido-3-[2-(2-L-aspartyl)aminoethylthiomethyl)pyrid-3-ylthio]ceph-3-em-4-carboxylate, bis-Trifluoroacetic Acid Salt

Into a flask equipped with a magnetic stirring bar and nitrogen purge was charged (7R)-7-[(Z)-2-(5-amino-1,2,4-thiadiazol-3-yl)-2-(triphenylmethyloxyimino)acetamido-3-[2-(2-L-(N-tert-butoxycarbonyl-4-tert-butylaspartyl)aminoethylthiomethyl)pyrid-3-ylthio]ceph-3-em-4-carboxylate, tert-butyl ester (3.5 g, 3 mmol) followed by dichloromethane (20 mL). To the clear light yellow solution was charged triethylsilane (10.5 mL) followed by trifluoroacetic acid (35 mL) dropwise over 2 min. The resulting yellow solution was allowed to stir at 20° C. for 8 h. The acidic solution was poured into rapidly stirring diethyl ether (300 mL) cooled to 0° C. and the resulting white solid was collected by filtration. The filter cake was washed with fresh diethyl ether (2×20 mL) and dried in vacuum at to yield 2.41 g (86%) (7R)-7-[(Z)-2-(5-amino-1,2,4-thiadiazol-3-yl)-2-(hydroxyimino)acetamido-3-[2-(2-L-aspartyl)aminoethylthiomethyl)pyrid-3-ylthio]ceph-3-em-4-carboxylate, bis-trifluoroacetic acid salt. NMR: example 120 This salt was processed to the zwitterion form as described previously in example 121.

Example 139

(7R)-7-[(Z)-2-(5-Amino-1,2,4-thiadiazol-3-yl)-2-(hydroxyimino)acetamido-3-[2-(2-L-aspartyl)aminoethylthiomethyl)pyrid-3-ylthio]ceph-3-em-4-carboxylate, bis-Trifluoroacetic Acid Salt

Into a flask equipped with a magnetic stirring bar and nitrogen purge was charged tert-butyl (7R)-7-[(Z)-2-(5-amino-1,2,4-thiadiazol-3-yl)-2-(triphenylmethyloxyimino)acetamido-3-[2-(2-L-aspartyl)aminoethylthiomethyl)pyrid-3-ylthio]ceph-3-em-4-carboxylate (12.2 g, 12.0 mmol), dichloromethane (61 mL) and triethylsilane (61 mL, 380 mmol). The mixture was cooled to 0° C. followed by dropwise addition of trifluoroacetic acid (244 mL, 3.20 mol). Following the addition, the cooling bath was removed, and the reaction was allowed to warm to room temperature. After 3 h the mixture was concentrated under reduced pressure to an oily residue. Diisopropyl ether (400 mL) was added with stirring, and the precipitate was stored overnight at 4° C. The granular precipitate was filtered, thoroughly washed with diisopropyl ether, and dried in vacuum to yield 12.8 g (7R)-7-[(Z)-2-(5-amino-1,2,4-thiadiazol-3-yl)-2-(hydroxyimino)acetamido-3-[2-(2-L-aspartyl)aminoethylthiomethyl)pyrid-3-ylthio]ceph-3-em-4-carboxylate, bis-trifluoroacetic acid salt. NMR: example 120 This salt was processed to the zwitterion form as described previously in example 121.

Example 140

Evaluation of Prodrugs of Compound 17

An aspect of the invention is the formation of prodrugs of Compound 17. These prodrugs display improved solubility, allowing their administration to patients at higher concentrations. Several prodrugs of Compound 17 have been synthesized and their solubility has been determined at near physiological pH. The release of Compound 17 is determined by analyzing the in vitro rate of hydrolysis of the prodrug by serum enzymes of three species (rat, monkey, and human).

A. Solubility Protocol:

A small amount of a solid salt (5–8 mg) is weighed into screw cap vial. Water is added to dissolve the solid at a high concentration (50–75 mg/mL). To this solution is added small amounts (1–5 $\mu$L increments) of 0.1 N aqueous sodium hydroxide until a faint precipitate remains after mixing. The suspension is left at room temperature for 15 minutes with periodic vortexing. An aliquot of the suspension is then transferred to an Eppendorf tube and centrifuged at 14000 rpm for 1.5 minutes. A portion of the supernatant is diluted with water, filtered and quantified by HPLC against a standard calibration curve. The pH of the supernatant is measured using a fine needle probe. For each subsequent determination, using a new sample, more 0.1 N sodium hydroxide is added to increase the pH just slightly, and the rest of the procedure is repeated. Five to seven determinations are used to prepare the pH vs. concentration curve.

When starting with zwitterion, the solid zwitterion is suspended in water. Either 0.1 N sodium hydroxide or 0.1 N hydrochloric acid is added to begin to dissolve the solid. These suspensions are mixed frequently over the 15 minutes at room temperature, then treated as above (centrifugation, dilution and quantitation).

B. Determination of Prodrug Cleavage in Serum:

Fresh control human serum, fresh control rat serum, and rhesus monkey plasma (heparinized and stored frozen) were preincubated at 37° C. for 15 min in a shaking water bath. The pH of the serum or plasma was measured using test strips. Then 25 $\mu$L aliquots of a solution in water of 17 (2 mg/mL) or its respective prodrug were added to each matrix resulting in a final solution volumn of 1 mL. Solutions were incubated at 37° C. for 1 hr, while removing 100 $\mu$L aliquotes at times=0, 15, 30, and 60 min post dose. The aliquotes were added to 200 $\mu$L 4% trichloroacetic acid, vortexed, and centrifuged for 10 min at 14,000 rpm in an Eppendorf microcentrifuge. Then 25 $\mu$L of each supernatant was analyzed via HPLC*. The degradation of 17 or its respective prodrug was measured as the percentage of the AUC at time t relative to the AUC at time=0. The rate of release of 17 from its respective prodrug was measured as percentage of the AUC of 17 observed at time t relative to a theoretical possible AUC of 17 as determined by a comparison to a standard concentration curve.

*HPLC conditions: Beckman Ultrasphere C18 column, 5 micron, 4.6 mm×25 cm. 1 mL/min of 95% 0.1 M ammonium acetate, pH=6,5% acetonitrile ramping to 25% acetonitrile over 20 min with peak detection at 254 and 280 nM.

Example 141

Biological Activity

In vitro Antibacterial Evaluation

Susceptibility Testing

Results of antimicrobial activity of 7-acylamino-3-heteroarylthio-3-cephem carboxylic acids are presented in Table 1 (MIC in $\mu$g/mL).

Compounds were evaluated for antimicrobial activity against a panel of bacterial strains using a broth microdilution assay performed as recommended by the NCCLS (1). The minimum inhibitory concentration (MIC) was defined as the lowest concentration of drug which prevented the growth of the bacteria.

The following 16 organisms constituted the primary panel of evaluation:

| Bacteria | Strain | Characteristic |
|---|---|---|
| Staphylococcus aureus | MSSA ATCC29213 | Wild type |
| Staphylococcus aureus | MSSA COL8A | PBP2A MRSA COL |
| Staphylococcus aureus | MSSA PC1 | β-lactamase overexpressor |
| Staphylococcus aureus | MSSA Smith | Wild type |
| Staphylococcus aureus | MRSA COL | PBP2A constitutive/ βla− |
| Staphylococcus aureus | MRSA 76 | PBP2A constitutive/ βla+ |
| Staphylococcus aureus | MRSA ATCC33593 | Wild type |
| Staphylococcus aureus | MRSA Spain#356 | Clinical isolate |
| Staphylococcus haemolyticus | sh005 | Clinical isolate |
| Enterococcus faecalis | ATCC29212 | Wild type |
| Enterococcus faecium | ATCC35667 | Wild type |
| Enterococcus faecium | VanA | Vancomycin$^R$ |
| Enterococcus faecalis | VanB | Vancomycin$^R$ |
| Enterococcus faecium | A491 | Clinical isolate/ Ampicillin$^R$ |
| Escherichia coli | ATCC25922 | Wild type |
| Pseudomonas aeruginosa | ATCC27853 | Wild type |

For this primary panel, the assay was performed in Mueller-Hinton Broth (MHB) with a final bacterial inoculum of $5 \times 10^5$ CFU/mL (from an early-log phase culture) and a final volume of 100 μL. Control drugs, including imipenem, vancomycin, Penicillin G, dicloxacillin (vs. MSSA ATCC29213 only), and new compounds were prepared at a concentration equivalent to 2-fold the desired final concentration. Dilution of compounds were prepared directly in the plates by serial 2-fold dilution using a multichannel pipette. Positive and negative growth control were included in each plate.

The bacterial inocula were prepared as follows. For each strain one isolated colony was used to inoculate a volume of 8 mL of Mueller-Hinton broth and these cultures were incubated overnight (20 h) at 35° C. in a shaking incubator. At the exception of Enterococcus strains, culture were then diluted 1:10 and allowed to grow for an additional one hour at 35° C. in a shaking incubator. The inocula were prepared by diluting the early log-phase (1 h) cultures 1:1000 with fresh Mueller-Hinton broth. E. faecium and E. faecalis were prepared by diluting overnight cultures 1:333 and 1:666, respectively, with fresh Mueller-Hinton broth. A volume of 50 μL of the inocula was added to each well. This procedure resulted in an inoculum of approximately $5 \times 10^5$ CFU/mL. The exact inocula were determined by applying 10 μL of 10-fold serial dilution of the bacterial suspensions on TSA. After overnight incubation at 35° C., colony forming units were manually counted.

Microtiter plates were incubated during 24 h at 35° C. and were read using a microtiterplate reader (Molecular Devices) at 650 nm as well as by visual observation using a microtiterplate reading mirror. The MIC is defined as the lowest concentration of compound at which the visible growth of the organism is completely inhibited.
1. National Committee for Clinical Laboratory Standards (NCCLS). 1997. Methods for Dilution of Antimicrobial Susceptibility Tests for Bacteria That Grow Aerobically— Fourth Edition; Approved Standard. NCCLS Document M7-A4, Vol. 17 No.2.

Serum Binding Determination

The approximate measurement of the degree of binding of the compound to human serum proteins can be achieved by determination of the effect of the addition of human serum to the medium in which the MIC values against a selected bacterial strain is determined. The ratio of the MIC value obtained in presence of added human serum to the MIC value determined without serum addition was used as a measure of serum binding and the results of such determination are presented below in Table 2.

In addition to the standard MIC determination described above, the staphylococcal strain ATCC29213 is also tested in a ratio 1:1, human serum:MHB to obtain a preliminary estimate of the bioactivity of test compounds in serum: The assay was performed in Human Serum and Mueller-Hinton Broth (HSMHB) with a final bacterial inoculum of $1 \times 10^6$ CFU/mL (from an early-log phase culture) and a final volume of 100 μL. Control drugs, including imipenem, vancomycin, dicloxacillin, and new compounds were prepared in double-concentrated Mueller-Hinton broth at a concentration equivalent to 4-fold the desired final concentration. Dilution of compounds were prepared directly in the plates by serial 2-fold dilution in double-concentrated Mueller-Hinton using a multichannel pipette. Positive and negative growth controls were included in each plate. A total of 50 μL of human serum was added to all wells S. aureus ATCC29213 was grown overnight in MHB (see, MIC determinations above), culture was then diluted 1:10 and allowed to grow for an additional one hour at 35° C. in a shaking incubator. The inoculum was prepared by diluting the early log-phase (1 h) culture 1:100 with fresh double-concentrated Mueller-Hinton broth. A volume of 25 μL of the inoculum was added to each well. This procedure resulted in an inoculum of approximately $1 \times 10^6$ CFU/mL. The exact inoculum was determined by applying 10 μl of 10-fold serial dilution of the bacterial suspension on TSA. After overnight incubation at 35° C., colony forming units were manually counted.

The more accurate measurement of binding of selected cephalosporin compounds was performed using HPLC as described below. Corresponding values in Table 2 represent percentage of cephalosporin compound which was found to be bound to serum proteins.
1. Serum is placed in a shaking water bath preheated to 37±2° C. for 5 to 10 minutes to heat serum to 37° C. Serum pH is measured and recorded, while serum is 37° C. using pH paper. Measurements are taken twice, 3 minutes apart. If the pH is not 7.4±0.4 then the pH is adjusted by blowing 5% $CO_2$/95% $O_2$ over the serum. After blowing for several minutes, serum is heated to 37° C. and measurements are taken twice, 3 minutes apart using pH paper to determine the pH. Store at 4° C. The serum is stable for 7 days. Always check the pH before each use.
2. Before any centrifugation, the centrifuge temperature must be adjusted to 25±2° C. Preheat the centrifuge by spinning for 45 minutes at the same speed to be used in the assay (1900 g) with two tubes of water in the rotor and the temperature set to 25° C. When the centrifuge stops immediately check the temperature of the tubes of water with a calibrated thermometer. The temperature of the tubes of water must be 25±2° C. In the event the temperature does not meet the above criteria adjust the temperature setting appropriately and spin for another 45 minutes. Continue spinning and measuring the temperature and adjusting the setting until the temperature is 25±2° C.
3. Prepare blank ultrafiltrate by pipetting blank pH 7.4 serum into an Amicon Centrifree Micropartition devices, centrifuge: fixed angle rotor, 1900 g, 25° C. for 20 minutes. Heat ultrafiltrate in a shaking water bath preheated to 37° C. Measure ultrafiltrate pH and adjust to the pH of the serum (7.4±0.2).

4. Pipette 190 ul of blank ultrafiltrate into a set of labeled 1.7 mL polypropylene microfuge tubes for 3 of each level. Pipette 10 µL of the appropriate standard stock 50, 200, 1000 µg/mL to make standards 2.5, 10, and 50 µg/mL respectively. Vortex each tube well. One set of the standard samples are mixed 1:1 with 0.2 M acetic acid and injected onto the HPLC (MSTD). These samples are the membrane standards and will be used to compare to the other standards. Pipette 190 ul of ultrafiltrate and spike with 10 ul of whatever solution (e.g. water) the standards are prepared in to make the zero standard.
5. Pipette 475 µL of blank heated pH 7.4 serum into a set of labeled 1.7 mL polypropylene microfuge tubes for 2 of each (Serum A and Serum B). Pipette 25 µL of the 1000 µg/mL standard stock into each tube, vortex each tube well to make serum standard 50 µg/mL. Remove 100 µL of serum and deproteinate with 200 µL 4% TCA while vortexing to make serum time 0 (serum 50, T0). Place serum tubes in a shaking water bath at 37° C. for 10 minutes. Pipet 100 µL of serum out and deproteinate with 200 µL 4% TCA, to make serum time 10 min (serum 50, T10). Pipet 200 ul serum standard 50 µg/mL into an ultrafiltration device, which is not treated with TCA, to determine free drug in samples (Rat Serum 50).
6. Transfer serum and standard samples to labeled Amicon Centrifree Micropartition filters, and centrifuge: 1900 g, 25° C. for 10 minutes. The extracted serum samples (T0 and T10) are spun down and supernatant is loaded into HPLC vials.
7. 100 µL of ultrafiltrate sample and 100 µL of 0.2 M acetic acid were mixed together to stabilize the compound in ultrafiltrate.
8. Transfer entire stabilized ultrafiltrate solution to a labeled autoinjector HPLC vial cap with Teflon septa, and inject on HPLC.

Calculations:

Peak height or area is used in a weighted linear regression.

High levels of binding to human serum proteins limits the concentration of compound available for antibacterial activity in the body. Therefore compounds with levels of human serum binding ≦90% are preferred. Data presented in Table 2 shows that among the 7-acylamino-3-heteroarylthio-3-cephem carboxylic acids which are the subject of the present invention for which human serum binding was determined, with the exception of compounds 23 and 29, the levels of binding are in the desired range. Even more preferred is the level of binding to human serum proteins ≦80% which provides even higher concentration of unbound compound available for antibacterial activity in the body. Data presented in Table 2 shows that compounds 3, 14, 17, 18, 19, and 25 exhibit level of binding to human serum proteins ≦80%.

In vitro Stability of Compounds in Rat Serum

In general, compounds from the class of 7-acylamino-3-heteroarylthio-3-cephem carboxylic acids have higher chemical reactivity and lower stability towards chemical or enzymatic decomposition than most typical cephalosporins. Many of them were found to have limited stability in vitro in rat serum. Results shown in Table 2 represent percentage loss of the initial amount of cephalosporin compound upon 60 min incubation in rat serum.

Procedure for measuring degree of degradation of cephalosporin compounds in rat serum was as follows:

Fresh control rat serum (heparinized and stored frozen) is preincubated at 37° C. for 15 min in a shaking water bath. pH is measured using test strips. 25 µL of a 2 mg/mL solution cephalosporin compound (in water) of is then added to each matrix to make 1000 µL. Solutions were incubated at 37° C. 100 ul of solution was taken out at time=0, 15, 30, and 60 min post dose and added 200 µL 4% trichloroacetic acid, vortexed, and centrifuged for 10 min at 14,000 rpm in an Eppendorf microcentrifuge. 25 µL of each supernatant was injected onto HPLC. Experiment was repeated using 25 µL of a 0.2 mg/mL cephalosporin compound. Degradation is measured as the percentage of HPLC peak area at time t relative to peak area at time 0.

HPLC conditions: Beckman Ultrasphere C18 column. 5 u. 4.6 mm×25 cm. 1 mL/min of 95% 0.1 M ammonium acetate, pH 6, 5% ACN going to 75% buffer/organic over 20 min. UV monitored at 254 and 280 nm.

Certain combinations of 7-acylamino-substitution and 3-heteroarylthio-substitution at the cephalosporin system result in improved stability of 7-acylamino-3-heteroarylthio-3-cephem carboxylic acid compounds. Examples of such compounds (Table 2) are Compound 3, Compound 13, Compound 14, Compound 15, Compound 17, Compound 21, Compound 23, Compound 25, and Compound 27. The names and structures of these compounds are listed in section II of the Detailed Description of the Preferred Embodiments, above.

In vivo Evaluation

Pharmacokinetic Evaluation in Rat

Improvements in serum stability of certain compounds from the class of 7-acylamino-3-heteroarylthio-3-cephem carboxylic acids over other compounds from this class are the important factors determining improved pharmacokinetic parameters of such compounds.

Although serum stability is recognized as only one of the potential factors influencing clearance of compound from the body, the positive effect of increased serum stability on clearance of certain compounds from the class of 7-acylamino-3-heteroarylthio-3-cephem carboxylic acids determined in rats is substantial.

Determination of clearance of cephalosporin compounds was performed following an example protocol described below which was used for determination of clearance of compound 17.

Four male SD rats with femoral and jugular vein catheters were obtained from Hilltop Lab Animals, Inc. (Scottdale, Pa.). The catheters in the femoral and jugular veins were filled with 10 units/mL heparin in saline, and kept patent by changing the solution daily. The animals were quarantined for a minimum of two days prior to use, and were maintained on a 12-h light:dark schedule with constant access to food and water before and during the study. On the day of dosing, the animals weighed 212±0.005 g (mean±s.d.).

All animal experimentation was conducted in accordance with the NIH Guide for the Care and Use of Laboratory Animals.

A 4 mg/mL (active component) dosing solution of mesylate salt of compound 17 was prepared in sterile saline for injection. After a 0.2 mL preinjection blood sample was collected from the jugular catheter, 20 mg/kg over 20 min as a 5 mL/kg infusion was initiated through the femoral catheter. Blood samples (0.2 mL aliquots) were collected from the jugular vein catheter 5, 15, 20, 25, 30, and 45 min, and 1, 2, 3, and 4 h after the start of the infusion. The blood was centrifuged for 10 min and the serum was stored ≦−70° C. until analysis by HPLC.

The plasma concentrations from individual animals were fit to a two-compartment model with zero order input and first-order elimination from the central compartment using weighted nonlinear regression (WinNonlin, Pharsight, Palo Alto, Calif.). Pharmacokinetic parameters were calculated from the fitted parameters using standard equations (Gibaldi M, Perrier D. 1982. Pharmacokinetics, $2^{nd}$ ed., Marcel Dekker Inc., New York.).

Efficacy Evaluations

Compounds with superior activity in vitro when compared to reference antibiotics, are further evaluated in a murine model for lethal bacteremic peritonitis following the procedure described below.

10 mice/group were injected intraperitoneally with $2.98 \times 10^7$ cfu S. aureus ATCC 13709 (Smith diffuse) and treated at 0 and 2 hrs post-challenge with serial two-fold doses of new cephalosporin antibiotic, imipenem and vancomycin subcutaneously in order to determine the $ED_{50}$. Male Swiss-Webster mice weighing originally 24.2–26.1 g were obtained from Charles Rivers Labs, Hollister, Calif. Mice were housed 10 per cage and given free access to water and mouse chow.

Staphylococcus aureus ATCC 13709 (Smith diffuse) was grown overnight at 37° C. in Brain-heart Infusion broth (BHIB). The following morning, it was subcultured to fresh BHIB and incubated for 4–5 h at 37° C. The log-phase growth cells were washed once with physiological saline and adjusted to the desired concentration by correlation of absorbency at OD 600 nm with predetermined plate counts (NCCLS, 1994). The cell suspension was mixed with an equal volume of sterile 14% hog-gastric mucin (2). Inoculum was kept in an ice bath until used (<1 h).

Mice were challenged via an injection of 0.5 mL bacterial suspension intraperitoneally. The bacterial challenge was $2.98 \times 10^7$ cfu/mouse.

Imipenem (Primaxin IV; Lot 7294A), vancomycin (Vancocin; Lot 8MU60W), and new cephalosporin antibiotic were prepared by serial two-fold dilutions to concentrations of 0.078–0.005 mg/mL, 1.2–0.075 mg/mL, 0.3–0.02 mg/mL, 0.3–0.02 mg/mL and 0.3–0.02 mg/mL respectively in sterile water (1). All antibiotics were administered subcutaneously in 0.1 mL volumes at 0 and 2 hours post-challenge. Concentrations of all compounds are based on the weight of the bioactive ingredients.

The 50% effective dose ($ED_{50}$) was calculated by the probit method (3) utilizing a program entitled Probit (Nycomed-Salutar).

The names and structures of the compounds listed by their compound number in Tables 1 and 2, below, are shown in section II of the Detailed Description of the Preferred Embodiments, above.

TABLE 1

Antimicrobial Properties of 7-Acylamido-3-heteroarylthiocephems

| Organism | Imipenem | 1 | 2 | 3 | 4 | 5 | 6 |
|---|---|---|---|---|---|---|---|
| S. aureus ATCC 29213 | ≤0.008 | 0.13 | 0.25 | 0.25 | 0.13 | 0.25 | 0.5 |
| S. aureus Col8A ($Meth^S$)($lac^-$) | 0.015 | 0.25 | 0.25 | 0.25 | 0.13 | 0.25 | 0.5 |
| S. aureus PC1 ($Meth^S$)($lac^+$) | 0.015 | 0.25 | 0.25 | 0.25 | 0.13 | 0.25 | 0.5 |
| S. aureus ATCC 13709 ($Meth^S$) | ≤0.008 | 0.13 | 0.13 | 0.13 | 0.13 | 0.13 | 0.25 |
| S. aureus Col ($Meth^R$)($lac^-$) | 32 | 0.5 | 2 | 1 | 2 | 4 | 16 |
| S. aureus 76 ($Meth^R$)($lac^+$) | 32 | 1 | 4 | 1 | 2 | 4 | 16 |
| S. aureus ATCC 33593 ($Meth^R$) | 32 | 1 | 1 | 2 | 1 | 4 | 8 |
| S. aureus Spain #356 ($Meth^R$) | 32 | 1 | 2 | 1 | 2 | 4 | 16 |
| S. haemolyticus 05 ($Meth^R$) | 64 | 1 | 4 | 1 | 4 | 8 | 32 |
| E. faecalis ATCC 29212 | ≤0.25 | 0.06 | 0.25 | 0.13 | 0.25 | 0.5 | 2 |
| E. faecium ATCC 35667 | 4 | 0.5 | 4 | 1 | 0.25 | 4 | 8 |
| E. faecium VanA ($Van^R$) | 4 | 2 | 4 | 8 | 0.5 | 4 | 8 |
| E. faecalis VanB ($Van^R$) | 0.5 | 0.25 | 1 | 0.25 | 0.5 | 1 | 4 |
| E. faecium A491 ($Amp^R$) | >128 | 4 | >32 | >32 | — | >32 | >32 |
| E. coli ATCC25992 | ≤0.25 | 0.5 | 32 | 4 | 4 | 32 | 16 |
| P. aeruginosa ATCC 27853 | 1 | >32 | >32 | 4 | >32 | >32 | >32 |

| Organism | Imipenem | 7 | 8 | 9 | 10 | 11 | 12 |
|---|---|---|---|---|---|---|---|
| S. aureus ATCC 29213 | ≤0.008 | 0.25 | 1 | 0.5 | 0.5 | 0.06 | 0.5 |
| S. aureus Col8A($Meth^S$)($lac^-$) | 0.015 | 0.25 | 1 | 0.25 | 0.25 | 0.13 | 0.5 |
| S. aureus PC1 ($Meth^S$)($lac^+$) | 0.015 | 0.25 | 1 | 0.5 | 0.5 | 0.13 | 0.13 |
| S. aureus ATCC 13709 ($Meth^S$) | 0.008 | 0.25 | 0.5 | 0.25 | 0.13 | 0.13 | 0.25 |
| S. aureus Col ($Meth^R$)($lac^-$) | 32 | 2 | 16 | 2 | 2 | 0.5 | 1 |
| S. aureus 76 ($Meth^R$)($lac^+$) | 32 | 2 | 16 | 4 | 2 | 0.5 | 1 |
| S. aureus ATCC 33593 ($Meth^R$) | 32 | 2 | 8 | 4 | 2 | 0.5 | 1 |
| S. aureus Spain #356 ($Meth^R$) | 32 | 2 | 16 | 4 | 4 | 0.5 | 1 |
| S. haemolyticus 05 ($Meth^R$) | 64 | 2 | 32 | 4 | 4 | 0.5 | 2 |
| E. faecalis ATCC 29212 | ≤0.25 | 2 | 8 | 4 | 0.13 | 0.06 | — |
| E. faecium ATCC 35667 | 4 | 8 | 16 | 8 | 1 | 0.5 | 0.5 |
| E. faecium VanA ($Van^R$) | 4 | 8 | 32 | 16 | 2 | 4 | 1 |
| E. faecalis VanB ($Van^R$) | 0.5 | 4 | 16 | 8 | 0.25 | 0.06 | 0.13 |
| E. faecium A491 ($Amp^R$) | >128 | >32 | >32 | >32 | 8 | 4 | 4 |
| E. coli ATCC25992 | ≤0.25 | 4 | 16 | 0.25 | 1 | 2 | 4 |
| P. aeruginosa ATCC 27853 | 1 | >32 | >32 | >32 | 16 | 2 | >32 |

| Organism | Imipenem | 13 | 14 | 15 | 16 | 17 | 18 |
|---|---|---|---|---|---|---|---|
| S. aureus ATCC 29213 | ≤0.008 | 0.25 | 0.13 | 0.13 | 0.13 | 0.25 | 0.13 |
| S. aureus Col8A($Meth^S$)($lac^-$) | 0.015 | 0.25 | 0.25 | 0.125 | 0.25 | 0.25 | 0.13 |
| S. aureus PC1 ($Meth^S$)($lac^+$) | 0.015 | 0.25 | 0.13 | 0.13 | 0.13 | 0.25 | 0.13 |
| S. aureus ATCC 13709 ($Meth^S$) | ≤0.008 | 0.13 | 0.13 | 0.06 | 0.13 | 0.25 | 0.13 |
| S. aureus Col ($Meth^R$)($lac^-$) | 32 | 0.5 | 1 | 0.5 | 1 | 1 | 1 |
| S. aureus 76 ($Meth^R$)($lac^+$) | 32 | 1 | 1 | 0.5 | 1 | 1 | 1 |
| S. aureus ATCC 33593 ($Meth^R$) | 32 | 1 | 1 | 0.5 | 1 | 1 | 1 |
| S. aureus Spain #356 ($Meth^R$) | 32 | 1 | 1 | 0.5 | 1 | 1 | 1 |

TABLE 1-continued

Antimicrobial Properties of 7-Acylamido-3-heteroarylthiocephems

| Organism | | | | | | | |
|---|---|---|---|---|---|---|---|
| S. haemolyticus 05 (Meth$^R$) | 64 | 1 | 2 | 1 | 1 | 2 | 2 |
| E. faecalis ATCC 29212 | ≦0.25 | 0.06 | 1 | 0.06 | 0.06 | 1 | 0.13 |
| E. faecium ATCC 35667 | 4 | 0.5 | 0.5 | 0.25 | 0.5 | 1 | 0.5 |
| E. faecium VanA (Van$^R$) | 4 | 1 | 1 | 0.5 | 4 | 2 | 1 |
| E. faecalis VanB (Van$^R$) | 0.5 | 0.13 | 0.25 | 0.06 | 0.06 | 0.5 | 0.25 |
| E. faecium A491 (Amp$^R$) | >128 | 8 | 32 | 4 | 16 | >32 | 32 |
| E. coli ATCC25992 | ≦0.25 | 4 | 1 | 4 | 4 | 1 | 0.5 |
| P. aeruginosa ATCC 27853 | 1 | 32 | >32 | >32 | 1 | >32 | >32 |

| Organism | Imipenem | 19 | 20 | 21 | 22 | 23 | 24 |
|---|---|---|---|---|---|---|---|
| S. aureus ATCC 29213 | ≦0.008 | 0.5 | 0.25 | 0.13 | 0.25 | 0.13 | 0.25 |
| S. aureus Col8A(Meth$^S$)(lac$^-$) | 0.015 | 0.5 | 0.25 | 0.25 | 0.25 | 0.13 | 0.5 |
| S. aureus PC1 (Meth$^S$)(lac$^+$) | 0.015 | 0.5 | 0.25 | 0.25 | 0.13 | 0.13 | 0.25 |
| S. aureus ATCC 13709 (Meth$^S$) | ≦0.008 | 0.5 | 0.13 | 0.13 | — | 0.06 | 0.25 |
| S. aureus Col (Meth$^R$)(lac$^-$) | 32 | 2 | 0.5 | 1 | 2 | 1 | 1 |
| S. aureus 76 (Meth$^R$)(lac$^+$) | 32 | 2 | 1 | 1 | 2 | 2 | 1 |
| S. aureus ATCC 33593 (Meth$^R$) | 32 | 2 | 1 | 1 | 2 | 1 | 2 |
| S. aureus Spain #356 (Meth$^R$) | 32 | 2 | 1 | 1 | 2 | 2 | 2 |
| S. haemolyticus 05 (Meth$^R$) | 64 | 4 | 2 | 2 | 4 | 4 | 2 |
| E. faecalis ATCC 29212 | ≦0.25 | 0.5 | 0.06 | 0.13 | 0.13 | 0.25 | 0.25 |
| E. faecium ATCC 35667 | 4 | 2 | 0.5 | 1 | 0.25 | 2 | 1 |
| E. faecium VanA (Van$^R$) | 4 | 4 | 0.25 | 2 | 1 | 2 | 2 |
| E. faecalis VanB (Van$^R$) | 0.5 | 1 | 0.13 | 0.5 | 0.25 | 0.5 | 0.5 |
| E. faecium A491 (Amp$^R$) | >128 | >32 | 8 | 32 | 8 | — | 32 |
| E. coli ATCC25992 | ≦0.25 | 4 | 8 | 4 | 4 | 16 | 16 |
| P. aeruginosa ATCC 27853 | 1 | >32 | >32 | 32 | >32 | >32 | >32 |

| Organism | Imipenem | 25 | 26 | 27 | 28 | 29 |
|---|---|---|---|---|---|---|
| S. aureus ATCC 29213 | ≦0.008 | 0.25 | 0.06 | 0.5 | 0.5 | 0.125 |
| S. aureus Col8A(Meth$^S$)(lac$^-$) | 0.015 | 0.13 | 0.06 | 0.25 | 0.25 | 0.125 |
| S. aureus PC1 (Meth$^S$)(lac$^+$) | 0.015 | 0.13 | 0.06 | 0.5 | 0.5 | 0.25 |
| S. aureus ATCC 13709 (Meth$^S$) | ≦0.008 | 0.13 | 0.06 | 0.25 | 0.13 | 0.125 |
| S. aureus Col (Meth$^R$)(lac$^-$) | 32 | 1 | 0.25 | 8 | 8 | 1 |
| S. aureus 76 (Meth$^R$)(lac$^+$) | 32 | 1 | 0.5 | 8 | 8 | 1 |
| S. aureus ATCC 33593 (Meth$^R$) | 32 | 1 | 0.5 | 8 | 8 | 1 |
| S. aureus Spain #356 (Meth$^R$) | 32 | 1 | 0.5 | 16 | 8 | 2 |
| S. haemolyticus 05 (Meth$^R$) | 64 | 2 | 0.5 | 16 | 16 | 2 |
| E. faecalis ATCC 29212 | ≦0.25 | 0.13 | 0.06 | 2 | 0.5 | 0.25 |
| E. faecium ATCC 35667 | 4 | 0.5 | 0.5 | 8 | 4 | 2 |
| E. faecium VanA (Van$^R$) | 4 | 1 | 1 | 8 | 8 | 4 |
| E. faecalis VanB (Van$^R$) | 0.5 | 0.25 | 0.06 | 2 | 2 | 0.5 |
| E. faecium A491 (Amp$^R$) | >128 | 32 | 16 | >32 | >32 | >32 |
| E. coli ATCC25992 | ≦0.25 | 1 | 4 | 4 | 32 | 16 |
| P. aeruginosa ATCC 27853 | 1 | >32 | 4 | >32 | >32 | >32 |

TABLE 2

Serum effects and in vivo properties of 7-Acylamido-3-heteroarylthiocephems

| Cmpd | Serum Binding[a] | | | Human serum binding effect[b] | Stability in rat serum[c] | Pharmacokinetics[d] | | Efficacy in murine septicemia[e] | |
|---|---|---|---|---|---|---|---|---|---|
| | rat | rhesus | human | | | Clearance (L/h/kg) | Dose (mg/kg) | Dose (mg/kg)/ % survival | ED$_{50}$ |
| Van. | | | 55 | 2 | | | | 10/100<br>5/100<br>2.5/60<br>1.25/20<br>0.625/10 | 2.41 |
| 1 | | | | 64 | | | | | |
| 2 | | | | 4 | | | | | |
| 3 | 56 | 93 | 88 | 4 | 3% | 0.95 | 27.5 | 2.5/100<br>1.25/90<br>0.625/90<br>0.312/50<br>0.165/40<br>0.078/30 | 0.39 |

TABLE 2-continued

Serum effects and in vivo properties of 7-Acylamido-3-heteroarylthiocephems

| | Serum Binding[a] | | | Human serum binding effect[b] | Stability in rat serum[c] | Pharmacokinetics[d] | | Efficacy in murine septicemia[e] | |
|---|---|---|---|---|---|---|---|---|---|
| Cmpd | rat | rhesus | human | | | Clearance (L/h/kg) | Dose (mg/kg) | Dose (mg/kg)/ % survival | ED$_{50}$ |
| 4 | | | | 3 | | | | | |
| 5 | | | | 4 | | | | | |
| 6 | | | | 128 | | | | | |
| 7 | | | | | | | | | |
| 8 | | | | 128 | | | | | |
| 9 | | | | 2 | | | | | |
| 10 | | | | 1 | | | | | |
| 11 | | | 83 | 4 | 47% | | | | |
| 12 | | | | 256 | | | | | |
| 13 | 85 | | 90 | 2 | 9% | 0.79 | 20.0 | 5/100 2.5/100 1.25/100 0.625/100 0.312/30 | <0.31 |
| 14 | | | 60 | 2 | 10% | | | 5/100 2.5/100 1.25/100 0.625/100 0.312/90 | <0.31 |
| 15 | 76 | 88 | 83 | 2 | 38% | | | | |
| 16 | | | | 1 | | | | | |
| 17 | 74 | 81 | 66 | 2 | 2% | 0.5 | 16.4 | 2.0/100 1.0/100 0.5/50 0.25/20 0.12/10 | 0.39 |
| 18 | 55 | 67 | 66 | 2 | 23% | 2.17 | 20.0 | 5/100 2.5/100 1.25/100 0.625/60 0.312/30 | 0.46 |
| 19 | 76 | 83 | 68 | 2 | 26% | 1.25 | 42.5 | 1.25/100 0.625/80 0.312/20 0.156/20 0.078/20 | 1.29 |
| 20 | 71 | 77 | 84 | 3 | 70% | 1.59 | 20.0 | 2.5/80 1.25/58 0.625/30 0.312/10 0.156/20 | 1.00 |
| 21 | 97 | 97 | 90 | 2 | 3% | 0.73 | 20.0 | 5/80 2.5/80 1.25/70 0.625/0 0.312/0 | 0.79 |
| 22 | | | 82 | 4 | | | | 5/100 205/100 1.25/40 0.625/30 0.312/30 | 0.83 |
| 23 | 77 | 93 | 94 | | 19% | 0.81 | 20.0 | 5/100 2.5/100 1.25/100 6.25/70 0.312/40 | 0.39 |
| 24 | 52 | | 88 | | 66% | 2.85 | 20.0 | 10/100 5/100 2.5/100 1.25/90 0.625/30 | 0.76 |
| 25 | 35 | 55 | 47 | 1 | 45% | 1.12 | 20.0 | 5/100 2.5/100 1.25/100 0.625/100 0.312/80 | <0.31 |

TABLE 2-continued

Serum effects and in vivo properties of 7-Acylamido-3-heteroarylthiocephems

| | Serum Binding[a] | | | Human serum binding effect[b] | Stability in rat serum[c] | Pharmacokinetics[d] | | Efficacy in murine septicemia[e] | |
|---|---|---|---|---|---|---|---|---|---|
| Cmpd | rat | rhesus | human | | | Clearance (L/h/kg) | Dose (mg/kg) | Dose (mg/kg)/ % survival | $ED_{50}$ |
| 26 | | | | 2 | | | | | |
| 27 | | | | 4 | | | | | |
| 28 | | | | | | | | | |
| 29 | | | 97 | | | | | | |
| Imip.[g] | | | | 2 | 20% | | | 0.625/100<br>0.312/100<br>0.156/100<br>0.078/40<br>0.039/20 | 0.07 |

LEGEND a. % of compound bound to serum as determined by HPLC (see "Serum binding determination" for details).
b. Ratio of MIC value determined with and without human serum added for *S. aureus* ATCC29213.
c. % loss after 60 min exposure to rat serum as determined by HPLC (See "In vitro stability of compounds in rat serum" for details).
d. Clearance in rat determined at given dose (see "Pharmacokinetic evaluation in rat" for details).
e. Efficacy in treatment of experimental infection in mice (see "Efficacy evaluation" for details).
f. Vancomycin
g. Imipenem

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual, member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. A prodrug of formula III or formula IV (III)

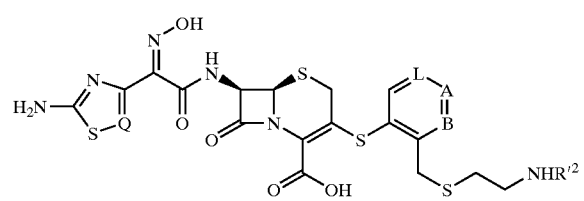

(IV)

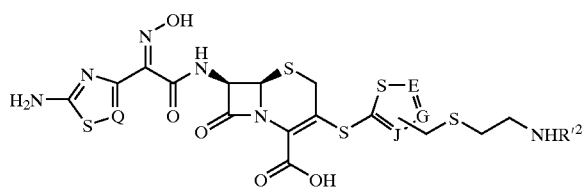

or a pharmaceutically acceptable salt thereof, wherein:

$R'^2$ is an acyl group that is cleaved by an enzyme found in mammals,

A, B, L, G, E, and J are each independently nitrogen or carbon, wherein said specific juxtaposition of groups A, B, and L forms a heterocyclic group selected from the group consisting of

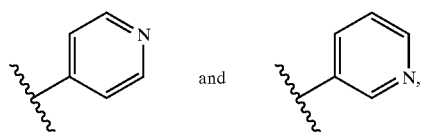

wherein said specific juxtaposition of groups E, G, and J forms a heterocyclic group selected from the group consisting of

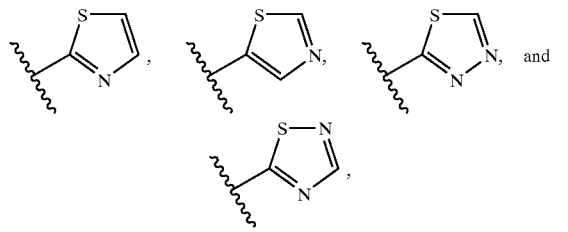

provided that the group —CH$_2$—S—CH$_2$CH$_2$NHR'$^2$ is attached only to a carbon atom of said heterocyclic group;

Q is selected from the group consisting of nitrogen and —CX, wherein X is selected from the group consisting of hydrogen and chlorine.

2. The prodrug or salt thereof of claim 1, wherein R'$^2$ is selected from the group consisting of —C(O)—R$^{88}$, —C(O)—OR$^{89}$, —C(O)—CH(NHR'$^3$)-alk$_4$, and

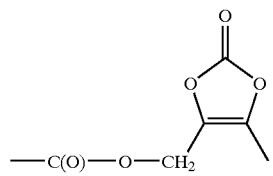

wherein

R$^{88}$ is 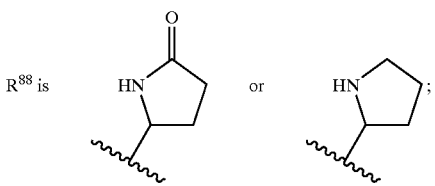

R'$^3$ is selected from the group consisting of hydrogen, —C(O)—OR$^{89}$, and —C(O)—CH(NH$_2$)-alk$_4$;

alk$_4$ is selected from the group consisting of hydrogen, and optionally substituted alkyl, wherein said alkyl is optionally substituted with one or more substituents selected from the group consisting of hydrogen, phenyl, —COOH, —C(O)—OR$^{89}$, C(O)NH$_2$, —OH, —SH, —NH$_2$, and

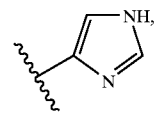

R$^{89}$ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsisyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

3. The prodrug or salt thereof of claim 1, wherein said compound has the structure set forth in formula V

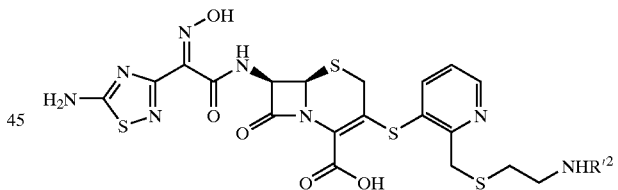

or a pharmaceutically acceptable salt thereof, wherein

R'$^2$ is an acyl group that is cleaved by an enzyme found in mammals.

4. The prodrug or salt thereof of claim 3, where R'$^2$ is selected from the group consisting of —C(O)—R$^{88}$, —C(O)—OR$^{89}$, —C(O)—CH(NHR'$^3$)-alk$_4$, and

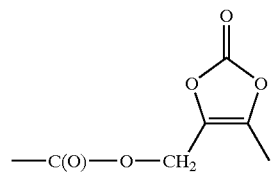

wherein

R⁸⁸ is 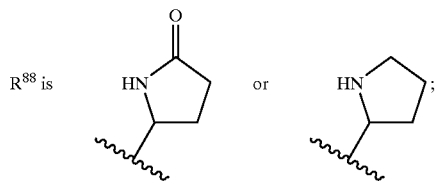

R'³ is selected from the group consisting of hydrogen, —C(O)—OR⁸⁹, and —C(O)—CH(NH₂)-alk₄;
alk₄ is selected from the group consisting of hydrogen, and optionally substituted alkyl, wherein said alkyl is optionally substituted with one or more substituents selected from the group consisting of hydrogen, phenyl, —COOH, —C(O)—OR⁸⁹, —C(O)NH₂, —OH, —SH, —NH₂, and

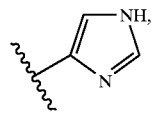

R⁸⁹ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsilyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

5. The prodrug or salt thereof of claim 4, wherein R'³ is selected from the group consisting of hydrogen, methyl, and —C(O)—CH(NH₂)CH₃.

6. The prodrug or salt thereof of claim 4, wherein alk₄ is selected from the group consisting of hydrogen, —CH₃, —CH(CH₃)₂, —CH₂OH, —CH₂NH₂, —CH₂CH₂NH₂, —CH₂CH₂CH₂NH₂, —CH₂CH₂CH₂CH₂NH₂, —CH₂COOH, —CH₂CH₂COOH, —CH₂—C(O)NH₂, —CH₂CH₂—C(O)NH₂, and

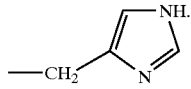

7. The prodrug of claim 3 selected from the group consisting of:
(7R)-7-[(Z)-2-(5-amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-prolylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-(2-N-glycylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-[2-[2-N-(L)-aspartylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-(2-N-(L)-(Nα-methyl)alanylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-histidylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-valylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-asparagylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-lysylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-serylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-glutaminylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-(5-methyl-1,3-dioxolan-4-en-2-on-4-yl)methoxycarbonyl)aminoethylthiomethyl]pyrid-3-ylthio}-3-cephem-4-carboxylic acid, and
(7R)-7-[(Z)-2-(5-amino-1,2,4-thiadiazol-3-yl)-2-(hydroxyimino)acetamido]-3-{2-(2-N-(L)-pyroglutamylaminoethylthiomethyl]pyrid-3-ylthio}-3-cephem-4-carboxylic acid.

8. The prodrug of claim 3 selected from the group consisting of:
(7R)-7-[(Z)-2-(5-amino-1,2,4-thiadiazol-3-yl)-2-(hydroxyimino)acetamido]-3-{2-[2-N-(L)-ornithylaminoethylthiomethyl]pyrid-3-ylthio}-3-cephem-4-carboxylic acid,
(7R)-7-((Z)-2-(5-amino-1,2,4-thiadiazol-3-yl)-2-(hydroxyimino)acetamido]-3-{2-[2-N-(L)-aspartylamidoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-lysylaminoethylthiomethyl]pyrid-3-ylthio}-3-cephem-4-carboxylic acid,
(7R)-7-[(Z)-2-(5-amino-1,2,4-thiadiazol-3-yl)-2-(hydroxyimino)acetamido]-3-{2-[2-N-(L)-glutaminylaminoethylthiomethyl]pyrid-3-ylthio}-3-cephem-4-carboxylic acid, and
(7R)-7-[(Z)-2-(5-amino-1,2,4-thiadiazol-3-yl)-2-(hydroxyimino)acetamido]-3-{2-(2-(5-methyl-1,3- dioxolan-4-en-2-on-4-yl)methoxycarbonyl)
aminoethylthiomethyl]pyrid-3-ylthio}-3-cephem-4-
carboxylic acid.

9. An intermediate compound having the following formula:

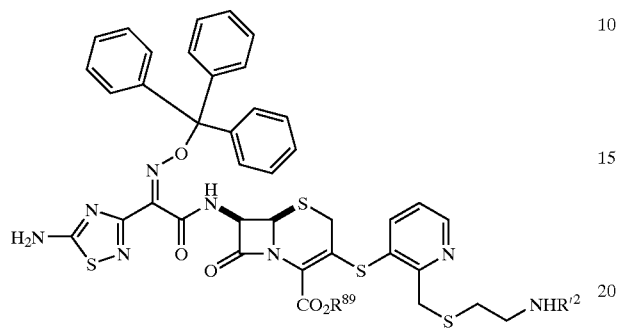

wherein R'² is selected from the group consisting hydrogen —C(O)—R⁸⁸, —C(O)—OR⁸⁹, —C(O)—CH(NHR'³)-alk₄, and

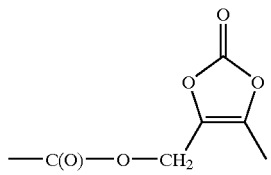

wherein:

R⁸⁸ is 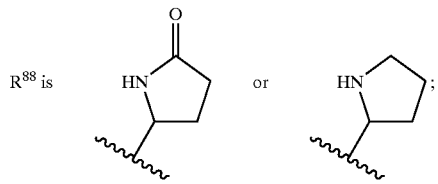

R'³ is selected from the group consisting of hydrogen, —C(O)—OR⁸⁹, and —C(O)—CH(NH₂)-alk₄;
alk₄ is selected from the group consisting of hydrogen, and optionally substituted alkyl, wherein said alkyl is optionally substituted with one or more substituents selected from the group consisting of hydrogen, phenyl, —COOH, —C(O)—OR⁸⁹, —C(O)NH₂, —OH, —SH, —NH₂, and

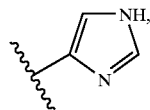

R⁸⁹ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsilyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

10. The prodrug or salt thereof of claim 1 having the chemical structure

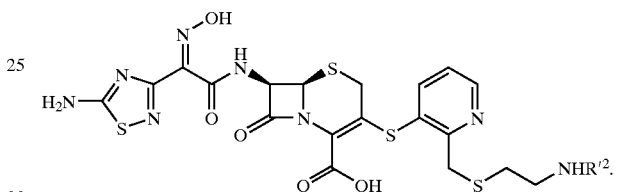

R'² an acyl group that is cleaved by an enzyme found in mammals.

11. The prodrug or salt thereof of claim 10, where R'² is selected from the group consisting of —C(O)—R⁸⁸, —C(O)—OR⁸⁹, —C(O)—CH(NHR'³)-alk₄, and

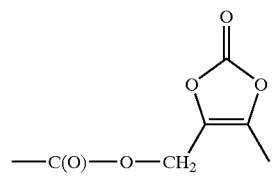

wherein

R⁸⁸ is 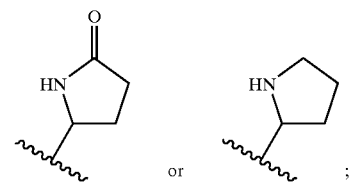

R'³ is selected from the group consisting of hydrogen, —C(O)—OR⁸⁹, and —C(O)—CH(NH₂)-alk₄;

alk₄ is selected from the group consisting of hydrogen, and optionally substituted alkyl, wherein said alkyl is optionally substituted with one or more substituents selected from the group consisting of hydrogen, phenyl, —COOH, —C(O)—OR⁸⁹, —C(O)NH₂, —OH, —SH, —NH₂, and

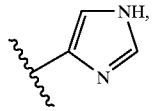

R⁸⁹ is selected from the group consisting of benzhydryl, t-butyl, allyl, p-nitrobenzyl, benzyl, p- or o-nitrobenzyl, 2,2,2-trichloroethyl, allyl, cinnamyl, benzhydryl, 2-chloroallyl, t-amyl, trityl, 4-methoxytrityl, 4,4'-dimethoxytrityl, trimethylsilyl, t-butyldimethylsilyl, β-(trimethylsilyl)ethyl, 4- or 2-methoxybenzyl, 2,4-dimethoxybenzyl, 3,4-dimethoxybenzyl, 2,4,6-trimethoxybenzyl, methoxymethyl, and 3,3-dimethylallyl.

12. A compound selected from the group consisting of:
(7R)-7-((Z)-2-(2-amino-5-chlorothiazol-4-yl)-2-(hydroxylamino)acetamido-3-(2-aminoethylthio-1,3,4-thiadiazol-5-ylthio)-3-cephem-4-carboxylic acid,
(7R)-7-[(Z)-2-(2-aminopyrid-6-yl)-2-(hydroxylamino)acetamido]-3-[4-(2-aminoethylthiomethyl)-2-methyl-1,3-thiazol-5-ylthio]-3-cephem-4-carboxylic acid,
(7R)-7-((Z)-2-(2-amino-5-chlorothiazol-4-yl)-2-(hydroxylamino)acetamido]-3-[4-(2-aminoethylthiomethyl)-2-amino-1,3-thiazol-5-ylthio]-3-cephem-4-carboxylic acid,
(7R)-7-[((Z)-2-(2-aminopyrid-6-yl)-2-(hydroxylamino)acetamido]-3-(4-(2-aminoethylthiomethyl)-1,3-thiazol-2-ylthio]-3-cephem-4-carboxylic acid,
(7R)-7-[(Z)-2-(2-aminopyrid-6-yl)-2-(hydroxyimino)acetamido]-3-[4-(2-aminoethylthiomethyl)-2-methoxy-1,3-thiazol-5-ylthio]-3-cephem-4-carboxylic acid,
(7R)-7-[(Z)-2-(2-aminopyrid-6-yl)-2-(hydroxylamino)acetamido]-3-[2-(2-aminoethylthio)-pyridazin-6-ylthio]-3-cephem-4-carboxylic acid,
(7R)-7-[(Z)-2-(2-aminopyrid-6-yl)-2-(hydroxylamino)acetamido]-3-[2-(2-aminoethylthio)-pyridazin-3-ylthio]-3-cephem-4-carboxylic acid,
(7R)-7-[(Z)-2-(2-aminopyrid-6-yl)-2-(hydroxylamino)acetamido]-3-[2-(2-aminoethylthio)-pyrimidin-4-ylthio]-3-cephem-4-carboxylic acid,
(7R)-7-[(Z)-2-(2-aminothiazol-4-yl)-2-(hydroxyimino)acetamido]-3-[2-(2-aminoethylthiomethyl)-pyridazin-3-ylthio]-3-cephem-4-carboxylic acid,
(7R)-7-[(Z)-2-(2-amino-5-chlorothiazol-4-yl)-2-(hydroxylamino)acetamido]-3-(2-aminoethylthiomethyl-1,3,4-thiadiazol-5-ylthio)-3-cephem-4-carboxylic acid,
(7R)-7-[(Z)-2-(2-amino-5-chlorothiazol-4-yl)-2-(hydroxylamino)acetamido]-3-[4-(2-aminoethylthiomethyl)-2-aminoethylthio-1,3-thiazol-5-ylthio]-3-cephem-4-carboxylic acid,
(7R)-7-[(Z)-2-(2-amino-5-chlorothiazol-4-yl)-2-(hydroxyimino)acetamido]-3-[3-(2-aminoethylthiomethyl)-1,2,4-thiadiazol-5-ylthio]-3-cephem-4-carboxylic acid,
(7R)-7-[(Z)-2-(2-amino-5-chlorothiazol-4-yl)-2-(hydroxylamino)acetamido]-3-[2-(2-aminoethylthiomethyl)pyrid-3-ylthio]-3-cephem-4-carboxylic acid,
(7R)-7-[(Z)-2-(5-amino-1,2,4-thiadiazol-3-yl)-2-(hydroxylamino)acetamido]-3-[2-(2-guanidinoethylthiomethyl)pyrid-3-ylthio]-3-cephem-4-carboxylic acid,
(7R)-7-[(Z)-2-(2-amino-5-chlorothiazol-4-yl)-2-(hydroxyimino)acetamido]-3-[2-(2-guanidinoethylthiomethyl)pyrid-3-ylthio]-3-cephem-4-carboxylic acid,
(7R)-7-[(Z)-2-(2-amino-5-chlorothiazol-4-yl)-2-(hydroxylamino)acetamido]-3-[4-(2-aminoethylthiomethyl)-2-aminoethylamino-1,3-thiazol-5-ylthio]-3-cephem-4-carboxylic acid,
(7R)-7-[(Z)-2-(5-amino-1,2,4-thiadiazol-3-yl)-2-(hydroxylamino)acetamido]-3-[2-(2-aminoethylthiomethyl)pyrid-3-ylthio]-3-cephem-4-carboxylic acid,
(7R)-7-((Z)-2-(5-amino-1,2,4-thiadiazol-3-yl)-2-(hydroxylamino)acetamido]-3-[3-(2-aminoethylthiomethyl)pyrid-4-ylthio]-3-cephem-4-carboxylic acid,
(7R)-7-[(Z)-2-(2-amino-5-chlorothiazol-4-yl)-2-(hydroxylamino)acetamido]-3-[4-(2-aminoethylthiomethyl)pyrid-3-ylthio]-3-cephem-4-carboxylic acid,
(7R)-7-[(Z)-2-(2-aminopyrid-6-yl)-2-(hydroxylamino)acetamido]-3-(2-aminoethylthio-1,3,4-thiadiazol-5-ylthio)-3-cephem-4-carboxylic acid,
(7R)-7-[(Z)-2-(2-aminopyrid-6-yl)-2-(hydroxyimino)acetamido]-3-[4-(2-aminoethylthiomethyl)-1,3-thiazol-5-ylthio]-3-cephem-4-carboxylic acid,
(7R)-7-[(Z)-2-(2-aminopyrid-6-yl)-2-(hydroxyimino)acetamido]-3-[3-(2-aminoethylthiomethyl)pyrid-4-ylthio]-3-cephem-4-carboxylic acid,
(7R)-7-[(Z)-2-(5-amino-1,2,4-thiadiazol-3-yl)-2-(hydroxylamino)acetamido]-3-[3-(2-guanidinoethylthiomethyl)pyrid-4-ylthio]-3-cephem-4-carboxylic acid,
(7R)-7-[(Z)-2-(2-amino-5-chlorothiazol-4-yl)-2-(hydroxylamino)acetamido]-3-[4-(2-guanidinoethylthiomethyl)-2-amino-1,3-thiazol-5-ylthio]-3-cephem-4-carboxylic acid,
(7R)-7-[(Z)-2-(5-amino-1,2,4-thiadiazol-3-yl)-2-(hydroxylamino)acetamido]-3-[4-(2-aminoethylthiomethyl)pyrid-3-ylthio]-3-cephem-4-carboxylic acid,
(7R)-7-[(Z)-2-(2-aminopyrid-6-yl)-2-(hydroxyimino)acetamido]-3-[4-(2-aminoethylthiomethyl)pyrid-3-ylthio]-3-cephem-4-carboxylic acid, and
(7R)-7-[(Z)-2-(2-aminopyrid-6-yl)-2-(hydroxyimino)acetamido]-3-[2-chloro-4-(2-aminoethylthiomethyl)-1,3-thiazol-5-ylthio]-3-cephem-4-carboxylic acid.

13. A compound selected from the group consisting of:
(7R)-7[(Z)-2-(2-amino-5-chlorothiazol-4-yl)-2-(hydroxyimino)acetamido]-3-[4-(2-aminoethylthiomethyl)-2-amino-1,3-thiazol-5-ylthio]-3-cephem-4-carboxylic acid, (7R)-7[(Z)-2-(2-amino-5-chlorothiazol-4-yl)-2-(hydroxyimino)acetamido]-3-[2-(2-aminoethyl-thiomethyl)pyrid-3-ylthio]-3-cephem-4-carboxylic acid, (7R)-7[(Z)-2-(5-amino-1,2,4-thiadiazol-3-yl)-2-(hydroxyimino)acetamido]-3-[2-(2-guanidinoethyl-thiomethyl)pyrid-3-ylthio]-3-cephem-4-carboxylic acid, (7R)-7[(Z)-2-(2-amino-5-chlorothiazol-4-yl)-2-(hydroxyimino)acetamido]-3-[2-(2-guanidinoethyl-thiolmethyl)pyrid-3-ylthio]-3-cephem-4-carboxylic acid, (7R)-7[(Z)-2-(5-amino-1,2,4-thiadiazol-3-yl)-2-(hydroxyimino)acetamido]-3-[2-(2-aminoethyl-thiomethyl)pyrid-3-ylthio]-3-cephem-4-carboxylic acid, (7R)-7[(Z)-2-(2-amino-5-chlorothiazol-4-yl)-2-(hydroxyimino)acetamido]-3-[4-(2-aminoethyl-thiomethyl)pyrid-3-ylthio]-3-cephem-4-carboxylic acid, (7R)-7[(Z)-2-(2-aminopyrid-6-yl)-2-(hydroxyimino)acetamido]-3-[4-(2-aminoethylthiomethyl)-1,3-thiazol-5-ylthio]-3-cephem-4-carboxylic acid, (7R)-7[(Z)-2-(5-amino-1,2,4-thiadiazol-3-yl)-2-(hydroxyimino)acetamido]-3-[2-(2-guanidinoethyl-thiomethyl)pyrid-4-ylthio]-3-cephem-4-carboxylic acid, and (7R)-7-[(Z)-2-(5-amino-1,2,4-thiadiazol-3-yl)-2-(hydroxyimino)acetamido]-3-[4-(2-aminoethyl-thiomethyl)pyrid-3-ylthio]-3-cephem-4-carboxylic acid.

14. A compound selected from the group consisting of:

(7R)-7-[(Z)-2-(2-amino-5-chlorothiazol-4-yl)-2-(hydroxyimino)acetamido]-3-[4-(2-aminoethylthio-methyl)-2-amino-1,3-thiazol-5-ylthio]-3-cephem-4-carboxylic acid, (7R)-7-[(Z)-2-(2-amino-5-chlorothiazol-4-yl)-2-(hydroxyimino)acetamido]-3-[2-(2-aminoethylthio-methyl)pyrid-3-ylthio]-3-cephem-4-carboxylic acid, (7R)-7-[(Z)-2-(5-amino-1,2,4-thiadiazol-3-yl)-2-(hydroxyimino)acetamido]-3-[2-(2-aminoethylthio-methyl)pyrid-3-ylthio]-3-cephem-4-carboxylic acid, (7R)-7-[(Z)-2-(2-amino-5-chlorothiazol-4-yl)-2-(hydroxyimino)acetamido]-3-[4-(2-aminoethylthio-methyl)pyrid-3-ylthio]-3-cephem-4-carboxylic acid, and (7R)-7-[(Z)-2-(5-amino-1,2,4-thiadiazol-3-yl)-2-(hydroxyimino)acetamido]-3-[4-(2-aminoethylthio-methyl)pyrid-3-ylthio]-3-cephem-4-carboxylic acid.

15. The prodrug or salt thereof of claim 1, wherein said compound is active against methicillin-resistant Staphylococcal bacteria selected from the group consisting of *S. aureus* Col (Meth$^R$)(lac−), *S. aureus* 76 (Meth$^R$)(lac+), *S. aureus* ATCC 33593 (Meth$^R$), *S. aureus* Spain #356 (Meth$^R$), and *S. haemolyticus* 05 (Meth$^R$).

16. A method of treating a mammal suffering from a methicillin-resistant Staphylococcal bacterial infection, comprising administering to such mammal a therapeutically effective amount of a prodrug or salt thereof of claim 1.

17. An antibacterial composition for treating a methicillin-resistant Staphylococcal bacterial infection, comprising a therapeutically effective amount of a prodrug or salt thereof of claim 1 in a pharmaceutically acceptable carrier.

18. The prodrug or salt thereof of claim 11, wherein $R'^3$ is selected from the group consisting of hydrogen, methyl, and —C(O)—CH(NH$_2$)CH$_3$.

19. The prodrug or salt thereof of claim 11, wherein alk$_4$ is selected from the group consisting of hydrogen, —CH$_3$, —CH(CH$_3$)$_2$, —CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$COOH, —CH$_2$CH$_2$COOH, —CH$_2$—C(O)NH$_2$, —CH$_2$CH$_2$—C(O)NH$_2$, and

[structure: —CH$_2$— attached to imidazole with NH]

20. A prodrug selected from the group consisting of:

(7R)-7-[(Z)-2-(2-amino-5-chlorothiazol-4-yl)-2-(hydroxyimino)acetamido]-3-{3-[2-N-(L)-ornithylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-prolylaminoethylthiomethyl]pyrid-4-ylthio}-3-cephem-4-carboxylic acid, (7R)-7-[(Z)-2-(2-N-(L)-alanylamino-5-chlorothiazol-4-yl)-2-(hydroxyimino)acetamido]-3-{3-(2-aminoethylthiomethyl]pyrid-4-ylthio}-3-cephem-4-carboxylic acid, (7R)-7-[(Z-2-(2-amino-5-chlorothiazol-4-yl)-2-(hydroxyimino)acetamido]-3-{3-[2-N-(L,L)-alanylalanylaminoethylthiomethyl]pyrid-4-ylthio}-3-cephem-4-carboxylic acid, (7R)-7-[(Z-2-(2-amino-5-chlorothiazol-4-yl)-2-(hydroxyimino)acetamido]-3-{3-[2-N-glycylamino-ethylthiomethyl]pyrid-4-ylthio)-3-cephem-4-carboxylic acid, (7R)-7-[(Z-2-(2-amino-5-chlorothiazol-4-yl)-2-(hydroxyimino)acetamido]-3-{3-[2-N-aspartylamino-ethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-alanylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-(N$_\alpha$-methyl)alanylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-histidylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-valylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-asparagylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-lysylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-serylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-glutaminylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-glutamylaminoethylthiomethyl]pyrid-4-ylthio}-3-cephem-4-carboxylic acid; and, (7R)-7-[(Z)-2-(2-amino-5-chlorothiazol-4-yl)-2-(hydroxyimino)acetamido]-3-{3-[2-N-((5-methyl-1,3-dioxolan-4-en-2-on-4-yl)methoxycarbonyl)aminoethylthiomethyl]pyrid-4-ylthio}-3-cephem-4-carboxylic acid.

ornithylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L,L)-alanylalanylaminoethylthiomethyl]pyrid-4-ylthio}-3-cephem-4-carboxylic acid;

(7R)-7-[(Z)-2-(2-amino-5-chlorothiazol-4-yl)-2-(hydroxyimino)acetamido]-3-{3-[2-N-(L)-aspartylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-alanylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-lysylaminoethylthiomethyl]pyrid-4-ylthio}-3-cephem-4-carboxylic acid, (7R)-7-[(Z)-2-(2-amino-5-chlorothiazol-4-yl)-2-(hydroxyimino)acetamido]-3-{3-[2-N-(L)-glutamylaminoethylthiomethyl]pyrid-4-ylthio}-3-cephem-4-carboxylic acid; and, (7R)-7-[(Z)-2-(2-amino-5-chlorothiazol-4-yl)-2-(hydroxyimino)acetamido]-3-{3-[2-N-((5-methyl-1,3-dioxolan-4-en-2-on-4-yl)methoxycarbonyl)aminoethylthiomethyl]pyrid-4-ylthio}-3-cephem-4-carboxylic acid.

22. The prodrug (7R)-7-[(Z)-2-(2-amino-5-chlorothiazol-4-yl)-2-(hydroxyimino)acetamido]-3-{3-(2-N-(L)-aspartylaminoethylthiomethyl]pyrid-4-ylthio}-3-cephem-4-carboxylic acid, which corresponds to the structure:

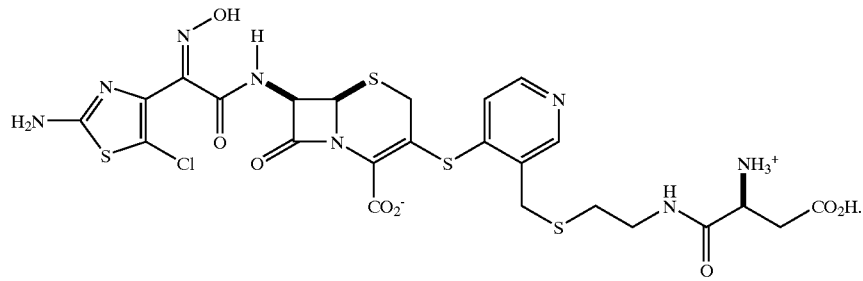

21. A prodrug selected from the group consisting of:

(7R)-7-[(Z)-2-(2-amino-5-chlorothiazol-4-yl)-2-(hydroxyimino)acetamido]-3-{3-[2-N-(L)-

23. The prodrug (7R)-7-[(Z)-2-(5-amino-1,2,4-thiadiazol-3-yl)-2-(hydroxyimino)acetamido]-3-{2-[2-N-(L)-aspartylaminoethylthiomethyl]pyrid-3-ylthio}-3-cephem-4-carboxylic acid, which corresponds to the structure:

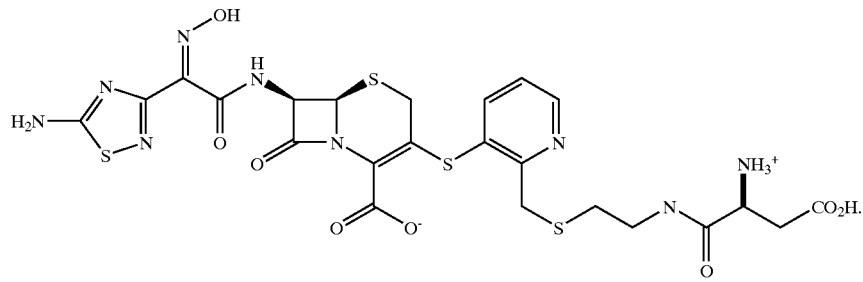

\* \* \* \* \*